United States Patent
Muller et al.

(10) Patent No.: US 9,834,538 B2
(45) Date of Patent: Dec. 5, 2017

(54) 6-, 7-, OR 8-SUBSTITUTED QUINAZOLINONE DERIVATIVES AND COMPOSITIONS COMPRISING AND METHODS OF USING THE SAME

(71) Applicant: Celgene Corporation, Summit, NJ (US)

(72) Inventors: George W. Muller, Rancho Santa Fe, CA (US); Hon-Wah Man, Princeton, NJ (US)

(73) Assignee: Celgene Corporation, Summit, NJ (US)

(*) Notice: Subject to any disclaimer, the term of this patent is extended or adjusted under 35 U.S.C. 154(b) by 0 days.

(21) Appl. No.: 15/415,332

(22) Filed: Jan. 25, 2017

(65) Prior Publication Data

US 2017/0129873 A1    May 11, 2017

Related U.S. Application Data

(60) Continuation of application No. 14/749,448, filed on Jun. 24, 2015, now Pat. No. 9,586,929, which is a division of application No. 13/928,147, filed on Jun. 26, 2013, now Pat. No. 9,096,573, which is a division of application No. 12/238,354, filed on Sep. 25, 2008, now Pat. No. 8,492,395.

(60) Provisional application No. 60/995,676, filed on Sep. 26, 2007.

(51) Int. Cl.
*A61K 31/517* (2006.01)
*C07D 401/04* (2006.01)

(52) U.S. Cl.
CPC ................................ *C07D 401/04* (2013.01)

(58) Field of Classification Search
CPC .................................................. C07D 401/04
See application file for complete search history.

(56) References Cited

U.S. PATENT DOCUMENTS

| | | |
|---|---|---|
| 5,635,517 A | 6/1997 | Muller et al. |
| 2003/0220227 A1 | 11/2003 | Gungor et al. |
| 2005/0239842 A1 | 10/2005 | Zeldis |
| 2008/0161328 A1 | 7/2008 | Muller et al. |

FOREIGN PATENT DOCUMENTS

| | | |
|---|---|---|
| WO | 99/47512 A | 9/1999 |
| WO | 32/059106 A1 | 8/2002 |
| WO | 2007/027527 A2 | 3/2007 |
| WO | 2008/039489 A2 | 4/2008 |

OTHER PUBLICATIONS

El-Fattah et al., "Synthesis and screening of some quinazolinone derivatives," Bulletin of the Faculty of Pharmacy (Cairo University), 273-284 (1976).

Jonsson et al., "Chemical structure and teratogenic properties. II. Synthesis and teratogenic activity in rabbits of some derivatives of phthalimide, isoindoline-1-one, 1,2-benzisothiazoline-3-one-1,1-dioxide and 4(3H)-quinazolinone," Acta Pharm. Suecica, 9:431-466 (1972).

West, "Solid State Chemistry and its Applications," John Wiley & Sons, New York, pp. 358 and 365 (1988).

*Primary Examiner* — Brian McDowell
(74) *Attorney, Agent, or Firm* — Jones Day

(57) ABSTRACT

Provided herein are quinazolinone compounds of formula (I), and pharmaceutically acceptable salts, solvates, clathrates, stereoisomers, and prodrugs thereof. Also provided herein are pharmaceutical compositions comprising the compounds, and methods of use thereof.

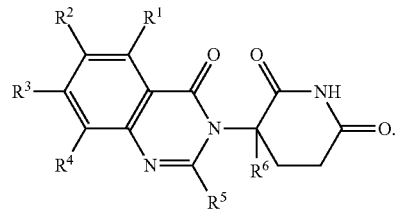

formula (I)

4 Claims, No Drawings

6-, 7-, OR 8-SUBSTITUTED QUINAZOLINONE DERIVATIVES AND COMPOSITIONS COMPRISING AND METHODS OF USING THE SAME

This application is a continuation of U.S. non-provisional patent application Ser. No. 14/749,448, filed Jun. 24, 2015, which is a divisional of U.S. non-provisional patent application Ser. No. 13/928,147, filed Jun. 26, 2013, now U.S. Pat. No. 9,096,573, which is a divisional of U.S. non-provisional patent application Ser. No. 12/238,354, filed Sep. 25, 2008, now U.S. Pat. No. 8,492,395, which claims priority to U.S. provisional application No. 60/995,676, filed Sep. 26, 2007, each of which are incorporated herein by reference in their entireties.

1. FIELD OF THE INVENTION

Provided herein are quinzolinone derivatives. Pharmaceutical compositions comprising the compounds and methods for treating, preventing and managing various disorders are also disclosed.

2. BACKGROUND OF THE INVENTION 2.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance, Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples includes cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

A variety of other diseases and disorders are also associated with, or characterized by, undesired angiogensis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: retrolental fibroplasia; arthritis; and proliferative vitreoretinopathy.

Accordingly, compounds that can control angiogenesis or inhibit the production of certain cytokines, including TNFα, may be useful in the treatment and prevention of various diseases and conditions.

2.2 Methods of Treating Cancer

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics acts by inhibiting DNA synthesis, either directly, or indirectly by inhibiting the biosynthesis of deoxyribonucleotide triphosphate precursors, to prevent DNA replication and concomitant cell division (Gilman et al., Goodman and Gilman's: *The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for effective methods of treating, preventing and managing cancer and other diseases and conditions, including for diseases that are refractory to standard treatments, such as surgery, radiation therapy, chemotherapy and hormonal therapy, while reducing or avoiding the toxicities and/or side effects associated with the conventional therapies.

3. SUMMARY OF THE INVENTION

Provided herein are quinazolinone compounds, and pharmaceutically acceptable salts, solvates (e.g., hydrates), prodrugs, clathrates, or stereoisomers thereof.

Also provided are methods of treating and managing various diseases or disorders. The methods comprise administering to a patient in need of such treatment or management, or having such a disease or disorder, a therapeutically effective amount of a compound provided herein, or a pharmaceutically acceptable salt, solvate, prodrug, clathrate, or stereoisomer thereof.

Also provided herein are methods of preventing various diseases and disorders, which comprise administering to a patient in need of such prevention, or at a risk of such a disease or disorder, a prophylactically effective amount of a compound provided herein, or a pharmaceutically acceptable salt, solvate, prodrug, clathrate, or stereoisomer thereof.

Also provided herein are pharmaceutical compositions, single unit dosage forms, dosing regimens and kits which comprise a compound provided herein, or a pharmaceutically acceptable salt, solvate, prodrug, clathrate, or stereoisomer thereof.

4. DETAILED DESCRIPTION OF THE INVENTION

In one embodiment, provided are quinazolinone compounds, and pharmaceutically acceptable salts, solvates, prodrugs, clathrate, and stereoisomers thereof.

In another embodiment, provided are methods of treating, managing, and preventing various diseases and disorders, which comprises administering to a patient a therapeutically or prophylactically effective amount of a compound provided herein, or a pharmaceutically acceptable salt, solvate, prodrug, clathrate, or stereoisomer thereof. Examples of diseases and disorders are described herein.

In other embodiments, a compound provided herein, or a pharmaceutically acceptable salt, solvate, prodrug, clathrate, or stereoisomer thereof, is administered in combination with another drug ("second active agent") or treatment. Second active agents include small molecules and large molecules (e.g., proteins and antibodies), examples of which are provided herein, as well as stem cells. Methods, or therapies, that can be used in combination with the administration of compounds provided herein include, but are not limited to, surgery, blood transfusions, immunotherapy, biological therapy, radiation therapy, and other non-drug bases therapies presently used to treat, prevent or manage various disorders described herein.

Also provided are pharmaceutical compositions (e.g., single unit dosage forms) that can be used in the methods provided herein. In one embodiment, pharmaceutical compositions comprise a compound provided herein, or a pharmaceutically acceptable salt, solvate, prodrug, clathrate, or stereoisomer thereof, and optionally a second active agent.

4.1 Compounds

In one embodiment, the compounds provided herein for use in the pharmaceutical compositions and methods have the formula (I):

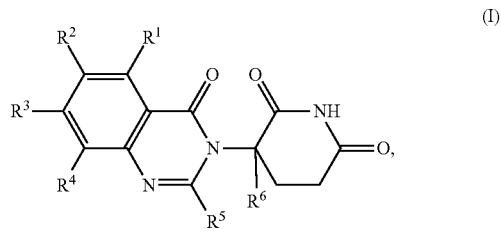

(I)

and pharmaceutically acceptable salts, solvates, and stereoisomers thereof, wherein:

$R^1$ is hydrogen;

each of $R^2$, $R^3$, and $R^4$ is independently: hydrogen; halo; —$(CH_2)_n OH$; $(C_1$-$C_6)$alkyl, optionally, substituted with one or more halo; $(C_1$-$C_6)$alkoxy, optionally substituted with one or more halo; or —$(CH_2)_n NHR^4$, wherein $R^a$ is:

hydrogen;

$(C_1$-$C_6)$alkyl, optionally substituted with one or more halo;

—$(CH_2)_n$-(6 to 10 membered aryl);

—$C(O)$—$(CH_2)_n$-(6 to 10 membered aryl) or —$C(O)$—$(CH_2)_n$-(6 to 10 membered heteroaryl), wherein the aryl or heteroaryl is optionally substituted with one or more of: halo; —$SCF_3$; $(C_1$-$C_6)$alkyl, said alkyl itself optionally substituted with one or more halo; or $(C_1$-$C_6)$alkoxy, said alkoxy itself optionally substituted with one or more halo;

—$C(O)$—$(C_1$-$C_8)$alkyl, wherein the alkyl is optionally substituted with one or more halo;

—$C(O)$—$(CH_2)_n$—$(C_3$-$C_{10}$-cycloalkyl);

—$C(O)$—$(CH_2)_n$—$NR^b R^c$, wherein $R^b$ and $R^c$ are each independently:

hydrogen;

$(C_1$-$C_6)$alkyl, optionally substituted with one or more halo;

$(C_1$-$C_6)$alkoxy, optionally substituted with one or more halo; or 6 to 10 membered aryl, optionally substituted with one or more of: halo;

$(C_1$-$C_6)$alkyl, itself optionally substituted with one or more halo; or $(C_1$-$C_6)$alkoxy, itself optionally substituted with one or more halo;

—$C(O)$—$(CH_2)_n$—$O$—$(C_1$-$C_6)$alkyl; or

—$C(O)$—$(CH_2)_n$—$O$—$(CH_2)_n$-(6 to 10 membered aryl); or two of $R^1$-$R^4$ together can form a 5 or 6 membered ring, optionally substituted with one or more of: halo; $(C_1$-$C_6)$alkyl, optionally substituted with one or more halo; and $(C_1$-$C_6)$alkoxy, optionally substituted with one or more halo;

$R^5$ is: hydrogen; —$(CH_2)_n OH$; phenyl; —$O$—$(C_1$-$C_6)$alkyl; or $(C_1$-$C_6)$alkyl, optionally substituted with one or more halo;

$R^6$ is: hydrogen; or $(C_1-C_6)$alkyl, optionally substituted with one or more halo; and n is 0, 1, or 2.

In another embodiment, provided herein are compounds of formula (II):

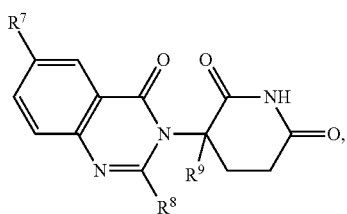
(II)

and pharmaceutically acceptable salts, solvates, and stereoisomers thereof, wherein:

$R^7$ is: hydrogen; halo; —$(CH_2)_n$OH; $(C_1-C_6)$alkyl, optionally substituted with one or more halo; $(C_1-C_6)$alkoxy, optionally substituted with one or more halo; or —$(CH_2)_n$NHR$^d$, wherein R$^d$ is:

hydrogen;

$(C_1-C_6)$alkyl, optionally substituted with one or more halo;

—$(CH_2)_n$-(6 to 10 membered aryl);

—C(O)—$(CH_2)_n$-(6 to 10 membered aryl) or —C(O)—$(CH_2)_2$-(6 to 10 membered heteroaryl), wherein the aryl or heteroaryl is optionally substituted with one or more of: halo, —SCF$_3$; $(C_1-C_6)$alkyl, itself optionally substituted with one or more halo; or $(C_1-C_6)$alkoxy, itself optionally substituted with one or more halo;

—C(O)—$(C_3-C_8)$alkyl, wherein the alkyl is optionally substituted with one or more halo;

—C(O)—$(CH_2)_n$—$(C_3-C_{10}$-cycloalkyl);

—C(O)—$(CH_2)_n$—NR$^e$R$^f$, wherein R$^e$ and R$^f$ are each independently:

hydrogen;

$(C_1-C_6)$alkyl, optionally substituted with one or more halo;

$(C_1-C_6)$alkoxy, optionally substituted with one or more halo; or 6 to 10 membered aryl, optionally substituted with one or more of: halo;

$(C_1-C_6)$alkyl, itself optionally substituted with one or more halo; or $(C_1-C_6)$alkoxy, itself optionally substituted with one or more halo;

—C(O)—$(CH_2)_n$—O—$(C_1-C_6)$alkyl; or

—C(O)—$(CH_2)_n$—O—$(CH_2)_n$-(6 to 10 membered aryl);

$R^8$ is: hydrogen; —$(CH_2)_n$OH; phenyl; —O—$(C_1-C_6)$alkyl; or $(C_1-C_6)$alkyl, optionally substituted with one or more halo;

$R^9$ is: hydrogen; or $(C_1-C_6)$alkyl, optionally substituted with one or more halo; and n is 0, 1, or 2.

In another embodiment, provided herein are compounds of formula (III):

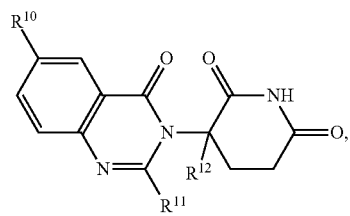
(III)

and pharmaceutically acceptable salts, solvates, and stereoisomers thereof, wherein:

$R^{10}$ is: hydrogen; halo; —$(CH_2)_n$OH; $(C_1-C_6)$alkyl, optionally substituted with one or more halo; or $(C_1-C_6)$alkoxy, optionally substituted with one or more halo;

$R^{11}$ is: hydrogen; —$(CH_2)_n$OH; phenyl; —O—$(C_1-C_6)$alkyl; or $(C_1-C_6)$alkyl, optionally substituted with one or more halo;

$R^{12}$ is: hydrogen; or $(C_1-C_6)$alkyl, optionally substituted with one or more halo; and n is 0, 1, or 2.

In one embodiment, $R^{10}$ is hydrogen. In another embodiment, $R^{10}$ is halo. In another embodiment, $R^{10}$ is $(C_1-C_6)$alkyl, optionally substituted with one or more halo. In another embodiment, $R^{10}$ is —$(CH_2)_n$OH or hydroxyl. In another embodiment, $R^{10}$ is $(C_1-C_6)$alkoxy, optionally substituted with one or more halo.

In another embodiment, $R^{11}$ is hydrogen. In another embodiment, $R^{11}$ is —$(CH_2)_n$OH or hydroxyl. In another embodiment, $R^{11}$ is phenyl. In another embodiment, $R^{11}$ is —O—$(C_1-C_6)$alkyl, optionally substituted with one or more halo. In another embodiment, $R^{11}$ is $(C_1-C_6)$alkyl, optionally substituted with one or more halo.

In one embodiment, $R^{12}$ is hydrogen. In another embodiment, $R^{12}$ is $(C_1-C_6)$alkyl, optionally substituted with one or more halo.

In one embodiment, n is 0. In another embodiment, n is 1. In another embodiment, n is 2.

Compounds provided herein encompass any of the combinations of $R^{10}$, $R^{11}$, $R^{12}$ and n described above.

In one specific embodiment, $R^{10}$ is halo. In another embodiment, $R^{10}$ is hydroxyl. In another embodiment, $R^{10}$ is methyl.

In another specific embodiment, $R^{11}$ is hydrogen. In another embodiment, $R^{11}$ is methyl.

In another specific embodiment, $R^{12}$ is hydrogen. In another embodiment, $R^{12}$ is methyl.

Specific compounds include, but are not limited to:

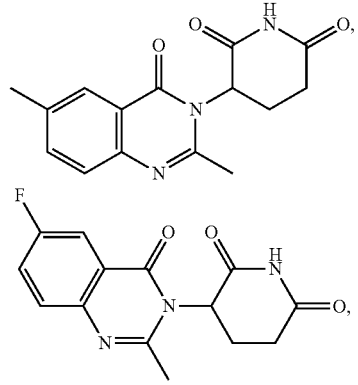

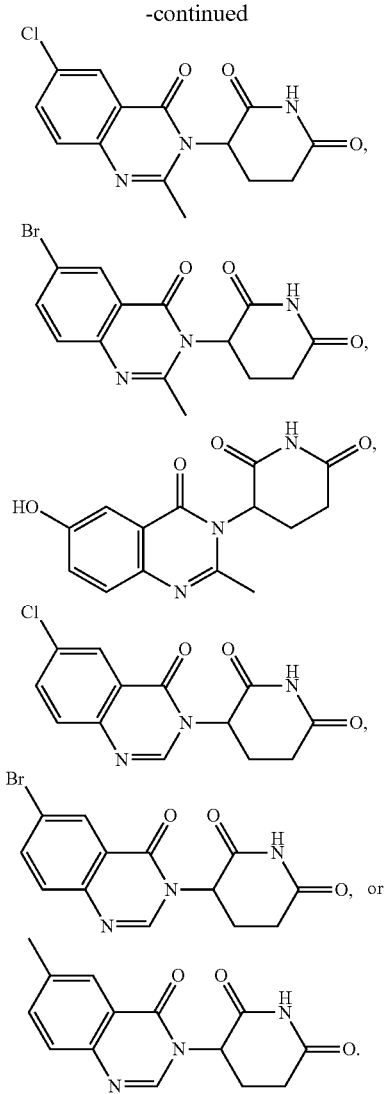

In another embodiment, provided herein are compounds of formula (IV):

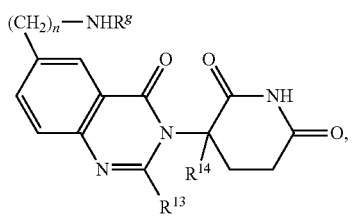

and pharmaceutically acceptable salts, solvates, and stereoisomers thereof, wherein:

$R^3$ is:
hydrogen;
($C_1$-$C_6$)alkyl, optionally substituted with one or more halo;
—($CH_2$)$_n$-(6 to 10 membered aryl);
—C(O)—($CH_2$)$_n$-(6 to 10 membered aryl) or —C(O)—($CH_2$)$_n$-(6 to 10 membered heteroaryl), wherein the aryl or heteroaryl is optionally substituted with one or more of: halo; —$SCF_3$; ($C_1$-$C_6$) alkyl, itself optionally substituted with one or more halo; or ($C_1$-$C_6$)alkoxy, itself optionally substituted with one or more halo;
—C(O)—($C_1$-$C_8$)alkyl, wherein the alkyl is optionally substituted with one or more halo;
—C(O)—($CH_2$)$_n$—($C_3$-$C_{10}$-cycloalkyl);
—C(O)—($CH_2$)$_n$—$NR^h R^i$, wherein $R^h$ and $R^i$ are each independently:
hydrogen;
($C_1$-$C_6$)alkyl, optionally substituted with one or more halo;
($C_1$-$C_6$)alkoxy, optionally substituted with one or more halo; or
6 to 10 membered aryl, optionally substituted with one or more of: halo;
($C_1$-$C_6$)alkyl, itself optionally substituted with one or more halo; or
($C_1$-$C_6$)alkoxy, itself optionally substituted with one or more halo;
—C(O)—($CH_2$)$_n$—O—($C_1$-$C_6$)alkyl; or
—C(O)—($CH_2$)$_n$—O—($CH_2$)$_n$-(6 to 10 membered aryl);

$R^{13}$ is: hydrogen; —($CH_2$)$_n$OH; phenyl; —O—($C_1$-$C_6$) alkyl; or ($C_1$-$C_6$)alkyl, optionally substituted with one or more halo;

$R^{14}$ is: hydrogen; or ($C_1$-$C_6$)alkyl, optionally substituted with one or more halo; and n is 0, 1, or 2.

In one embodiment, $R^8$ is hydrogen. In another embodiment, $R^8$ is ($C_1$-$C_6$)alkyl, optionally substituted with one or more halo. In another embodiment, $R^8$ is —($CH_2$)$_n$-(6 to 10 membered aryl). In another embodiment, $R^8$ is —C(O)—($CH_2$)$_n$-(6 to 10 membered aryl) or —C(O)—($CH_2$)$_n$-(6 to 10 membered heteroaryl), wherein the aryl or heteroaryl is optionally substituted as described above. In another embodiment, $R^2$ is —C(O)—($C_1$-$C_6$)alkyl, wherein the alkyl is optionally substituted with one or more halo. In another embodiment, $R^8$ is —C(O)—($CH_2$)$_n$—($C_3$-$C_{10}$-cycloalkyl). In another embodiment, $R^8$ is —C(O)—($CH_2$)$_n$—$NR^h R^i$, wherein $R^h$ and $R^i$ are as described above. In another embodiment, $R^8$ is —C(O)—($CH_2$)$_n$—O—($C_1$-$C_6$)alkyl. In another embodiment, $R^8$ is —C(O)—($CH_2$)$_n$—O—($CH_2$)$_n$-(6 to 10 membered aryl).

In one embodiment, $R^{13}$ is hydrogen. In another embodiment, $R^{13}$ is —($CH_2$)$_n$OH or hydroxyl. In another embodiment, $R^{13}$ is phenyl. In another embodiment, $R^{13}$ is —O—($C_1$-$C_6$)alkyl, optionally substituted with one or more halo. In another embodiment, $R^{13}$ is ($C_1$-$C_6$)alkyl, optionally substituted with one or more halo.

In one embodiment, $R^{14}$ is hydrogen. In another embodiment, $R^{14}$ is ($C_1$-$C_6$)alkyl, optionally substituted with one or more halo.

In one embodiment, n is 0. In another embodiment, n is 1. In another embodiment, n is 2.

Compounds provided herein encompass any of the combinations of $R^8$, $R^{13}$, $R^{14}$ and n described above.

In one specific embodiment, $R^8$ is hydrogen, and n is 0 or 1. In another embodiment, $R^8$ is —C(O)—($C_1$-$C_6$)alkyl. In another embodiment, $R^8$ is —C(O)-phenyl, optionally substituted with one or more methyl, halo, and/or ($C_1$-$C_6$) alkoxy.

In another specific embodiment, $R^{13}$ is methyl. In another embodiment, $R^{14}$ is hydrogen.

Specific compounds include, but are not limited to:
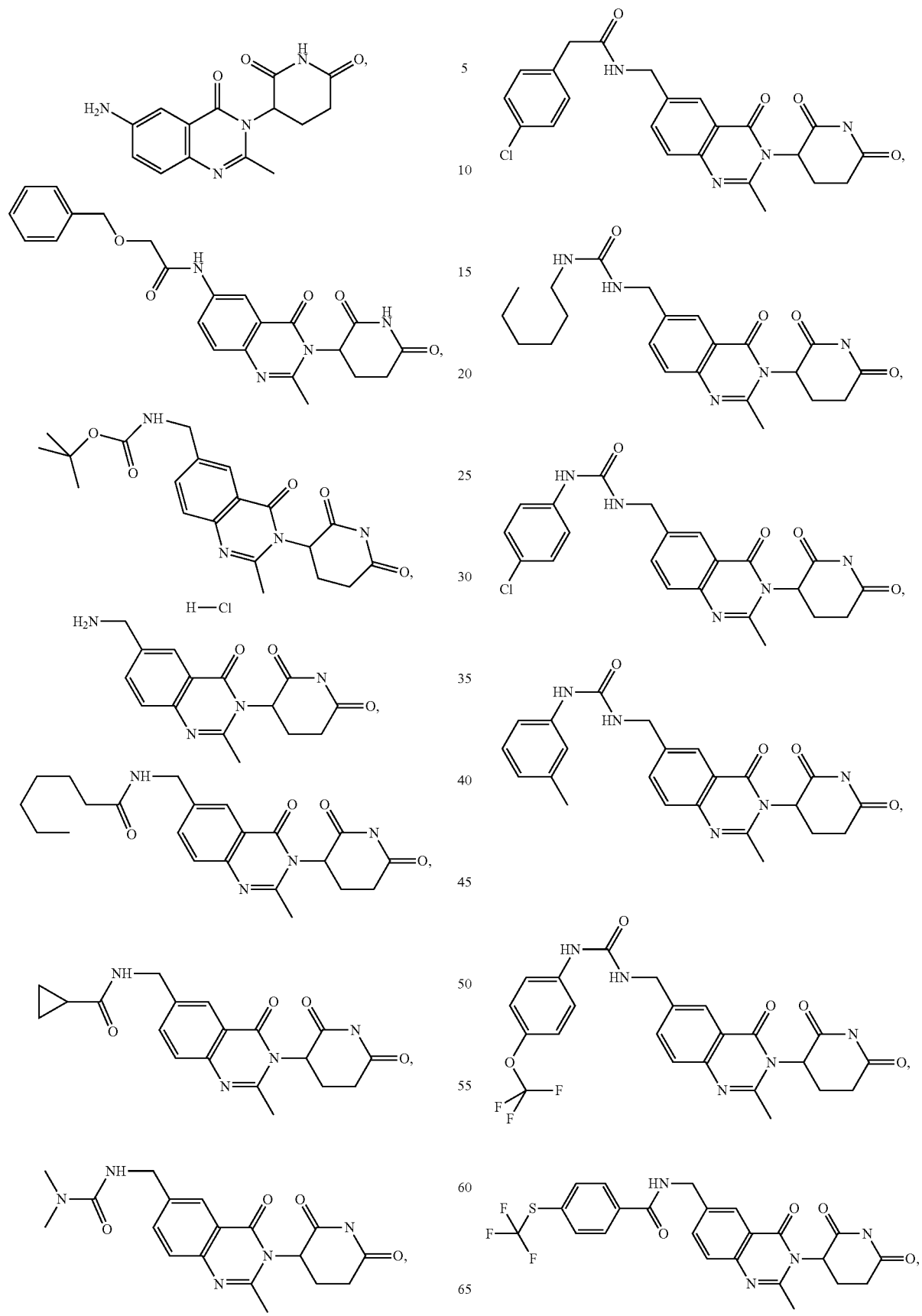

-continued

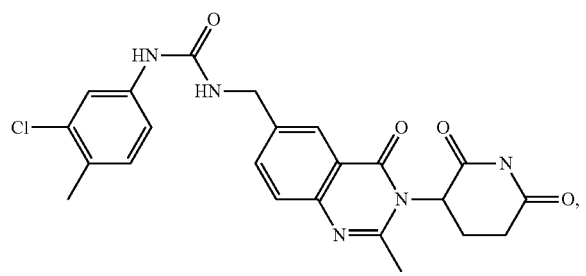

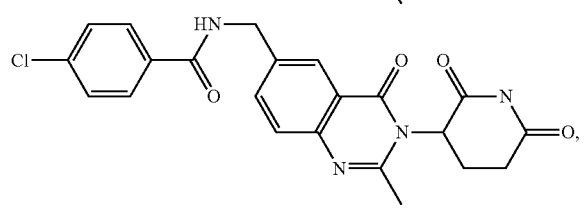

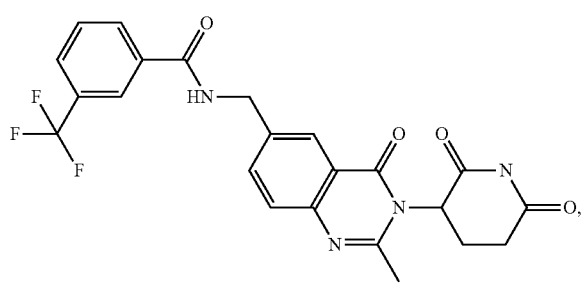

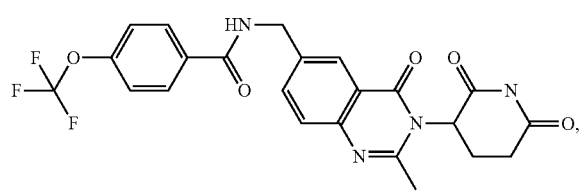

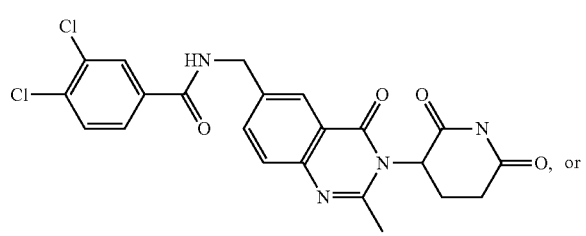

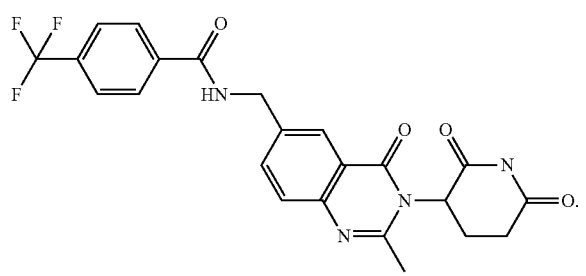

In another embodiment, provided herein are compounds of formula (V):

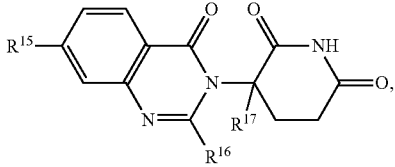

(V)

and pharmaceutically acceptable salts, solvates, and stereoisomers thereof, wherein:

$R^{15}$ is: hydrogen; halo; —$(CH_2)_n$OH; $(C_1-C_6)$alkyl, optionally substituted with one or more halo; $(C_1-C_6)$alkoxy, optionally substituted with one or more halo; or —$(CH_2)_n$NHR$^j$, wherein R$^j$ is:

hydrogen;

$(C_1-C_6)$alkyl, optionally substituted with one or more halo;

—$(CH_2)_n$-(6 to 10 membered aryl);

—C(O)—$(CH_2)_n$-(6 to 10 membered aryl) or —C(O)—$(CH_2)_n$-(6 to 10 membered heteroaryl, wherein the aryl or heteroaryl is optionally substituted with one or more of: halo; —SCF$_3$; $(C_1-C_6)$alkyl, itself optionally substituted with one or more halo; or $(C_1-C_6)$alkoxy, itself optionally substituted with one or more halo;

—C(O)—$(C_1-C_6)$alkyl, wherein the alkyl is optionally substituted with one or more halo;

—C(O)—$(CH_2)_n$—$(C_3-C_{10}$-cycloalkyl);

—C(O)—$(CH_2)_n$—NR$^k$R$^l$, wherein R$^k$ and R$^l$ are each independently:

hydrogen;

$(C_1-C_6)$alkyl, optionally substituted with one or more halo;

$(C_1-C_6)$alkoxy, optionally substituted with one or more halo; or 6 to 10 membered aryl, optionally substituted with one or more of: halo;

$(C_1-C_6)$alkyl, itself optionally substituted with one or more halo; or $(C_1-C_6)$alkoxy, itself optionally substituted with one or more halo;

—C(O)—$(CH_2)_n$—O—$(C_1-C_6)$alkyl; or

—C(O)—$(CH_2)_n)$—O—$(CH_2)_n$-(6 to 10 membered aryl);

$R^{16}$ is: hydrogen; —$(CH_2)_n$OH; phenyl; —O—$(C_1-C_6)$alkyl; or $(C_1-C_6)$alkyl, optionally substituted with one or more halo;

$R^{17}$ is: hydrogen; or $(C_1-C_6)$alkyl, optionally substituted with one or more halo; and n is 0, 1, or 2.

In one embodiment, $R^{15}$ is hydrogen. In another embodiment, $R^{15}$ is halo. In another embodiment, $R^{15}$ is $(C_1-C_6)$alkyl, optionally substituted with one or more halo. In another embodiment, $R^{15}$ is —$(CH_2)_n$OH or hydroxyl. In another embodiment, $R^{15}$ is $(C_1-C_6)$alkoxy, optionally substituted with one or more halo.

In one embodiment, $R^{15}$ is —$(CH_2)_n$NHR$^j$. In one embodiment, wherein $R^{15}$ is —$(CH_2)_n$NHR$^j$, R$^j$ is hydrogen. In another embodiment, R$^j$ is $(C_1-C_6)$alkyl, optionally substituted with one or more halo. In another embodiment, R$^j$ is —$(CH_2)_n$-(6 to 10 membered aryl). In another embodiment, R$^j$ is —C(O)—$(CH_2)_n$-(6 to 10 membered aryl) or —C(O)—$(CH_2)_n$-(6 to 10 membered heteroaryl), wherein the aryl or heteroaryl is optionally substituted as described above. In another embodiment, R$^j$ is —C(O)—$(C_1-C_6)$alkyl, wherein the alkyl is optionally substituted with one or more halo. In another embodiment, $R^j$ is —C(O)—(CH$_2$)$_n$—(C$_3$-C$_{10}$-cycloalkyl). In another embodiment, $R^j$ is —C(O)—(CH$_2$)$_n$—NR$^k$R$^l$, wherein R$^k$ and R$^l$ are as defined above. In another embodiment, $R^1$ is —C(O)—(CH$_2$)$_n$—O—(C$_1$-C$_6$)alkyl. In another embodiment, $R^j$ is —C(O)—(CH$_2$)$_n$—O—(CH$_2$)$_n$-(6 to 10 membered aryl).

In one embodiment, $R^{16}$ is hydrogen. In another embodiment, $R^{16}$ is —(CH$_2$)$_n$OH or hydroxyl. In another embodiment, $R^{16}$ is phenyl. In another embodiment, $R^{16}$ is —O—(C$_1$-C$_6$)alkyl, optionally substituted with one or more halo. In another embodiment, $R^{16}$ is (C$_1$-C$_6$)alkyl, optionally substituted with one or more halo.

In one embodiment, $R^{17}$ is hydrogen. In another embodiment, $R^{17}$ is (C$_1$-C$_6$)alkyl, optionally substituted with one or more halo.

In one embodiment, n is 0. In another embodiment, n is 1. In another embodiment, n is 2.

Compounds provided herein encompass any of the combinations of $R^{15}$, $R^{16}$, $R^{17}$ and n described above.

In one specific embodiment, $R^{15}$ is methyl. In another embodiment, $R^{15}$ is halo. In another embodiment, $R^{15}$ is —CF$_3$. In another embodiment, $R^{15}$ is —(CH$_2$)$_n$NHR$^j$.

In one specific embodiment, $R^{15}$ is —(CH$_2$)$_n$NHR$^j$, $R^j$ is hydrogen, and n is 0 or 1. In another embodiment, wherein $R^{15}$ is —(CH$_2$)$_n$NHR$^j$, $R^j$ is —C(O)—(O)—(C$_1$-C$_6$)alkyl.

In one specific embodiment, $R^{16}$ is hydrogen. In another embodiment, $R^{16}$ is methyl. In another specific embodiment, $R^{17}$ is hydrogen or methyl.

Specific compounds include, but are not limited to:

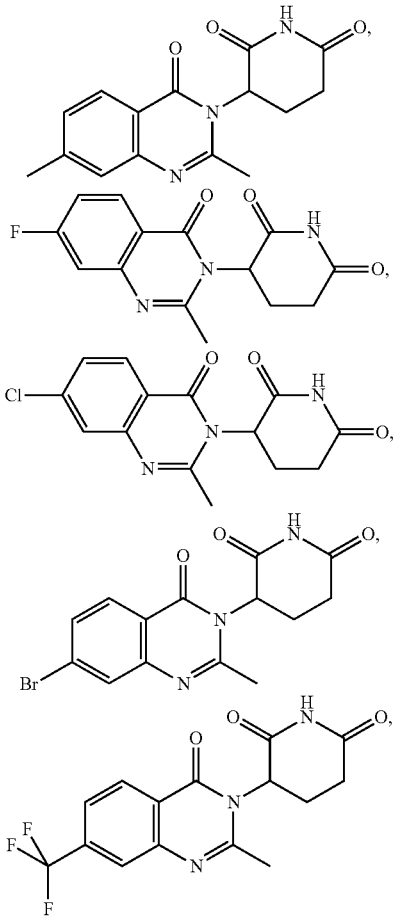

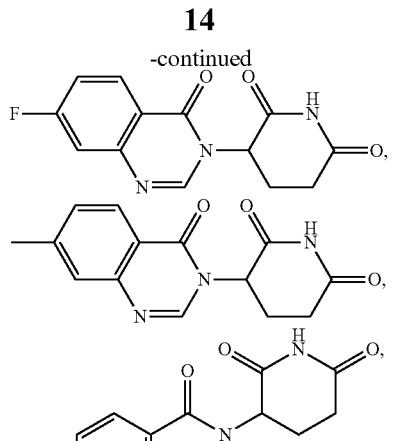

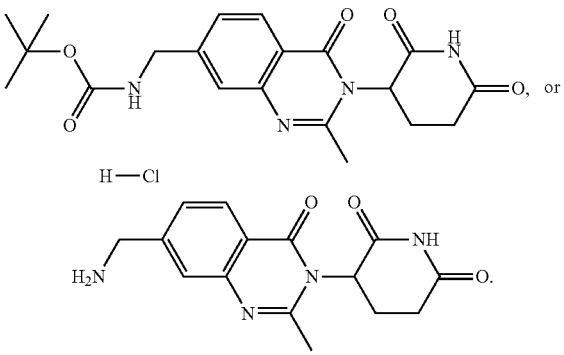

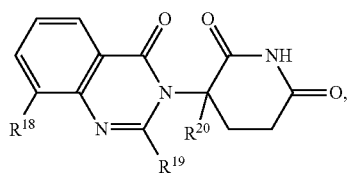

In another embodiment, provided herein are compounds of formula (VI):

$$(VI)$$

and pharmaceutically acceptable salts, solvates, and stereoisomers thereof, wherein:

$R^{18}$ is: hydrogen; halo; —(CH$_2$)$_n$OH; (C$_1$-C$_6$)alkyl, optionally substituted with one or more halo; (C$_1$-C$_6$) alkoxy, optionally substituted with one or more halo; or —(CH$_2$)$_n$NHR$^m$, wherein R$^m$ is:

hydrogen;

(C$_1$-C$_6$)alkyl, optionally substituted with one or more halo;

—(CH$_2$)$_n$-(6 to 10 membered aryl);

—C(O)—(CH$_2$)$_n$-(6 to 10 membered aryl) or —C(O)—(CH$_2$)$_n$-(6 to 10 membered heteroaryl), wherein the aryl or heteroaryl is optionally substituted with one or more of: halo; —SCF$_3$; (C$_1$-C$_6$)alkyl, itself optionally substituted with one or more halo; or (C$_1$-C$_6$)alkoxy, itself optionally substituted with one or more halo;

—C(O)—(C$_1$-C$_8$)alkyl, wherein the alkyl is optionally substituted with one or more halo;

—C(O)—(CH$_2$)$_n$—(C$_3$-C$_{10}$)-cycloalkyl);

—C(O)—(CH$_2$)$_n$—NR$^b$R$^c$, wherein R$^b$ and R$^c$ are each independently:

hydrogen;

(C$_1$-C$_6$)alkyl, optionally substituted with one or more halo;

(C$_1$-C$_6$)alkoxy, optionally substituted with one or more halo; or 6 to 10 membered aryl, optionally substituted with one or more of: halo;

(C$_1$-C$_6$)alkyl, itself optionally substituted with one or more halo; or (C$_1$-C$_6$)alkoxy, itself optionally substituted with one or more halo;

—C(O)—(CH$_2$)$_n$—O—(C$_1$-C$_6$)alkyl; or

—C(O)—(CH$_2$)$_n$—O—(CH$_2$)$_n$-(6 to 10 membered aryl);

R$^{19}$ is: hydrogen; —(CH$_2$)$_n$OH; phenyl; —O—(C$_1$-C$_6$)alkyl; or (C$_1$-C$_6$)alkyl, optionally substituted with one or more halo;

R$^{20}$ is: hydrogen; or (C$_1$-C$_6$)alkyl, optionally substituted with one or more halo; and n is 0, 1, or 2.

In one embodiment, R$^{18}$ is hydrogen. In another embodiment, R$^{18}$ is halo. In another embodiment, R$^{18}$ is (C$_1$-C$_6$)alkyl, optionally substituted with one or more halo. In another embodiment, R$^{18}$ is —(CH$_2$)$_n$OH or hydroxyl. In another embodiment, R$^{18}$ is (C$_1$-C$_6$)alkoxy, optionally substituted with one or more halo.

In another embodiment, R$^{18}$ is —(CH$_2$)$_n$NHR$^m$. In one embodiment, wherein R$^{28}$ is —(CH$_2$)$_n$NHR$^s$, R$^s$ is hydrogen. In another embodiment, R$^m$ is (C$_1$-C$_6$)alkyl, optionally substituted with one or more halo. In another embodiment, R$^m$ is —(CH$_2$)$_n$-(6 to 10 membered aryl). In another embodiment, R$^m$ is —C(O)—(CH$_2$)$_n$-(6 to 10 membered aryl) or —C(O)—(CH$_2$)$_n$-(6 to 10 membered heteroaryl), wherein the aryl or heteroaryl is optionally substituted as described above. In another embodiment, R$^s$ is —C(O)—(C$_1$-C$_6$)alkyl, wherein the alkyl is optionally substituted with one or more halo. In another embodiment, R$^m$ is —C(O)—(CH$_2$)$_n$—(C$_3$-C$_{10}$-cycloalkyl). In another embodiment, R$^m$ is —C(O)—(CH$_2$)$_n$—NR$''$R$^o$, wherein R$''$ and R$^o$ are as described above. In another embodiment, R$^m$ is —C(O)—(CH$_2$)$_n$—O—(C$_1$-C$_6$)alkyl. In another embodiment, R$^m$ is —C(O)—(CH$_2$)$_n$—O—(CH$_2$)$_n$-(6 to 10 membered aryl).

In one embodiment, R$^{19}$ is hydrogen. In another embodiment, R$^{19}$ is —(CH$_2$)$_n$OH or hydroxyl. In another embodiment, R$^{19}$ is phenyl. In another embodiment, R$^{19}$ is —O—(C$_1$-C$_6$)alkyl, optionally substituted with one or more halo. In another embodiment, R$^{19}$ is (C$_1$-C$_6$)alkyl, optionally substituted with one or more halo.

In one embodiment, R$^{20}$ is hydrogen. In another embodiment, R$^{20}$ is (C$_1$-C$_6$)alkyl, optionally substituted with one or more halo.

In one embodiment, n is 0. In another embodiment, n is 1. In another embodiment, n is 2.

Compounds provided herein encompass any of the combinations of R$^{18}$, R$^{19}$, R$^{20}$ and n described above.

In one specific embodiment, R$^{18}$ is methyl. In another embodiment, R$^{18}$ is halo. In another embodiment, R$^{18}$ is hydroxyl. In another embodiment, R$^{18}$ is —CF$_3$.

In one specific embodiment, R$^{19}$ is hydrogen. In another embodiment, R$^{19}$ is methyl. In another specific embodiment, R$^{20}$ is hydrogen.

Specific compounds include, but are not limited to:

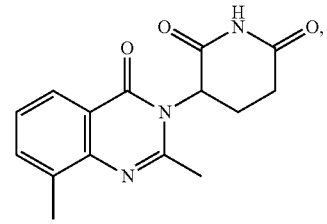

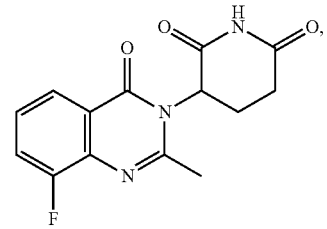

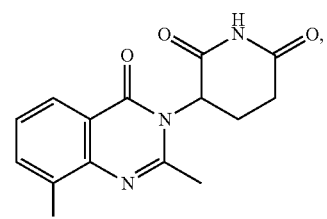

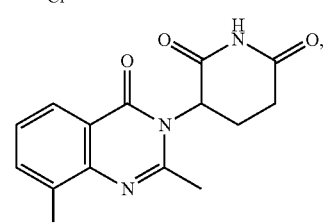

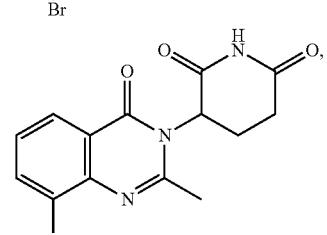

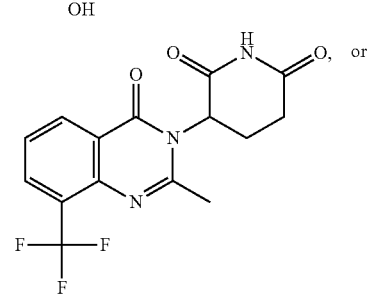

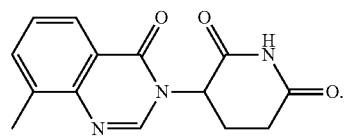

In another embodiment, provided herein are compounds of formula (VII):

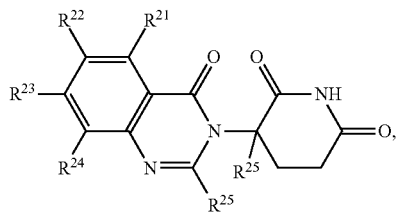

(VII)

and pharmaceutically acceptable salts, solvates, and stereoisomers thereof, wherein:

$R^{21}$ is hydrogen;

$R^{22}$, $R^{23}$, and $R^{24}$ are each independently: halo; —$(CH_2)_n$OH; $(C_1-C_6)$alkyl, optionally substituted with one or more halo; $(C_1-C_6)$alkoxy, optionally substituted with one or more halo; or two of $R^{21}$-$R^{24}$ together form a 5 to 6 membered ring, optionally substituted with one or more of: halo; $(C_1-C_6)$alkyl, optionally substituted with one or more halo; and $(C_1-C_6)$alkoxy, optionally substituted with one or more halo;

$R^{25}$ is: hydrogen; —$(CH_2)_n$OH; phenyl; —O—$(C_1-C_6)$alkyl; or $(C_1-C_6)$alkyl, optionally substituted with one or more halo;

$R^{26}$ is: hydrogen; or $(C_1-C_6)$alkyl, optionally substituted with one or more halo; and n is 0, 1, or 2.

In one embodiment, two of $R^{22}$-$R^{24}$ are halo. In another embodiment, two of $R^{22}$-$R^{24}$ are $(C_1-C_6)$alkyl, optionally substituted with one or more halo. In another embodiment, two of $R^{22}$-$R^{24}$ are $(C_1-C_6)$alkoxy, optionally substituted with one or more halo.

In another embodiment, one of $R^{22}$-$R^{24}$ are is halo, and another one of $R^{22}$-$R^{24}$ is $(C_1-C_6)$alkyl, optionally substituted with one or more halo. In another embodiment, one of $R^{22}$-$R^{24}$ is halo, and another one of $R^{22}$-$R^{24}$ is $(C_1-C_6)$alkoxy, optionally substituted with one or more halo. In another embodiment, one of $R^{22}$-$R^{24}$ is $(C_1-C_6)$alkoxy, optionally substituted with one or more halo, and another one of $R^{22}$-$R^{24}$ is $(C_1-C_6)$alkyl, optionally substituted with one or more halo.

In another embodiment, two of $R^{22}$-$R^{24}$ together form a 5 to 6 membered ring. In one specific embodiment, $R^{22}$ and $R^{23}$ together form a 5 to 6 membered ring. In one specific embodiment, $R^{22}$ and $R^{23}$ together form phenyl ring. In another embodiment, the ring formed by $R^{22}$ and $R^{23}$ is optionally substituted with one or more of: halo, $(C_1-C_6)$alkyl, optionally substituted with one or more halo; and $(C_1-C_6)$alkoxy, optionally substituted with one or more halo.

In one embodiment, $R^{25}$ is hydrogen. In another embodiment, $R^{25}$ is —$(CH_2)_n$OH or hydroxyl. In another embodiment, $R^{25}$ is phenyl. In another embodiment, $R^{25}$ is —O—$(C_1-C_6)$alkyl, optionally substituted with one or more halo. In another embodiment, $R^{25}$ is $(C_1-C_6)$alkyl, optionally substituted with one or more halo.

In one embodiment, $R^{26}$ is hydrogen. In another embodiment, $R^{26}$ is $(C_1-C_6)$alkyl, optionally substituted with one or more halo.

In one embodiment, n is 0. In another embodiment, n is 1. In another embodiment, n is 2.

Compounds provided herein encompass any of the combinations of $R^{21}$, $R^{22}$, $R^{23}$, $R^{24}$, $R^{25}$, $R^{26}$ and n described above.

Specific compounds include, but are not limited to:

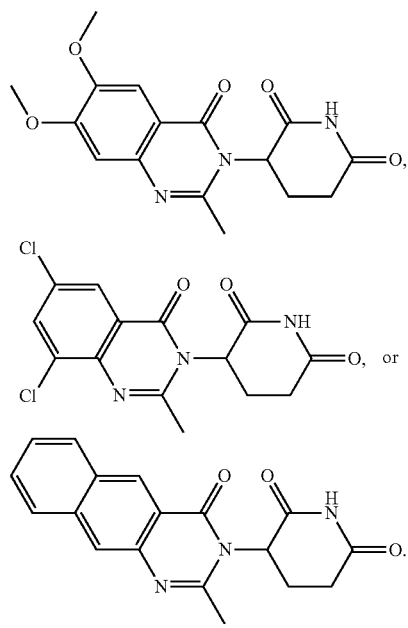

As used herein, and unless otherwise specified, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isothionic, lactic, maleic, malic, mandelic, methanesulfonic, mucic, nitric, pamoic, pantothenic, phenylacetic, propionic, phosphoric, salicyclic, stearic, succinic, sulfanilic, sulfuric, tartaric acid, p-toluenesulfonic and the like. In one embodiment, suitable are hydrochloric, hydrobromic, phosphoric and sulfuric acids.

As used herein, and unless otherwise specified, the term "solvate" means a compound that further includes a stoichiometric or non-stoichiometric amount of solvent bound by non-covalent intermolecular forces. Where the solvent is water, the solvate is a hydrate.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moioeties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —$NO_2$, —ONO, or —$ONO_2$ moieties. Prodrugs can typically be prepared using well-known methods, such as those described in *Burger's Medicinal Chemistry and Drug Discovery*, 172-178, 949-982 (Manfred E. Wolff ed., 5th ed. 1995) and *Design of Prodrugs* (H. Bundgaard ed., Elsevier, New York 1985).

As used herein, and unless otherwise specified, the terms "biohydrolyzable carbamate," "biohydrolyzable carbonate," "biohydrolyzable ureide" and "biohydrolyzable phosphate" means a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, carbamates that include lower alkylamine, substituted ethylenediamine, aminoacid, hydroxyalkylamine, heterocyclic and heteroaromatic amine, and polyether amine moieties.

As used herein, and unless otherwise specified, the term "stereoisomer" encompasses all enantiomerically/stereomerically pure and enantiomerically/stereomerically enriched compounds provided herein.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

As used herein, and unless otherwise indicated, the term "alkyl" refers to a saturated straight chain or branched hydrocarbon having a number of carbon atoms as specified herein. Representative saturated straight chain alkyls include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The term "alkyl" also encompasses cycloalkyl.

As used herein, and unless otherwise specified, the term "cycloalkyl" means a specie of alkyl containing from 3 to 15 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more of the substituents.

As used herein, the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Specifically, the aryl group is a monocyclic ring or bicyclic ring. Representative aryl groups include phenyl, anthracenyl, fluorenyl, indenyl, azulenyl, phenanthrenyl and naphthyl.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Methods of Treatment, Prevention and Management

Provided herein are methods of treating, preventing, and/or managing various diseases or disorders using a compound provided herein, or a pharmaceutically acceptable salt, solvate (e.g., hydrate), prodrug, clathrate, or stereoisomer thereof. Without being limited by a particular theory, compounds provided herein can control angiogenesis or inhibit the production of certain cytokines including, but not limited to, TNF-α, IL-1β, IL-12, IL-18, GM-CSF, and/or IL-6. Without being limited by a particular theory, compounds provided herein can stimulate the production of certain other cytokines including IL-10, and also act as a costimulatory signal for T cell activation, resulting in increased production of cytokines such as, but not limited to, IL-12 and/or IFN-γ. In addition, compounds provided herein can enhance the effects of NK cells and antibody-mediated cellular cytotoxicity (ADCC). Further, compounds provided herein may be immunomodulatory and/or cytotoxic, and thus, may be useful as chemotherapeutic agents. Consequently, without being limited by a particular theory, some or all of such characteristics possessed by the compounds provided herein may render them useful in treating, managing, and/or preventing various diseases or disorders.

Examples of diseases or disorders include, but are not limited to, cancer, disorders associated with angiogenesis, pain including, but not limited to, Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNFα related disorders, and other various diseases and disorders.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "propylactically effective amount" can encompass an amount that improves overall prophylaxis or enhances the prophylactic efficacy of another prophylactic agent.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Specific examples of cancer include, but are not limited to, cancers of the skin, such as melanoma; lymph node, breast; cervix, uterus, gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other specific cancers include, but are not limited to, advanced malignancy, amyloidosis, neuroblastoma, meningioma, hemangiopericytomas, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendodrine tumor, rectal adenocarbinoma, Dukes C & D colorectal cancer, unresectable colorectal carbinoma, metastatic hepatocellular carbinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous T-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carbinoma, papillary serous carcinoma, gynecologic sarcoma, soft tissue sarcoma, scleroderma, cutaneous vasculitis, Langerbans cell histiocytosis, leiomyosarcoma, fibrodysplasia ossificans progressive, hormone refractory prostate cancer, resected high-risk soft tissue sarcoma, unresectable hepatocellular carcinoma, Walderstrom's macroglobulinemia, smoldering myeloma, indolent myeloma, fallopian tube cancer, androgen independent prostate cancer, androgen dependent stage IV non-metastatis prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In one embodiment, provided herein are methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another embodiment, provided herein are methods of treating, preventing or managing various types of lymphomas, including Non-Hodgkin's lymphoma (NHL). The term "lymphoma" refers to a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mental zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the disease and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent publication no. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, leutic neuropathy, and other painful neuropathic conditions such as those induced by drugs such as vineristine and velcade.

As used herein, the terms "complex regional pain syndrome," "CRPS" and "CRPS and related syndromes" means a chronic pain disorder characterized by one or more of the following: pain, whether spontaneous or evoked, including allodynnia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alterative in blood flow and hyperhidrosis) associated with trophic skin changes (hair and nail growth abnormalities and cutaneous ulceration).

Examples of MD and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. publication no. 2005/0214328A1, published Sep. 29, 2005, which is incorporated herein by reference. Specific examples include, but are not limited to, keratoses and related symptoms, skin diseases or disorders characterized with overgrowths of the epidermis, acne, and wrinkles.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or deratoma. The term "seborrheic keratosis" also refers to seborrheic wart, senile wart, or basal cell papilioma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carbinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trèlat, warty dyskeratoma (WD), trichostatis, spinulosa (TS), erythrokeratodermia variabilis (EKV), ichthyosis fetalis (harleqin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. publication no. 2005/0239842A1, published Oct. 27, 2005, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibroisis, anomalous pulmonary venous drainage, pulmonary venocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but are not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. publication no. 2006/0154880, published Jul. 13, 2006, which is incorporated herein by reference. Parasitic diseases include diseases and disorders caused by human intracellular parasites such as, but not limited to, *P. falcifarium, P. ovale, P. vivax, P. malariae, L. donavari, L. infantum, L. aethiopica, L. major, L. tropica, L. mexicana, L. braziliensis, T. Gondii, B. microti, B. divergens, B. coli, C. parvum, C. cayetanesis, E. histolytica, I. belli, S. mansonii, S. haematobium, Trypanosoma* ssp., *Toxoplasma* ssp., and *O. volvulus*. Other diseases are disorders caused by non-human intracellular parasites such as, but not limited to, *Babesia bovis, Babesia canis, Banesia Gibsoni, Besnoitia darlingi, Cytauxzoon felis, Eimerisia* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocereiasis, filariasis, schistosomiasis, and dermatitis caused by animal schistosomes.

Examples of immunodeficiency disorders include, but are not limited to, those described in U.S. publication no. 2006/0188475, published Aug. 24, 2006. Specific examples include, but not limited to, adenosine deaminase deficiency, antibody deficiency with normal or elevated Igs, ataxiatenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglogulinemia of infancy, Wistcott-Aldrich syndrome, X-linked agammaglogulinemia, X-linked severe combined immunodeficiency.

Examples of CNS disorders include, but are not limited to, those described in U.S. publication no. 2005/0143344, published Jun. 30, 2005, which is incorporated herein by reference. Specific examples include, but are not limited to, include, but are not limited to, Amyotrophic Lateral Sclerosis, Alzheimer disease, Parkinson Disease, Huntington's Disease, Multiple Sclerosis other neuroimmunological disorders such as Tourette Syndrome, delerium or disturbances in consciousness that occur over a short period of time, and amnestic disorder, or discreet memory impairments that occur in the absence of other central nervous system impairments.

Examples of CNS injuries and related syndromes include, but are not limited to, those described in U.S. publication no. 2006/012228, published Jun. 8, 2006, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other diseases or disorders include, but not limited to, viral, genetic, allergic, and autoimmune disease. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury.

Examples of atherosclerosis and related conditions include, but are not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated herein:

| Artery | Body Areas Supplied |
| --- | --- |
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |

| Artery | Body Areas Supplied |
| --- | --- |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |
| Splenic | Stomach, pancreas, and spleen |
| Subclavian | Shoulder |
| Superior mesenteric | Pancreas, small intestine, ascending and transverse colon |
| Testicular | Testes |
| Ulnar | Forearm |

Examples of dysfunctional sleep and related syndromes include, but are not limited to, those disclosed in U.S. publication no. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, muscoloskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral schlerosis, multiple sclerosis, Huntington's Disease, bradykinesia; muscle rigidity; parkinsonian tremor; parkinsonian gait; motion freezing; depression; defective long-term memory; Rubinstein-Taybi syndrome (RTS); dementia; postural instability; hypokinetic disorders; synuclein disorders; multiple system atrophies; stiatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophia Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis, psoriatic arthritis and other arthritic conditions, septic shock, sepsis, endotoxic shock, graft versus host disease, wasting, Crohn's disease, ulcerative colitis, multiple sclerosis, systemic lupus erythromatosis, ENL in leprosy, HIV, AIDS, and opportunistic injections in AIDS; disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatisis.

In other embodiments, the use of compounds provided herein in various immunological applications, in particular, as vaccine adjuvants, particularly anticancer vaccine adjuvants, as disclosed in U.S. Publication No. 2007/0048327, published Mar. 1, 2007, which is incorporated herein in its entirety by reference, is also encompassed. These embodiments also relate to the uses of compounds provided herein in combination with vaccines to treat or prevent cancer or infectious diseases, and other various uses of immunomodulatory compounds such as reduction or desensitization of allergic reactions.

Doses of a compound provided herein, or a pharmaceutically acceptable salt, solvate, clathrate, stereoisomer or prodrug thereof, vary depending on factors such as: specific indication to be treated, prevented, or managed; age and condition of a patient; and amount of second active agent used, if any. Generally, a compound provided herein, or a pharmaceutically acceptable salt, solvate, clathrate, stereoisomer or prodrug thereof, may be used in an amount of from about 0.1 mg to about 500 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

4.3 Second Active Agents

A compound provided herein, or a pharmaceutically acceptable salt, solvate, prodrug, clathrate, or stereoisomer thereof, can be combined with other pharmacologically active compounds ("second active agents") in methods and compositions provided herein. Certain combinations may work synergistically in the treatment of particular types diseases or disorders, and conditions and symptoms associated with such diseases or disorders. A compound provided herein, or a pharmaceutically acceptable salt, solate, clathrate, stereoisomer or prodrug thereof, can also work to alleviate adverse effects associated with certain second active agents, and vice versa.

One or more second active ingredients or agents can be used in the methods and compositions provided herein.

Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransferase inhibitors; IkB kinase inhibitors; p38MAPK inhibitors; EGFR inhibitors (such as, for example, gefitinib and erlotimib HCL); HER-2 antibodies (such as, for example, trastuzumab (Herceptin®) and pertuzumab (Omnitarg™)); VEGFR antibodies (such as, for example, bevacizumab (Avastin™); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

Specific second active compounds that can be combined with compounds provided herein vary depending on the specific indication to be treated, prevented or managed.

For instance, for the treatment, prevention or management of cancer, second active agents include, but are not limited to: semaxanib; cyclosporin; etanercept; doxycycline; boriezomib; acivicin; aclarubicin; acodazole hydrochloride; acronine; adozelesin; adesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithing hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretidine; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxanthrone hydrochloride; masoprocol; maytansine; menogaril; mercaptopurine; methotrexate; methotrexate sodium; metoprine; meturedepa; mitindomide; mitocarcin; mitocromin; mitogillin; metomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucoronate; triplorelin; tubulozole hydrochloride; uracil mustard; uredepa; vapreotide; verteporfin; vinblastine sulfate; vincristine sulfate; vindesine; vindesine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminoevulinic acid; amrubicin; amsacrine; anagrelide; anastrozole; andrographolide; angiogenesis inhibitors; antagonist D; antagonist G; antarclix; anti-dorsalizing morphogenetic protein-1; antiandrogen, prostatic carbinoma; antiestrogen; antineoplaston; antisense aligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baecatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutimide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; cytostatin; dacliximab; decitabine; dehydrodidemnun B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithing; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic cid; idarubicin; idoxifene; idramantone; ilmofosine; isomastat; imatinib (Gleevec®), imiquimod; immunostimulant peptides; insulin-like growth factor-1 receptor inhibitor, interferon agonists; interferons; interleukins;

iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombrieine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostin; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizaxin; pamidronic acid; panaxytriol; panomifene; parabactin; pazelliptine; pegaspargase; peldesine; pentosan polysulfate sodium; pentastatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostagladin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R11 retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; somermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsoline; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonists; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropiscetron; turosteride; tyrosine kinase inhibitors; tyrphostine; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etopside, cyclophosphamide; temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphorphonate, arsenic trioxide, vincristine, doxorubicin (Doxil®), paclitaxel, ganciclovir, adriamycin, estramustine sodium phosphate (Emcyt®), sulindac, and etoposide.

In another embodiment, examples of specific second agents according to the indications to be treated, prevented, or managed can be found in the following references, all of which are incorporated herein in their entireties: U.S. Pat. Nos. 6,281,230 and 5,635,517; and U.S. publication nos. 2004/0220144, 2004/0190609, 2004/0087546, 2005/0203142, 2004/0091455, 2005/0100529, 2005/0214328, 2005/0239842, 2006/0154880, 2006/0188475, 2006/012228, and 2005/0143344.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicyclic acid acetate (Aspirin®), celecoxib (Celebrex®), Enbrel®, ketamine, gabapentin (Neurontin®), phenytoin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphehydramide guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), setraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazipines, baclofen, tizanidine and phenoxybenzamine.

Examples of second active agents that may be used for the treatment, prevention and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangliogenesis compound, or a combination thereof. Specific examples include, but are not limited to, verteporfin, purlytin, an angiostatic steroid, rhuFab, interferon-2α, pentoxifylline, tin etiopurpurin, motexafin, lucentis, lutetium, 9-fluoro-11,21-dihydroxy-16, 17-1-methylethylidinebis(oxy)pregna-1,4-diene-3,20-dione, latanoprost (see U.S. Pat. No. 6,225,348), tetracycline and its derivatives, rifamycin and its derivatives, macrolides, metromidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment, prevention and/or management of skin diseases include, but are not limited to, keratolytics, retinoids, α-hydroxy, acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogegn, AlloDerm, Fascia, Cymetra, Autologen, Zyderm, Zyplast, Resoplast, and Isolagen.

Examples of second active agents that may be used for the treatment, prevention and/or management of pulmonary hepertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostagladin 12 (PG12), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesarian (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, gleomycin, hyaluronidase, nitomycin C, mepacrine, thiotepa, tetracycline and gemeitabine.

Examples of second active agents that may be used for the treatment, prevention and/or management of parasitic diseases include, but are not limited to, chloroquine, quinine, quinidine, pyrimethamine, sulfadiazine, doxycycline, elindamycin, mefloquine, halofantrine, primaquine, hydroxychloroquine, proguanil, atovaquone, azithromycin, suramine, pentamidine, melarsoprol, nifurtimox, benznidazole, amphotericin B, pentavalent antimony compounds (e.g., sodium stiboglucuronate), interferon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglubulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemel CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physotigmine sulfate, physotigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, idflunisal, etodolac, meloxicam, ibuprofen, ketoprofen, nabumetone, refecoxib, methotrexate, leflunomide, sulfasalazine, gold salts, Rho-D Immune Glubulin, mycophenylate mofetil, cyclosporine, azathioprine, tacrolimus, basiliximab, daclizumab, salicyclic acid, acetylsalicylic acid, methyl salicyclate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiropyrine, apazone, zileuton, aurothioglucose, gold sodium thiomalate, auranofin, methotrexate, colchicine, alopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolastetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicyclic acid, acetylsalicyclic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises l-threo-methylphidate, d-threo-methylphenidate, dl-threo-methylphenidate, l-erythro-methylphenidate, d-erythro-methylphenidate, dl-erythro-methylphnidate; and a mixture thereof; and a diuretic agent such as, but not limited to, mannitol, furosenmide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventioal agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine salicylate, physotigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicyclic acid, methyl salicyclate, diflunisal, salsalate, olsalazine, sulfasalazine, acetaminophen, indomethacin, sulidac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchine, allopurinol, probenecid, sulfinpyrazone, benzbromarone, betamethasone and other glucocorticoids, metoclopormide, domperidone, prochlorperazine, promethazine, chlopromazine, trimethobenzamide, ondansetron, granisetron, hydroxyzine, acetylieucine monoethanolamine, alizapride, azasetron, benzquinamide, bietanautine, bromopride, bucliziine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, triethylperazine, thioproperazine, tropisetron, and a mixture thereof.

Examples of second active agents that may be used for the treatment, prevention and/or management of hemoglubinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alpha-n1, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonits such as clotrimazole and triaryl methane derivatives; Deferoxamine; protein C; and transfusions of blood, or of a blood substitute such as Hemospan™ or Hemospan™ PS (Sangart).

Administration of a compound provided herein, or a pharmaceutically acceptable salt, solvate, clathrate, stereoisomer or prodrug thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for compounds provided herein is oral. Routes of administration for the second active agents or ingredients are known to those of ordinary skill in the art. See, e.g., *Physician's Desk Reference* (60$^{th}$ ed., 2006).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

4.4 Cycling Therapy

In certain embodiments, the prophylactic or therapeutic agents provided herein are cyclically administered to a patient. Cycling therapy involves the administration of an active agent for a period of time, followed by rest (i.e., discontinuation of the administration) for a period of time, and repeating the sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.1 mg to about 500 mg per day, followed by a rest of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

4.5 Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed in Section 4.3, above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets, caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic properations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences,* 18th ed., Mack Publishing, Easton, Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specified active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of stimulating long-term storage in order to determine characteristics such as shelf-life or the stability of formulations over time. See, e.g., Jens T. Carstensen, *Drug Stability: Principles & Practices,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

4.5.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaoline, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used in form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co., of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

4.5.2 Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,074,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.5.3 Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patient' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection; Dextrose and Sodium Chloride Injection, and Lactated Ringer's Injection; water-miscible vehicles such as, but not limited to, ethyl alcohol, polyethylene glycol and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

4.5.4 Topical and Musocal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompasses herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. 1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4.6 Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise additional ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see e.g., section 4.3).

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples.

5.1 3-(2,6-dimethyl-4-oxo-4H-quinazolin-3-yl)-piperidine-2,6-dione

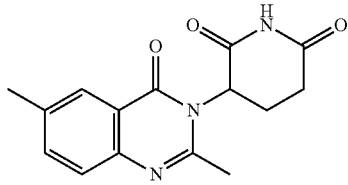 [SMILES: Cc1ccc2nc(C)n(C3CCC(=O)NC3=O)c(=O)c2c1]

To a stirred mixture of 2-amino-5-methylbenzoic acid (4.8 mg, 32 mmol) and imidazole (2.6 g, 38 mmol) in acetonitrile (100 mL), was added acetyl chloride (2.7 mL, 38 mmol) at room temperature. The mixture was stirred at room temperature overnight. To the mixture, was added 3-amino-piperidine-2,6-dione hydrogen chloride (5.2 g, 32 mmol), imidazole (4.7 g, 70 mmol) and triphenyl phosphite (9.9 mL, 38 mmol) and heated to reflux for 22 hours. To the mixture, was added water (100 mL). The suspension was filtered and washed with water (2×100 mL), ethyl acetate (2×100 mL), sodium hydrogen carbonate (sat, 100 mL) and water (100 mL) to give a white solid, which was stirred in DMF (40 mL) overnight. The suspension was filtered and washed with DMF (5 mL) to give a white solid. The solid was stirred in water (100 mL) at 60° C. for 2 hours, then at room temperature overnight. The suspension was filtered and washed with water (2×50 mL) to give 3-(2,6-dimethyl-4-oxo-4H-quinazolin-3-yl)-piperidine-2,6-dione as a white solid (3.4 g, 38% yield): HPLC: Waters Symmetry $C_{18}$, 5 µm, 3.9×150 mm, 1 mL/min, 240 nm, 20/80 $CH_3CN/0.1\%$ $H_3PO_4$, 5.37 min (99.8%); mp: 270-272° C.; $^1H$ NMR (DMSO-$d_6$) δ 2.10-2.22 (m, 1H, CHH), 2.43 (s, 3H, $CH_3$), 2.56-2.72 (m, 5H, $CH_3$2CHH), 2.76-2.92 (m, 1H, CHH), 5.24 (dd, J=6, 11 Hz, 1H, NCH), 7.52 (d, J=8 Hz, 1H, Ar), 7.64 (dd, J=2, 8 Hz, 1H, Ar), 7.82 (s, 1H, Ar), 11.02 (s, 1H, NH); $^{13}C$ NMR (DMSO-$d_6$) δ 20.76, 20.95, 23.34, 30.60, 56.47, 120.05, 125.20, 126.39, 135.96, 136.19, 144.87, 153.99, 160.40, 169.53, 172.62; LCMS: MH=286 Anal Calcd for $C_{15}H_{15}N_3O_1$+2 $H_2O$: C, 56.07; H, 5.96; N, 13.03, Found: C, 55.73; H, 5.75; N, 13.01.

5.2 2-benzyloxy-N-[3-(2,6-dioxo-piperidinin-3-yl)-2-methyl-4-oxo-3,4-dihydro-quinazolin-6-yl]-acetamide

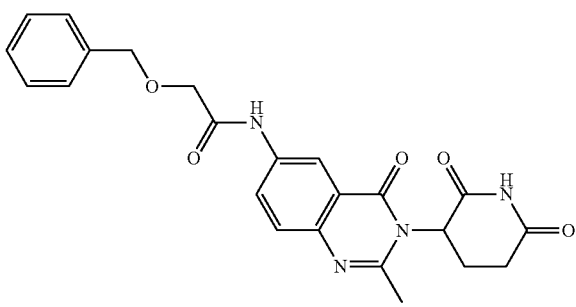 [SMILES: Cc1nc2ccc(NC(=O)COCc3ccccc3)cc2c(=O)n1C1CCC(=O)NC1=O]

Step 1: To a stirred mixture of 5-amino-isatoic anhydride (1.0 g, 5.6 mmol) and triethyl amine (0.8 mL, 9.0 mmol) in acetonitrile (15 mL), was added benzyloxyacetyl chloride (0.87 mL, 5.6 mmol) dropwise at room temperature. The mixture was kept at room temperature overnight. To the mixture, was added triethylamine (3.1 mL, 22 mmol), 3-amino-piperidine-2,6-dione hydrogen chloride (0.92 g, 5.6 mmol), and acetic acid (3.2 mL, 56 mmol). The mixture was heated at 80° C. for 8 hours. To the mixture, was added water (75 mL). The suspension was filtered and washed with water (75 mL) and ethyl acetate (75 mL) to give a dark solid, which was purified with column chromatography (Silica Gel, methanol/methylene chloride 0% to 10% in 15 min) to give 2-amino-5-(2-benzyloxy-acetylamino)-N-(2,6-dioxo-piperidin-3-yl)-benzamide as a white solid (0.28 g, 12% yield): $^1$H NMR (DMSO-d$_6$) δ 1.92-2.18 (m, 2H, 2CHH), 2.50-2.55 (m, 1H, CHH), 2.72-2.84 (m, 1H, CHH), 4.03 (s, 2H, CH$_2$), 4.61 (s, 2H, CH$_2$), 4.68-4.77 (m, 1H, NCH), 6.19 (br, 2H, NH$_2$), 6.68 (d, J=9 Hz, 1H, Ar), 7.30-7.42 (m, 6H, Ar), 7.62 (d, J=2 Hz, 1H, Ar), 8.43 (d, J=8 Hz, 1H, NH), 9.44 (s, 1H, NH), 10.84 (s, 1H, NH); $^{13}$C NMR (DMSO-d$_6$) δ 24.09, 30.96, 49.12, 69.37, 72.35, 114.27, 116.23, 121.11, 125.99, 126.13, 127.77, 128.27, 137.68, 146.19, 167.28, 168.36, 172.35, 173.01.

Step 2: A solution of 2-amino-5-(2-benzyloxy-acetylamino)-N-(2,6-dioxo-piperidin-3-yl)-benzamide (0.26 g, 0.6 mmol) and trimethyl orthoformate (2 mL) and p-toluene sulfonic acid (60 mg) in acetonitrile (10 mL) was heated to reflux for 21 hours. To the mixture, was added water (25 mL) and ether (25 mL). The suspension was filtered and washed with water (50 mL) and ethyl acetate (50 mL) to give 2-benzyloxy-N-[3-(2,6-dioxo-piperidin-3-yl)-2-methyl-4-oxo-3,4-dihydro-quinazolin-6-yl]-acetamide as a white solid (180 mg, 72% yield): HPLC: Waters Symmetry C$_{18}$, 5 μm, 3.9×150 mm, 1 mL/min, 240 nm, 40/60 CH$_3$CN/0.1% H$_3$PO$_4$, 2.87 min (99.3%); mp: 248-250° C.; $^1$H NMR (DMSO-d$_6$) δ 2.14-2.16 (m, 1H, CHH), 2.61-2.87 (m, 3H, CH$_2$, CHH), 4.15 (s, 2H, CH$_2$), 4.64 (s, 2H, CH$_2$), 5.49-5.50 (m, 1H, NCH), 7.31-7.41 (m, 5H, Ar), 7.68 (d, J=9 Hz, 1H, Ar), 8.06-8.10 (m, 1H, NH), 8.28 (s, 1H, CH), 8.55 (br, 1H, Ar), 10.24 (s, 1H, NH), 11.16 (s, 1H, NH); $^{13}$C NMR (DMSO-d$_6$) δ 23.05, 31.48, 58 (br), 69.87, 72.92, 115.69, 122.15, 127.30, 128.16, 128.28, 128.34, 128.77, 137.98, 138.14, 144.06, 146.48, 160.10, 168.93, 170.43, 172.90; LCMS; MH=421; Anal Calcd for C$_{22}$H$_{20}$N$_4$O$_5$: C, 62.85; H, 4.79; N, 13.33. Found: C, 60.60; H, 4.29; N, 12.54.

5.3 3-(6-fluoro-2-methyl-4-oxo-4H-quinazolin-3-yl) piperidine-2,6-dione

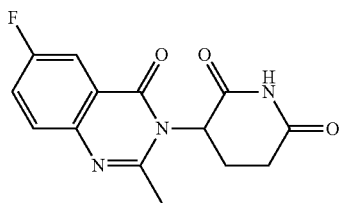 [SMILES: Cc1nc2ccc(F)cc2c(=O)n1C1CCC(=O)NC1=O]

To a stirred mixture of 2-amino-5-fluorobenzoic acid (1.2 g, 7.8 mmol) and imidazole (0.63 g, 9.3 mmol) in acetonitrile (15 mL), was added acetyl chloride (0.66 mL, 9.3 mmol) at room temperature. The mixture was stirred at room temperature overnight. To the mixture, was added 3-amino-piperidine-2,6-dione hydrogen chloride (1.3 g, 7.7 mmol), imidazole (1.2 g, 17 mmol) and triphenyl phosphite (2.2 mL, 8.5 mmol) and heated to reflux for 22 hours. The suspension was filtered and washed with water (2×50 mL), ethyl acetate (2×50 mL), and water (50 mL) to give 3-(6-fluoro-2-methyl-4-oxo-4H-quinazolin-3-yl)-piperidine-2,6-dione as a white solid (1.2 g, 53% yield): HPLC: Waters Symmetry C$_{18}$, 5 μm, 3.9×150 mm, 1 mL/min, 240 nm, 20/80 CH$_3$CN/0.1% H$_3$PO$_4$, 5.99 min (99.3%); mp: 273-275° C.; $^1$H NMR (DMSO-d$_6$) δ 2.13-2.23 (m, 1H, CHH), 2.57-2.71 (m, 5H, CH$_3$, 2CHH), 2.75-2.95 (m, 1H, CHH), 5.30 (dd, J=6, 11 Hz, 1H, NCH), 7.70-7.73 (m, 3H, Ar), 11.06 (s, 1H, NH); $^{13}$C NMR (DMSO-d$_6$) δ 20.82, 23.31, 30.58, 56.63, 110.54 (d, J$_{C-F}$=23 Hz), 121.40 (d, J$_{C-F}$=8 Hz), 123.24 (d, J$_{C-F}$=24 Hz), 129.47 (d, J$_{C-F}$=8 Hz), 143.75, 154.45, 159.83 (d, J$_{C-F}$=245 Hz), 159.86 (d, J$_{C-F}$=3 Hz), 169.37, 172.58; LCMS: MH=290; Anal Calcd for C$_{14}$H$_{12}$N$_3$O$_3$F+1.3 H$_2$O: C, 53.78; H, 4.71; N, 13.44. Found: C, 53.75; H, 4.61; N, 13.50.

5.4 3-(6-chloro-2-methyl-4-oxo-4H-quinazolin-3-yl)-piperidine-2,6-dione

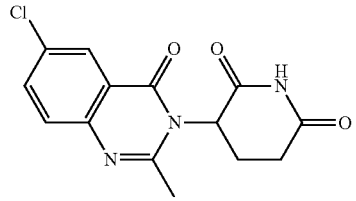

To a stirred mixture of 2-amino-5-chlorobenzoic acid (2.0 g, 12 mmol) and imidazole (1.0 g, 14 mmol) in acetonitrile (30 mL), was added acetyl chloride (1.0 mL, 14 mmol) at room temperature. The mixture was stirred at room temperature overnight. To the mixture, was added 3-amino-piperidine-2,6-dione hydrogen chloride (1.9 g, 12 mmol), imidazole (1.8 g, 26 mmol) and triphenyl phosphite (3.7 mL, 26 mmol) and heated to reflux for 22 hours. To the mixture, was added water (60 mL). The suspension was filtered and washed with water (2×50 mL), ethyl acetate (2×50 mL), and water (50 mL) to give 3-(6-chloro-2-methyl-4-oxo-4H-quinazolin-3-yl)-piperidine-2,6-dione as a white solid (2.9 g, 80% yield): HPLC: Waters Symmetry C$_{18}$, 5 μm, 3.9×150 mm, 1 mL/min, 240 nm, 25/75 CH$_3$CN/0.1% H$_3$PO$_4$, 6.65 min (98.5%); mp: 276-278° C.; $^1$H NMR (DMSO-d$_6$) δ 2.15-2.24 (m, 1H, CHH), 2.58-2.71 (m, 5H, CH$_3$, 2CHH), 2.78-2.92 (m, 1H, CHH), 5.30 (dd, J=6, 11 Hz, 1H, NCH), 7.66 (d, J=9 Hz, 2H, Ar), 7.85 (dd, J=3, 9 Hz, 1H, Ar), 7.98 (d, J=2 Hz, 1H, Ar), 11.06 (s, 1H, NH); $^{13}$C NMR (DMSO-d$_6$) δ 20.79, 23.45, 30.57, 56.71, 121.47, 124.89, 128.89, 130.77, 134.87, 145.57, 155.67, 159.53, 169.31, 172.56; LCMS: MH=306, 308; Anal Calcd for C$_{14}$H$_{19}$N$_3$O$_3$Cl+ 2H$_2$O: C, 49.20; H, 4.72; N, 12.30; Cl, 10.37. Found: C, 49.34; H, 4.57; N, 12.20; Cl, 10.39.

5.5 3-(6-bromo-2-methyl-4-oxo-4H-quinazolin-3-yl)-piperidine-2,6-dione

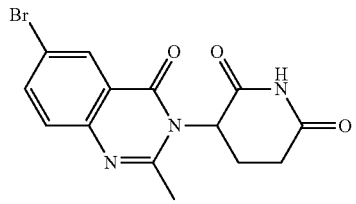 [SMILES: Cc1nc2ccc(Cl)cc2c(=O)n1C1CCC(=O)NC1=O]

Step 1: A stirred mixture of 5-bromo-isatoic anhydride (6.0 g, 25 mmol), 3-amino-piperidine-2,6-dione hydrogen chloride (4.1 g, 25 mmol), triethylamine (18 mL, 129 mmol), and acetic acid (15 mL, 262 mmol) in acetonitrile (60 mL) was heated at 90° C. for 18 hours. The suspension was filtered and washed with acetonitrile (2×80 mL), water (2×80 mL) and ethyl acetate (2×80 mL) to give 2-amino-N-(2,6-dioxo-piperidin-3-yl)-5-bromo-benzamide as a white solid (5.8 g, 72% yield): LCMS: MH=326, 328. The sample was used in the next step without further purification.

Step 2: A solution of 2-amino-N-(2,6-dioxo-piperidin-3-yl)-5-bromo-benzamide (1.0 g, 3 mmol) and trimethyl orthoacetate (1.6 mL) and p-toluene sulfonic acid (250 mg) in acetonotrile (10 mL) was heated to reflux for 7 days. The suspension was filtered and washed with ethyl acetate (10 mL), methanol (5 mL) and ethyl acetate (10 mL) to give 3-(6-bromo-4-oxo-4H-quinazolin-3-yl)-piperidine-2,6-dione as an off-white solid (108 mg, 10% yield): HPLC: Waters Symmetry $C_{18}$, 5 μm, 3.9×150 mm, 1 mL/min, 240 nm, 30/70 $CH_3CN/0.1\%$ $H_3PO_4$, 5.17 min (98.7%); mp: 273-275° C.; $^1H$ NMR (DMSO-$d_6$) δ 2.14-2.27 (m, 1H, CHH), 2.56-2.69 (m, 2H, 2CHH), 2.64 (s, 3H, $CH_3$), 2.72-2.90 (m, 1H, CHH), 5.29 (dd, J=6, 11 Hz, 1H, NCH), 7.58 (d, J=9 Hz, 1H, Ar), 7.98 (dd, J=2, 9 Hz, 1H, Ar), 8.12 (d, J=2 Hz, 1H, Ar), 11.06 (s, 1H, NH); $^{13}C$ NMR (DMSO-$d_6$) δ 20.72, 23.42, 30.50, 56.64, 118.80, 121.77, 127.94, 128.95, 137.51, 145.76, 155.74, 159.32, 167.24, 172.49; LCMS: MH=350, 352; Anal Calcd for $C_{14}H_{12}N_3O_3Br$: C, 48.02; H, 3.45; N, 12.00. Found: C, 48.02; H, 3.18; N, 11.76.

5.6 3-(6-hydroxy-2-methyl-4-oxo-4H-quinazolin-3-yl)-piperidine-2,6-dione

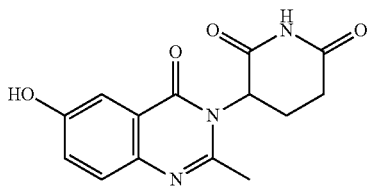 [SMILES: Cc1nc2ccc(O)cc2c(=O)n1C1CCC(=O)NC1=O]

To a stirred mixture of 2-amino-5-hydroxybenzoic acid (5.1 g, 33 mmol) and imidazole (5.0 g, 73 mmol) in acetonitrile (60 mL), was added acetyl chloride (5.2 mL, 73 mmol) at room temperature. The mixture was stirred at room temperature overnight. To the mixture, was added 3-amino-piperidine-2,6-dione hydrogen chloride (6.0 g, 37 mmol), imidazole (5.0 g, 73 mmol) and triphenyl phosphite (10.5 mL, 40 mmol) and heated to reflux for 22 hours. To the mixture, was added water (100 mL) and conc HCl until pH~1. The solvent was removed in vacuo. To the residue, was added water (50 mL). The aqueous layer was extracted with ethyl acetate (50 mL). To the aqueous layer, was added ethyl acetate (50 mL), and the mixture was stirred at room temperature to give a suspension. The suspension was filtered to give a solid, which was stirred in methanol (50 mL) overnight. The suspension was filtered and washed with methanol (2×30 mL) and water to give 3-(6-hydroxy-2-methyl-4-oxo-4H-quinazolin-3-yl)-piperidine-2,6-dione as an off-white solid (2.97 g, 31% yield): HPLC: Waters Symmetry $C_{18}$, 5 μm, 3.9×150 mm, 1 mL/min. 240 nm, 5/95 grad 95/5 in 5 min $CH_3CN/0.1\%$ $H_3PO_4$, 4.50 min (96.8%); mp: 315-317° C.; $^1H$ NMR (DMSO-$d_6$) δ 2.13-2.18 (m, 1H, CHH), 2.58 (s, 3H, $CH_3$), 2.62-2.71 (m, 2H, 2CHH), 2.78-2.91 (m, 1H, CHH), 5.22 (dd, J=6, 11 Hz, 1H, NCH), 7.24-7.32 (m, 2H, Ar), 7.49 (d, J=9 Hz, 1H, Ar), 10.07 (s, 1H, OH), 11.00 (s, 1H, NH); $^{13}C$ NMR (DMSO-$d_6$) δ 20.97, 23.10, 30.59, 56.36, 108.59, 121.24, 124.13, 128.19, 140.14, 151.39, 155.89, 160.24, 169.58, 172.63; LCMS: MH=288; Anal Calcd for $C_{14}H_{13}N_3O_4+1$ $H_2O$: C, 55.08; H, 4.95; N, 13.76. Found: C, 54.82; H, 4.74; N, 13.54.

5.7 3-(6-chloro-4-oxo-4H-quinazolin-3-yl)-piperidine-2,6-dione

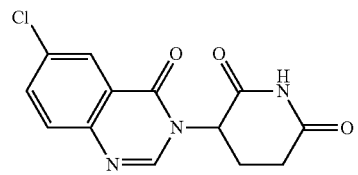

Step 1: A stirred mixture of 5-chloroisatoic anhydride (0.51 g, 2.5 mmol), 3-amino-piperidine-2,6-dione hydrogen chloride (0.42 g, 2.5 mmol), triethylamine (1.8 mL, 12.7 mmol), and acetic acid (1.5 mL, 25.3 mmol) in acetonitrile (5 mL) was heated at 150° C. in a microwave oven for 5 minutes. The suspension was filtered and washed with water (50 mL) and ethyl acetate (20 mL) to give 2-amino-N-(2,6-dioxo-piperidin-3-yl)-5-chloro-benzamide as a white solid (0.31 g, 42% yield): $^1H$ NMR (DMSO-$d_6$) δ 1.91-2.12 (m, 2H, 2CHH), 2.50-2.56 (m, 1H, CHH), 2.72-2.80 M, 1H, CHH), 4.71-4.76 (m, 1H, NCH), 6.58 (brs, 2H, $NH_2$), 6.74 (d, J=8 Hz, 1H, Ar), 7.19 (dd, J=2, 9 Hz, 1H, Ar), 7.58 (t; J=2 Hz, 1H, Ar), 8.62 (d, J=8 Hz, 1H, NH), 10.86 (s, 1H, NH); $^{13}C$ NMR (DMSO-$d_6$) δ 23.99, 30.89, 49.00, 114.62, 117.60, 118.04, 127.25, 131.63, 148.61, 167.37, 172.20, 172.93; LCMS: MH=282, 284.

Step 2: A solution of 2-amino-N-(2,6-dioxo-piperidin-3-yl)-5-chloro-benzamide (0.31 g, 1.1 mmol) and trimethyl orthoformate (4 mL) and p-toluene sulfonic acid (50 mg) was heated to 150° C. in a microwave oven for 10 minutes. The suspension was filtered and washed with ethyl acetate (10 mL), methanol (5 mL) and ethyl acetate (10 mL) to give 3-(6-chloro-4-oxo-4H-quinazolin-3-yl)-piperidine-2,6-dione as a white solid (230 mg, 74% yield): HPLC: Waters Symmetry $C_{18}$, 5 μm, 3.9×150 mm, 1 mL/min, 240 nm, 30/70 $CH_3CN/0.1\%$ $H_3PO_4$, 4.01 min (100%); mp: 302-305° C.; $^1H$ NMR (DMSO-$d_6$) δ 2.13-2.20 (m, 1H, CHH), 2.62-2.93 (m, 3H, $CH_2$, CHH), 5.52 (br, 1H, NCH), 7.76 (d, J=9 Hz, 1H, Ar), 7.91 (dd, J=2, 9 Hz, 1H, Ar), 8.10 (d, J=2 Hz, 1H, Ar), 8.41 (s, 1H, CH), 11.19 (s, 1H, NH); $^{13}C$ NMR (DMSO-$d_6$) δ 22.39, 30.87, 56.29 (br), 122.56, 125.05, 129.47, 131.59, 134.82, 146.19, 147.75, 158.73, 169.68, 172.39; LCMS: MH=292, 294; Anal Calcd for $C_{13}H_{10}N_3O_3Cl$: C, 53.53; H, 3.46; N, 14.41. Found: C, 53.43; H, 3.21; N, 14.27.

5.8 3-(6-bromo-4-oxo-4H-quinazolin-3-yl)-piperidine-2,6-dione

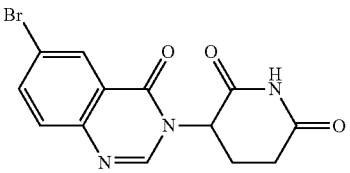 [SMILES: O=C1CCC(n2cnc3ccc(Cl)cc3c2=O)C(=O)N1]

Step 1: A stirred mixture of 5-bormo-isatoic anhydride (6.0 g, 25 mmol), 3-amino-piperidine-2,6-dione hydrogen chloride (4.1 g, 25 mmol), triethylamine (18 mL, 129 mmol), and acetic acid (15 mL, 262 mmol) in acetonitrile (60 mL) was heated at 90° C. for 18 hours. The suspension was filtered and washed with acetonitrile (2×80 mL), water (2×80 mL) and ethyl acetate (2×80 mL) to give 2-amino-N-(2,6-dioxo-piperidin-3-yl)-5-bromo-benzamide as a white solid (5.8 g, 72% yield): LCMS: MH=326, 328. The sample was used in the next step without further purification.

Step 2: A solution of 2-amino-N-(2,6-dioxo-piperidin-3-yl)-5-bromo-benzamide (0.51 g, 1.5 mmol) and trimethyl orthoformate (2 mL) and p-toluene sulfonic acid (150 mg) in acetonitrile (10 mL) was heated to reflux for 12 hours. To the mixture, was added water (70 mL), and stirred at room temperature for 2 hours. The suspension was filtered and washed with ethyl acetate (10 mL). The solid in NMP (3 mL) was heated at 80° C. To the solution, was added water (1.5 mL), and the mixture was allowed to cool to room temperature. The suspension was filtered and washed with NMP (1 mL) and ethyl acetate (10 mL) to give 3-(6-bromo-4-oxo-4H-quinazolin-3-yl)-piperidine-2,6-dione as a white solid (350 mg, 68% yield): HPLC: Waters Symmetry $C_{18}$, 5 μm, 3.9×150 mm, 1 mL/min, 240 nm, 30/70 $CH_3CN$/0.1% $H_3PO_4$, 4.18 min (99.9%); mp: 312-314° C.; $^1$H NMR (DMSO-$d_6$) δ 2.14-2.21 (m, 1H, CHH), 2.60-2.74 (m, 2H, 2CHH), 2.83-2.93 (m, 1H, CHH), 5.51 (brs, 1H, NCH), 7.68 (d, J=9 Hz, 1H, Ar), 8.03 (dd, J=2, 9 Hz, 1H, Ar), 8.24 (d, J=2 Hz, 1H, Ar), 8.42 (s, 1H, CH), 11.19 (s, 1H, NH); $^{13}$C NMR (DMSO-$d_6$) δ 22.45, 30.93, 55.49, 119.83, 122.96, 128.23, 129.65, 137.61, 146.52, 147.94, 158.66, 169.75, 172.46: LCMS: MH=336, 338; Anal Calcd for $C_{13}H_{10}N_3O_3Br$+0.3 $H_2O$: C, 45.72; H, 3.13; N, 12.30; Br, 23.39; Found: C, 45.46; H, 2.75; N, 12.15; Br, 22.81.

5.9 3-(6-methyl-4-oxo-4H-quinazolin-3-yl)-piperidine-2,6-dione

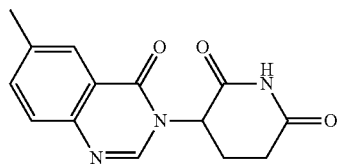 [SMILES: Cc1ccc2ncn(C3CCC(=O)NC3=O)c(=O)c2c1]

Step 1: A mixture of 2-amino-5-methylbenzoic acid (1.0 g, 6.6 mmol) and CDI (1.0 g, 6.1 mmol) in acetonitrile (15 mL) was stirred at room temperature for 1.5 hours. To the suspension, was added 3-amino-piperidine-2,6-dione hydrogen chloride (1.0 g, 6.1 mmol) and sodium hydrogen carbonate (0.45 g, 3.6 mmol), and the mixture was heated at 50° C. for 21 hours. The suspension was cooled to room temperature for 1 hour. The suspension was filtered and washed with acetonitrile (20 mL), water (2×20 mL) and ethyl acetate (20 mL) to give 2-amino-N-(2,6-dioxo-piperidin-3-yl)-5-methyl-benzamide as a blue solid (1.1 g, 63% yield): $^1$H NMR (DMSO-$d_6$) δ 1.91-1.98 (m, 1H, CHH), 2.05-2.14 (m, 1H, CHH), 2.17 (s, 3H, $CH_3$), 2.50-2.56 (m, 1H, CHH), 2.73-2.85 (m, 1H, CHH), 4.69-4.77 (m, 1H, NCH), 6.20 (br, 2H, $NH_2$), 6.63 (d, J=9 Hz, 1H, Ar), 7.00 (dd, J=2, 8 Hz, 1H, Ar), 7.34 (d, J=8 Hz, 1H, Ar), 8.43 (d, J=8 Hz, 1H, NH), 10.84 (s, 1H, NH); $^{13}$C NMR (DMSO-$d_6$) δ 19.89, 24.13, 30.92, 48.93, 113.87, 116.48, 122.81, 127.87, 132.72, 147.40, 168.55, 172.40, 172.97.

Step 2: A solution of 2-amino-N-(2,6-dioxo-piperidin-3-yl)-5-methyl-benzamide (0.45 g, 1.7 mmol) and trimethyl orthoformate (4 mL) and p-toluene sulfonic acid (80 mg) was heated to 160° C. in a microwave oven for 8 minutes. To the suspension, was added methanol (20 mL), methylene chloride (20 mL), and Celite (5 mL). The solvent was removed invacuo. The reside was placed in a SIM and was purified with column chromatography (Silica Gel, methanol/methylene chloride 0% gradient 10% in 15 min) to give as 3-(6-methyl-4-oxo-4H-quinazolin-3-yl)-piperidine-2,6-dione as a blue solid (50 mg, 9% yield): HPLC: Waters Symmetry $C_{18}$, 5 μm, 3.9×150 mm, 1 mL/min, 240 nm, 30/70 $CH_3CN$/0.1% $H_3PO_4$, 2.78 min (96.1%); mp: 285-287° C.; $^1$H NMR (DMSO-$d_6$) δ 2.11-2.18 (m, 1H, CHH), 2.46 (s, 3H, $CH_3$), 2.56-2.74 (m, 2H, 2CHH), 2.82-2.93 (m, 1H, CHH), 5.48 (br, 1H, NCH), 7.61 (d, J=8 Hz, 1H, Ar), 7.70 (dd, J=2, 8 Hz 1H, Ar), 7.94 (br, 1H, Ar), 8.33 (s, 1H, CH), 11.15 (s, 1H, NH); $^{13}$C NMR (DMSO-$d_6$) δ 20.72, 22.51, 30.91, 57.00 (br), 121.09, 125.38, 127.00, 135.89, 137.07, 145.46, 146.45, 159.60, 169.88, 172.44; LCMS: MH=272; Anal Calcd for $C_{14}H_{13}N_3O_3$: C, 61.99; H, 4.83; N, 15.49. Found: C, 61.78; H, 4.57; N, 15.34.

5.10 3-(6-amino-2-methyl-4-oxo-4H-quinazolin-3-yl)-piperidine-2,6-dione

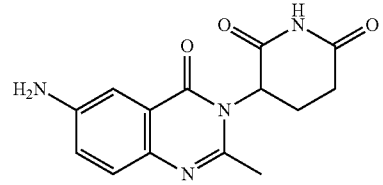 [SMILES: Cc1nc2ccc(N)cc2c(=O)n1C1CCC(=O)NC1=O]

Step 1: To a stirred mixture of 2-amino-5-nitrobenzoic acid (5.0 g, 28 mmol) and imidazole (2.2 g, 33 mmol) in acetonitrile (50 mL), was added acetyl chloride (2.3 mL, 33 mmol) at room temperature. The mixture was stirred at room temperature overnight. To the mixture, was added 3-amino-piperidine-2,6-dione hydrogen chloride (4.5 g, 28 mmol), imidazole (4.1 g, 60 mmol) and triphenyl phosphite (8.7 mL, 33 mmol) and heated to reflux for 22 hours. To the mixture, was added water (60 mL), and water (50 mL) to give 3-(2-methyl-6-nitro-4-oxo-4H-quinazolin-3-yl)-piperidine-2,6-dione as an off-white solid (5.3 g, 61% yield): $^1$H NMR (DMSO-$d_6$) δ 2.19-2.26 (m, 1H, CHH), 2.60-2.69 (m, 2H, 2CHH), 2.72 (s, 3H, $CH_3$), 2.79-2.87 (m, 1H, CHH), 5.36 (dd, J=5, 11 Hz, 1H, NCH), 7.83 (d, J=9 Hz, 1H, Ar), 8.56 (dd, J=3, 9 Hz, 1H, Ar), 8.74 (dt, J=3 Hz 1H, Ar), 11.12 (s, 1H, NH); $^{13}$C NMR (DMSO-$d_6$) δ 20.69, 23.82, 30.57, 56.98, 119.46, 120.20, 122.21, 128.45, 128.74, 144.90, 150.85, 159.13, 159.78, 169.12, 172.53.

Step 2: A suspension of 3-(2-methyl-6-nitro-4-oxo-4H-quinazolin-3-yl)-piperidine-2,6-dione (4.1 g, 13 mmol) and 20% Pd(OH)$_2$/C (0.9 g) in cyclohexene (20 mL) and DMF (60 mL) was heated in a 125° C. oil bath overnight. The suspension was filtered thru a pad of Celite, and washed with DMF (30 mL). The DMF solution and Charcoal (4 g) were stirred at room temperature for 5 hours. The suspension was filtered thru a pad of Celite. The solvent was removed in vacuo. To the residue, was added DMF (20 mL), and then water (80 mL) to give a suspension. The suspension was filtered and washed with water (50 mL), ethyl acetate (50 mL) and water (50 mL) to give a brown solid, which was purified with preparative HPLC (C18 5/95 for 2 minutes then gradient to 50/50 in 18 min CH$_3$CN/H$_2$O) to give 3-(6-amino-2-methyl-4-oxo-4H-quinazolin-3-yl)-piperidine-2,6-dione as a white solid (1.15 g, 31% yield): HPLC: Waters Xterra C$_{18}$, 5 μm, 3.9×150 mm, 1 mL/min, 240 nm, 10/90 CH$_3$CN/0.1% NH4HCO2, 5.31 min (99.8%); mp: 314-316° C.; $^1$H NMR (DMSO-d$_6$) δ 2.08-2.14 (m, 1H, CHH), 2.54 (s, 3H, CH$_3$), 2.55-2.67 (m, 2H, 2CHH), 2.75-2.90 (m, 1H, CHH), 5.16 (dd, J=5, 11 Hz, 1H, NCH), 5.59 (brs, 2H, NH$_2$), 7.04-7.08 (m, 2H, Ar), 7.31-7.34 (m, 1H, Ar), 10.97 (s, 1H, NH); $^{13}$C NMR (DMSO-d$_6$) δ 21.06, 22.96, 30.62, 56.22, 105.89, 121.34, 122.61, 127.35, 137.89, 147.63, 149.24, 160.39, 169.68, 172.66; LCMS: MH=287, Anal Calcd for C$_{14}$H$_{14}$N$_4$O$_3$+1 H$_2$O: C, 55.26; H, 3.30; N, 18.41. Found: C, 54.99; H, 5.22; N, 18.35.

5.11 [3-(2,6-dioxo-piperidine-3-yl)-2-methyl-4-oxo-3,4-dihydro-quinazolin-6-ylmethyl]-carbamic acid tert-butyl ester

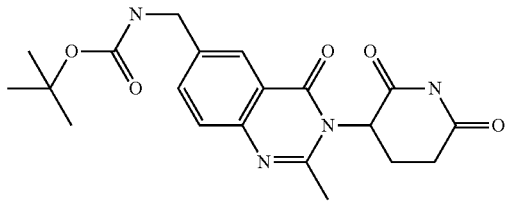 [SMILES: Cc1nc2ccc(CNC(=O)OC(C)(C)C)cc2c(=O)n1C1CCC(=O)NC1=O]

Step 1: A mixture of 5-methyl-2-nitro-benzoic acid methyl ester (93.35 g, 481.35 mmol), 1,3-dibromo-5,5-dimethylhydantoin (75.70 g, 264.74 mmol), in methyl acetate (550 mL) was heated at 78° C. for 40 minutes while stirred with a mechanical stirrer. Then a solution of 2,2'-azobisisobutyro-nitrile (3.95 g, 24.07 mmol) in methyl acetate (80 mL) was added, and the mixture was heated at about 75° C. for 13 hours. The mixture was allowed to cooled to 15° C. and stirred for 2 hours to age the precipitate. The suspension was filtered, washed with 10° C. methyl acetate (2×50 mL) to give a brown filtrate. To the filtrate, was added heptane (500 mL). The organic layer was washed with 2% brine (2×500 mL) and water (2×500 mL), and concentrated to about 2 volumes. To the mixture, was added t-butyl methyl ether (or MTBE, 300 mL). The mixture was heated at about 70° C. for 15 minutes, cooled to about 53° C. over one hour, seeded with the product (about 250 mg, or simply re-crystallized) at 45° C., then at 20-25° C., while blowing nitrogen with a glass pipette overnight. The resulting solid was filtered via a medium pore-sized funnel, washed with a pre-cooled 10° C. mixed solvent of heptane/MTBE (½ vol/vol) and suction dried in hood overnight to give 5-bromomethyl-2-nitro-benzoic acid method ester as an off-white solid (58.3 g, 44.0% yield). The solid was used in the next step without further purification.

Step 2: A stirred mixture of 5-bromomethyl-2-nitro-benzoic acid methyl ester (50.5 g, 184 mmol), di-tert-butyl iminodicarboxylate (40.15 g, 185 mmol), cesium carbonate (123.1 g, 3777.7 mmol), and lithium iodide (1.23 g, 9.21 mmol) in 2-butanone (556 mL) was heated to reflux in a 100° C. oil bath for 12 hours while stirred with a mechanical stirrer. The mixture was allowed to cool to room temperature. To the mixture, was added brine (300 mL), water (300 mL), and ethyl acetate (750 mL), and the mixture was stirred for 10 minutes. The suspension was filtered through a pad of Celite. The two layers were separated, and the organic layer was evaporated to a less volume. The aqueous layer was extracted with ethyl acetate (2×150 mL). The combined organic layers were washed with brine (500 mL), dried over magnesium sulfate while de-colored at the same time by charcoal at room temp with stirring for 30 minutes. The black mixture was filtered through a pad of Celite. The filtrate was evaporated to give 5-(di-tert-butoxycarbonylamino-methyl)-2-nitro-benzoic acid methyl ester as a brown oil (74.18 g, 98% yield). The product was used in the next step without further purification.

Step 3: To a stirred brown solution of 5-(di-tert-butoxycarbonylamino-methyl)-2-nitro-benzoic acid methyl ester (74.18 g, 180.7 mmol) in methylene chloride (700 mL) was added trifluoroacetic acid (26.2 mL, 352.4 mmol), and the mixture was stirred at room temp overnight. Sat. sodium bicarbonate (400 mL) was added to the solution, and the mixture was stirred for 10 m minutes. The organic layer was separated, dried over magnesium sulfate, and evaporated to give 5-(tert-botoxycarboylamino-methyl)-2-nitro-benzoic acid methyl ester as a brown oil (52.5 g, 94% crude yield). The product was used in the next step without purification.

Step 4: A mixture of 5-(tert-butoxycarbonylamino-methyl)-2-nitro-benzoic acid methyl ester (52.5 g, 169.3 mmol), lithium hydroxide (4.86 g, 203.1 mmol) in methanol (546 mL) and water (273 mL) was stirred with a mechanical stirrer at room temp overnight. The methanol was evaporated, and to the aqueous solution, was added 1 N HCl (270 mL) to form the precipitate. Ether (350 mL) was added, and the mixture was stirred at 0° C. for 2 hours. The mixture was evaporated. To the residue, was added water (500 mL). The aqueous layer was extracted with methylene chloride (3×100 mL). The combined organic layers were separated, dried over magnesium sulfate, and concentrated to give 5-(tert-butoxycarbonylamino-methyl)-2-nitro-benzoic acid as a brown oil (21.0 g, 41% yield). The product was used in the next step without further purification.

Step 5: A mixture of 5-(tert-butoxycarbonylamino-methyl)-2-nitro-benzoic acid (21.0 g, 70.9 mmol) in methanol (210 mL) and palladium/carbon (2 g) was hydrogenated with a Parr-shaker overnight at 51 psi. The black mixture was filtered through a pad of Celite, and the filtrate was evaporated to give a brown oil, which was stirred in ether (300 mL) overnight. The ether slurry was filtered to give 2-amino-5-(tert-butoxycarbonylamino-methyl)-benzoic acid as a brown solid (9.3 g, 49% yield). The product was used in the next step without further purification.

Step 6: To a stirred solution of 2-amino-5-(tert-butoxycarbonylamino-methyl)-benzoic acid (9.3 g, 34.9 mmol), imidazole (2.85 g, 41.9 mmol) in acetonitrile (120 mL), was added acetyl chloride (3.0 mL, 41.9 mmol) and stirred at room temp overnight. Then to the mixture, was added 3-amino-piperidine-2,6-dione hydrogen chloride (5.74 g, 34.9 mmol), imidazole (4.76 g, 69.8 mmol) and triphenyl phosphite (11.0 mL, 41.9 mmol), and the mixture was heated to reflux for 6 hours. The mixture was allowed to cool to room temperature, and water (about 400 mL) was added. The suspension was filtered, washed with water (50 mL), ethyl acetate (20 mL), ether (50 mL), and suction dried to give [3-(2,6-dioxo-piperidin-3-yl)-2-methyl-4-oxo-3,4-dihydro-quinazolin-6-ylmethyl]-carbamic acid tert-butyl ester as an off-white solid (9.7 g, 70% yield): HPLC, Waters Symmetry C$_{18}$, 5 μm, 3.9×150 mm, 1 mL/min, 240 nm, 10/90 CH$_3$CN/0.1% H$_3$PO$_4$, grad. to 95/5 in 5 min, kept 5 min, 5.95 min (96.7%); mp, 212.5-214.5° C.; $^1$HNMR (DMSO-d$_6$) δ 1.40 (s, 9H, CMe$_3$), 2.15-2.18 (m, 1H, CHH), 2.57-2.86 (m, 5H, CHCH$_2$, CH$_3$), 4.23 (d, J=6 Hz, 2H, CH$_2$NH), 5.26 (dd, J=6, 11 Hz, 1H, CH), 7.52 (t, J=6 Hz, 1H, CH$_2$NH), 7.56-7.88 (m, 3H, Ar), 11.03 (s, 1H, NH); $^{13}$C NMR (DMSO-d$_6$) δ 20.92, 23.40, 28.20, 30.62, 42.97, 56.52, 77.94, 119.98, 123.50, 126.51, 133.74, 138.76, 145.75, 154.52, 155.79, 160.44, 169.47, 172.61. LCMS MH=401; Anal Calcd For C$_{20}$H$_{24}$N$_4$O$_3$: C, 59.99; H, 6.04; N, 13.99. Found: C, 59.83; H, 5.98; N, 13.85.

5.12 3-(6-aminomethyl-2-methyl-4-oxo-4H-quinazolin-3-yl)-piperidine-2,6-dionehydrogen chloride

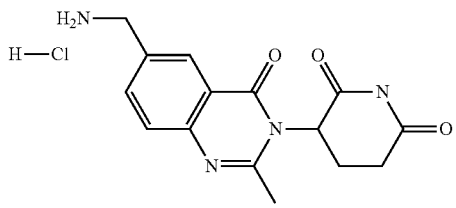

Step 1: To a stirred brown solution of [3-(2,6-dioxo-piperidin-3-yl)-2-methyl-4-oxo-3,4-dihydro-quinazolin-6-ylmethyl]-carbamic acid tert-butyl ester (3.5 g, 8.7 mmol) in methanol (36 mL) and methylene chloride (36 mL), was added 2 M HCl in ether (102 mL), and the mixture was stirred overnight. The solvent was evaporated, and the residue was stirred in ether (100 mL) for 2 hours. The suspension was filtered to give 3-(6-amino-2-methyl-4-oxo-4H-quinazolin-3-yl)-piperidine-2,6-dione hydrogen chloride as a light yellow solid (3.2 g, 109% crude yield). The product was used in the next step without purification.

Step 2: 3-(6-Aminomethyl-2-methyl-4-oxo-4H-quinazolin-3-yl)-piperidine-2,6-dione hydrogen chloride (0.95 g) was dissolved in water (100 mL). The solution was washed with ethyl acetate (2×100 mL). The aqueous layer was evaporated to give 3-(6-aminomethyl-2-methyl-4-oxo-4H-quinazolin-3-yl)-piperidine-2,6-dione hydrogen chloride as an off-white solid (0.79 g, 84% yield); HPLC, Waters Xterra RP 18, 5 μm, 3.9×150 mm, 1 mL/min, 240 nm, Waters LC Module 1, 05/95 CH$_3$CN/0.1% (HCO$_2$)NH$_4$ is ° Crat. 4.67 min (98.5%); mp. 299-301° C.; $^1$HNMR (DMSO-d$_6$) δ 2.18-2.24 (m, 1H, CHH), 2.59-2.89 (m, 6H, CHCH$_2$, CH$_3$), 4.14-4.19 M, 2H, ArCH$_2$), 5.34 (dd, J=5, 11 Hz, 1H, CH), 7.71-8.20 (m, 3H, Ar), 8.54 (brs, 3H, ClNH$_3$), 11.08 (s, 1H, NH); $^{13}$C NMR (DMSO-d$_6$) δ 20.86, 22.97, 30.60, 41.61, 56.75, 119.85, 125.75, 126.83, 132.81, 135.80, 145.35, 156.51, 159.96, 169.23, 172.59. LCMS MH=301; Anal Calcd For C$_{15}$H$_{17}$N$_2$O$_3$Cl+1.0 H$_2$O and +0.8 HCl; C, 46.92; H, 5.20; N, 14.59; Cl, 16.62. Found: C, 46.72; H, 5.15; N, 14.29; Cl, 16.59.

5.13 Heptanoic acid [3-(2,6-dioxo-piperidin-3-yl)-2-methyl-4-oxo-3,4-dihydro-quinazolin-6-ylmethyl]-amide

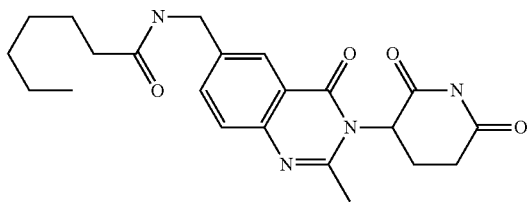 [SMILES: CCCCCCC(=O)NCc1ccc2nc(C)n(C3CCC(=O)NC3=O)c(=O)c2c1]

To a stirred suspension of 3-(6-aminomethyl-2-methyl-4-oxo-4H-quinazolin-3-yl)-piperidine-2,6-dione hydrogen chloride (0.49 g, 1.5 mmol) in acetonitrile (10 mL), was added heptanoyl choloride (0.34 mL, 2.2 mmol) and N,N-diisopropyl ethylamine (0.60 mL, 3.7 mmol). The mixture was stirred at room temperature for one hour. The solvent was evaporated, and the residue was purified by flash column chromatography (Silica gel, methanol/methylene chloride 4%/96%) to give heptanoic acid [3-(2,6-dioxo-piperidin-3-yl)-2-methyl-4-oxo-3,4-diyhydro-quinazolin-6-ylmethyl]-amide as an off-white solid (349 mg, 58% yield); HPLC, Waters Symmetry C$_{18}$, 5 μm, 3.9×150 mm, 1 mL/min, 240 nm, 10/90 CH$_3$CN/0.1% H$_3$PO$_4$, gradient to 95/5 in 5 min, kept for 5 min, 6.12 min (96.3%); mp, 223-225° C.; $^1$HNMR (DMSO-d$_6$) δ 0.84 (t, J=6 Hz, 3H, CH$_3$ of long chain), 1.24-2.20 (m, 11H, CH$_2$CH$_2$CH$_2$CH$_2$CH$_2$, CHH), 2.57-2.86 (m, 6H, CHCH$_2$, CH$_3$), 4.36 (d, J=6 Hz, 2H, CH$_2$NH), 5.26 (dd, J=6, 11 Hz, 1H, CH), 7.56-7.88 (m, 3H, Ar), 8.41 (t, J=6 Hz, 1H, CH$_2$NH), 11.03 (s, 1H, NH); $^{13}$C NMR (DMSO-d$_6$) δ 13.86, 20.92, 21.95, 23.39, 25.23, 28.31, 30.61, 30.99, 35.33, 41.57, 56.51, 119.99, 123.79, 126.51, 133.96, 138.38, 145.74, 154.53, 160.40, 169.47, 172.25, 172.60. LCMS MH=413; Anal Calcd For C$_{22}$H$_{28}$N$_4$O$_4$: C, 64.06; H, 6.84; N, 13.58. Found: C, 63.76; H, 6.68; N, 13.42.

5.14 Cyclopropanecarboxylic acid [3-(2,6-dioxo-piperidin-3-yl)-2-methyl-4-oxo-3,4-dihydro-quinazolin-6-ylmethyl]-amide

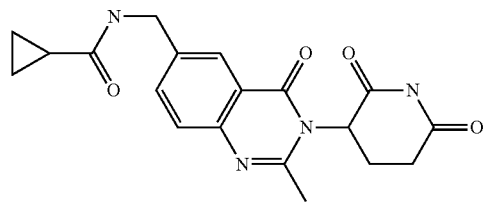 [SMILES: Cc1nc2ccc(CNC(=O)C3CC3)cc2c(=O)n1C1CCC(=O)NC1=O]

To a stirred suspension of 3-(6-aminomethyl-2-methyl-4-oxo-4H-quinzaolin-3-yl)-piperidine-2,6-dione hydrogen chloride (0.51 g, 1.5 mmol) in acetonitrile (10 mL), was added cyclopropanecarbonyl chloride (0.21 mL, 2.3 mmol) and N,N-diisopropyl ethylamine (0.62 mL, 3.8 mmol). The mixture was stirred at room temperature for one hour. The solvent was evaporated, and the residue was purified by flash column chromatography (Silica gel, methanol/methylene chloride 4%/96%) to give cyclopropanecarboxylic acid [3-(2,6-dioxo-piperidin-3-yl)-2-methyl-4-oxo-3,4-dihydro-quinazolin-6-ylmethyl]-amide as an off-white solid (233 mg, 42% yield); HPLC, Waters Symmetry C$_{18}$, 5 μm, 3.9×150 mm, 1 mL/min, 240 nm, 10/90 CH$_3$CN/0.1% H$_3$PO$_4$, gradient to 95/5 in 5 min, kept for 5 min, 5.01 min (98.4%); mp, 281-283° C.; $^1$HNMR (DMSO-d$_6$) δ 0.64-0.74 (m, 4H, CH$_2$CH$_2$ of cyclopropane ring), 1.57-1.66 (m, 1H, CH of cyclopropane ring), 2.15-2.21 (m, 1H, CH), 2.57-2.89 (m, 6H, CHCH$_2$, CH$_3$), 4.39 (d, J=5 Hz, 2H), 5.26 (dd, J=6, 11 Hz, 1H, CH), 7.57-7.89 (m, 3H, Ar), 8.68 (t, J=6 Hz, 1H, CH$_2$NH), 11.03 (s, 1H, NH); $^{13}$C NMR (DMSO-d$_6$) δ 6.31, 13.55, 20.93, 23.40, 30.61, 41.77, 56.53, 120.01, 123.78, 126.58, 134.02, 138.34, 145.78, 154.55, 160.44, 169.47, 172.62, 172.70, LCMS MH=413; Anal Calcd For C$_{19}$H$_{20}$N$_4$O$_4$: C, 61.95; H, 5.47; N, 15.21. Found: C, 61.86; H, 5.49; N, 15.04.

5.15 3-[3-(2,6-dioxo-piperidin-3-yl)-2-methyl-4-oxo-3,4-dihydro-quinazolin-6-ylmethyl]-1,1-dimethyl-urea

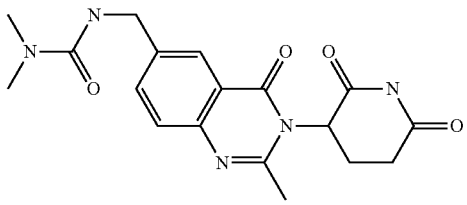 [SMILES: Cc1nc2ccc(CNC(=O)N(C)C)cc2c(=O)n1C1CCC(=O)NC1=O]

To a stirred suspension of 3-(6-aminomethyl-2-methyl-4-oxo-4H-quinazolin-3-yl)-piperidine-2,6-dione hydrogen chloride (0.50 g, 1.5 mmol) in acetonitrile (10 mL), was added dimethyl carbamyl choloride (0.21 mL, 2.2 mmol) and N,N-diisopropyl ethylamine (0.62 mL, 3.8 mmol). The mixture was stirred at room temperature overnight. The solvent was evaporated, and the residue was purified by flash column chromatography (Silica gel, methanol/methylene chloride 4%/96%) to give 3-[3-(2,6-dioxo-piperidin-3-yl)-2-methyl-4-oxo-3,4-dihydro-quinazolin-6-ylmethyl]-1,1-dimethyl-urea as an off-white solid (290 mg, 52% yield); HPLC, Waters Symmetry $C_{18}$, 5 μm, 3.9×150 mm, 1 mL/min, 240 nm, 10/90 $CH_3CN$/0.1% $H_3PO_4$, gradient to 95/5 in 5 min, kept for 5 min, 4.66 min (98.7%); mp, 264-268° C.; $^1$HNMR (DMSO-$d_6$) δ 2.14-2.20 (m, 1H, CH), 2.56-2.86 (m, 12H, N(CH$_3$)$_2$, CHCH$_2$, CH$_3$), 4.31 (d, J=5 Hz, 2H, CH$_2$NH), 5.26 (dd, J=6, 11 Hz, 1H, CH), 7.00 (t, J=5 Hz, 1H, CH$_2$NH), 7.54-7.89 (m, 3H, Ar), 11.03 (s, 1H, NH); $^{13}$C NMR (DMSO-$d_6$) δ 20.95, 23.38, 30.61, 35.85, 43.20, 56.49, 119.88, 123.54, 126.30, 133.91, 139.98, 145.59, 154.27, 158.09, 160.50, 169.49, 172.62. LCMS MH-372; Anal Calcd For $C_{18}H_{21}N_5O_4$+0.5 $H_2O$: C, 56.83; H, 5.83; N, 18.41. Found: C, 56.71; H, 5.81; N, 18.18.

5.16 2-(4-chloro-phenyl)-N-[3-(2,6-dioxo-piperidin-3-yl)-2-methyl-4-oxo-3,4-dihydro-quinazolin-6-ylmethyl]-acetamide

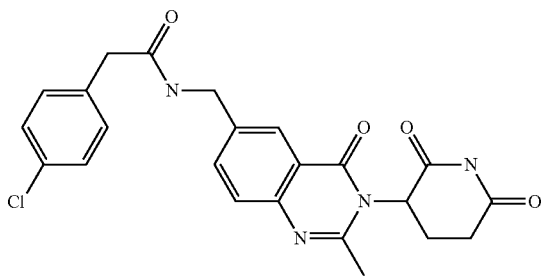

To a stirred solution of (4-chloro-phenyl)-acetic acid (0.30 g, 1.8 mmol) in DMF (8 mL) in a 40° C. oil bath, was added 1,1' carbonyldiimidazole (0.31 g, 1.9 mmol), and the mixture was stirred for one hour. Then 3-(6-aminomethyl-2-methyl-4-oxo-4H-quinazolin-3-yl)-piperidine-2,6-dione hydrogen chloride (0.59 g, 1.7 mmol) was added, and the mixture was stirred for 15 minutes. The solvent was evaporated, and the residue was purified by flash column chromatography (Silica gel, methanol/methylene chloride 4%/96%) to give 2-(4-chloro-phenyl)-N-[3-(2,6-dioxo-piperidin-3-yl)-2-methyl-4-oxo-3,4-dihydro-quinazolin-6-ylmethyl]-acetamide as a white solid (550 mg, 70% yield); HPLC, Waters Symmetry $C_{18}$, 5 μm, 3.9×150 mm, 1 mL/min, 240 nm, 10.90 $CH_3CN$/0.1% $H_3PO_4$, grad. to 95/5 in 5 min, kept 5 min, 6.00 min (98.7%); mp. 229.5-231.5° C.; $^1$HNMR (DMSO-$d_6$) δ 2.15-2.21 (m, 1H, CHH), 2.57-2.89 (m, 6H, CHCH$_2$, CH$_3$), 3.50 (s, 2H, ArCH$_2$), 4.37 (d, J=5 Hz, 2H, CH$_2$NH), 5.26 (dd, J=6, 11 Hz, 1H, CH), 7.27-7.90 (m, 7H, Ar), 8.67 (t, J=5 Hz, 1H, CH$_2$NH), 11.03 (s, 1H, NH); $^{13}$C NMR (DMSO-$d_6$) δ 20.92, 23.40, 30.63, 41.39, 41.87, 56.53, 120.02, 123.99, 126.57, 128.13, 130.87, 131.09, 134.03, 135.21, 137.97, 145.81, 154.61, 160.38, 167.47, 169.85, 172.61. LCMS MH=453, 455; Anal Calcd For $C_{23}H_{21}N_4O_4Cl$: C, 61.00; H, 4.67; N, 12.37; Cl, 7.83. Found: C, 60.88; H, 4.60; N, 12.27; Cl, 7.89.

5.17 1-[3-(2,6-dioxo-piperidin-3-yl)-2-methyl-4-oxo-3,4-dihydro-quinazolin-6-ylmethyl]-3-hexyl-urea

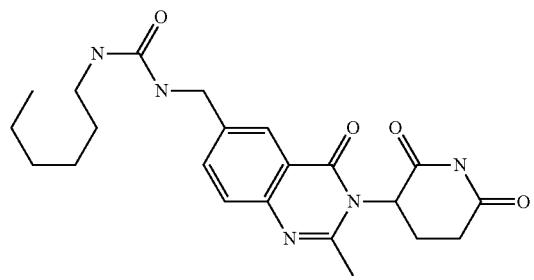 [SMILES: CCCCCCNC(=O)NCc1ccc2nc(C)n(C3CCC(=O)NC3=O)c(=O)c2c1]

To a stirred suspension of 3-(6-aminomethyl-2-methyl-4-oxo-4H-quinazolin-3-yl)-piperidine-2 2,6-dione hydrogen chloride (0.50 g, 1.5 mmol) and triethylamine (0.29 mL, 2.1 mmol) in THF (12 mL) at 5~10° C., was added hexyl isocyanate (0.25 g, 1.9 mmol), and the mixture was stirred at room temperature overnight. The mixture was quenched with methanol (~1 mL), and the solvent was evaporated. The residue was purified by flash column chromatography (Silica gel, methanol/methylene choloride 4%/96%) to give 1-[3-(2,6-dioxo-piperidin-3-yl)-2-methyl-4-oxo-3,4-dihydro-quinazolin-6-ylmethyl]-3-hexyl-urea as an off-white solid (410 mg, 65% yield); HPLC, Waters Symmetry $C_{18}$, 5 μm, 3.9×150 mm, 1 mL/min, 240 nm, 10/90 $CH_3CN$/0.1% $H_3PO_4$, grad. to 95/5 in 5 min, kept 5 min, 6.05 min (99.0%); mp, 220-222° C.; $^1$HNMR (DMSO-$d_6$) δ 0.85 (t, J=6 Hz, 3H, CH$_3$CH$_2$CH$_2$), 1.24-1.38 (m, 8H, CH$_2$CH$_2$CH$_2$CH$_2$), 2.15-2.20 (m, 1H, CHH), 2.56-3.03 (m, 6H, CHCH$_2$, CH$_3$), 4.30 (d, J=6 Hz, 2H, ArCH$_2$NH), 5.26 (dd, J=6, 11 Hz, 1H CH), 5.96 (t, J=5 Hz, 1H, CH$_2$NH), 6.40 (t, J=6 Hz, 1H, ArCH$_2$NH), 7.55-7.89 (m, 3H, Ar), 11.02 (s, 1H, NH); $^{13}$C NMR (DMSO-$d_6$) δ 13.88, 20.93, 22.05, 23.38, 26.03, 29.94, 30.63, 31.02, 39.35, 42.44, 56.51, 119.96, 123.46, 126.40, 133.81, 139.87, 145.64, 154.39, 157.99, 160.46, 169.47, 172.60. LCMS MH=428; Anal Calcd For $C_{22}H_{29}N_5O_4$: C, 61.81; H, 6.84; N, 16.38. Found: C, 61.50; H, 6.82; N, 16.23.

5.18 1-(4-chloro-phenyl)-3-[3-(2,6-dioxo-piperidin-3-yl)-2-methyl-4-oxo-3,4-dihydro-quinazolin-6-ylmethyl]-urea

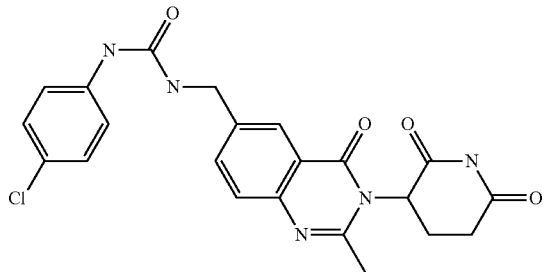 [SMILES: Cc1nc2ccc(CNC(=O)Nc3ccc(Cl)cc3)cc2c(=O)n1C1CCC(=O)NC1=O]

To a stirred suspension of 3-(6-aminomethyl-2-methyl-4-oxo-4H-quinazolin-3-yl)-piperidine-2,6-dione hydrogen chloride (0.47 g, 1.4 mmol) and triethylamine (0.27 mL, 2.0 mmol) in THF (8 mL) at 5~10° C., was added 4-chlorophenyl isocyanate (0.28 g, 1.8 mmol), and the mixture was stirred at room temperature overnight. The mixture was quenched with methanol (~1 mL), and the solvent was evaporated. The residue was purified by flash column chromatography (Silica gel, methanol/methylene chloride 4%/96%) to give 1-(4-chloro-phenyl)-3-[3-(2,6-dioxo-piperidin-3-yl)-2-methyl-4-oxo-3,4-dihydro-quinazolin-6-ylmethyl]-urea as an off-white solid (400 mg, 63% yield); HPLC, Waters Symmetry $C_{18}$, 5 µm, 3.9×150 mm, 1 mL/min, 240 nm, 10/90 $CH_3CN$/0.1% $H_3PO_4$, grad. to 95/5 in 5 min, kept 5 min, 6.18 min (98.9%); mp. 225-227° C.; $^1$HNMR (DMSO-$d_6$) δ 2.15-2.20 (m, 1H, CHH), 2.56-2.91 (m, 6H, $CHCH_2$, $CH_3$), 4.41 (d, J=5 Hz, 2H, $CH_2NH$), 5.26 (dd, J=6, 11 Hz, 1H, CH), 6.81 (t, J=6 Hz, 1H, $CH_2NH$), 7.23-7.95 (m, 7H, Ar), 8.80 (s, 1H, NH), 11.02 (s, 1H, NH); $^{13}$C NMR (DMSO-$d_6$) δ 20.93, 23.38, 30.61, 42.33, 56.54, 119.23, 120.01, 123.67, 124.57, 126.53, 128.42, 133.95, 139.05, 139.37, 145.74, 154.53, 155.09, 160.46, 169.47, 172.60. LCMS MH=454, 456; Anal Calcd For $C_{22}H_{20}N_5O_4Cl$+0.8 $H_2O$: C, 56.43; H, 4.65; N, 14.95; Cl, 7.57. Found: C, 56.45; H, 4.56; N, 14.87; Cl, 7.69.

5.19 1-[3-(2,6-dioxo-piperidin-3-yl)-2-methyl-4-oxo-3,4-dihydro-quinazolin-6-ylmethyl]-3-m-tolyl-urea

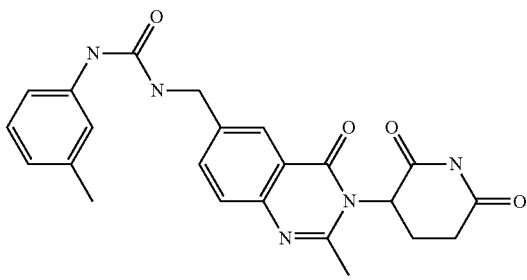 [SMILES: Cc1cccc(NC(=O)NCc2ccc3nc(C)n(C4CCC(=O)NC4=O)c(=O)c3c2)c1]

To a stirred suspension of 3-(6-aminomethyl-2-methyl-4-oxo-4H-quinazolin-3-yl)-piperidine-2,6-dione hydrogen chloride (0.50 g, 1.5 mmol) and triethylamine (0.29 mL, 2.1 mmol) in THF (12 mL) at 5~10° C., was added m-toluyl isocyanate (0.25 mL, 1.90 mmol), and the mixture was stirred at room temperature overnight. The mixture was quenched with methanol (~1 mL), and the solvent was evaporated. The residue was purified by flash column chromatography (Silica gel, methanol/methylene chloride 4%/96%) to give 1-[3-(2,6-dioxo-piperidin-3-yl)-2-methyl-4-oxo-3,4-dihydro-quinazolin-6-ylmethyl]-3-m-tolyl-urea as an off-white solid (437 mg, 68% yield); HPLC, Waters Symmetry $C_{18}$, 5 µm, 3.9×150 mm, 1 mL/min, 240 nm, 10/90 $CH_3CN$/0.1% $H_3PO_4$, grad. to 95/5 in 5 min, kept 5 min, 5.95 min (99.0%); MP, 200-202° C.; $^1$HNMR (DMSO-$d_6$) δ 2.07-2.24 (m, 4H, $ArCH_3$, CHH), 2.56-2.88 (m, 6H, $CHCH_2$, $CH_3$), 4.40 (d, J=5 Hz, 2H, $CH_2NH$), 5.26 (dd, J=6, 11 Hz, 1H, CH), 6.70-7.95 (m, 3H, Ar and $CH_2NH$), 8.54 (s, 1H, NH), 11.01 (s, 1H, NH); $^{13}$C NMR (DMSO-$d_6$) δ 20.92, 21.19, 23.39, 30.61, 42.30, 56.53, 114.93, 118.27, 120.00, 121.87, 123.63, 126.53, 128.44, 133.94, 137.70, 139.23, 140.26, 145.73, 154.50, 155.22, 160.46, 169.48, 172.61. LCMS MH=434; Anal Calcd For $C_{23}H_{23}N_5O_4$+1.4 $H_2O$: C, 60.23; H, 5.67; N, 15.27. Found: C, 60.18; H, 5.44; N, 15.09.

5.20 1-[3-(2,6-dioxo-piperidin-3-yl)-2-methyl-4-oxo-3,4-dihydro-quinazolin-6-ylmethyl]-3-(4-trifluoromethoxy-phenyl)-urea

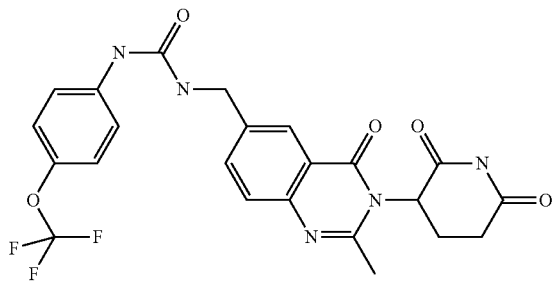 [SMILES: Cc1nc2ccc(CNC(=O)Nc3ccc(OC(F)(F)F)cc3)cc2c(=O)n1C1CCC(=O)NC1=O]

To a stirred suspension of 3-(6-aminomethyl-2-methyl-4-oxo-4H-quinazolin-3-yl)-piperidine-2,6-dione hydrogen chloride (0.49 g, 1.5 mmol) and triethylamine (0.28 mL, 2.1 mmol) in THF (12 mL) at 5~10° C., was added trifluoromethoxy-phenyl isocyanate (0.29 mL, 1.9 mmol), and the mixture was stirred at room temperature overnight. The mixture was quenched with methanol (~1 mL), and the solvent was evaporated. The residue was purified by flash column chromatography (Silica gel, methanol/methylene chloride 4%/96%) to give 1-[3-(2,6-dioxo-piperidin-3-yl)-2-methyl-4-oxo-3,4-dihydro-quinazolin-6-ylmethyl]-3-(4-trifluoromethoxy-phenyl)-urea as an off-white solid (490 mg, 67% yield); HPLC, Waters Symmetry $C_{18}$, 5 µm, 3.9×150 mm, 1 mL/min, 240 nm, 10/90 $CH_3CN$/0.1% $H_3PO_4$, grad. to 95/5 in 5 min, kept 5 min, 6.47 min (98.6%); mp. 201-203° C.; $^1$HNMR (DMSO-$d_6$) δ 2.15-2.20 (m, 1H, CHH), 2.56-2.90 (m, 6H, $CHCH_2$, $CH_3$), 4.42 (d, J=5 Hz, 2H, $CH_2NH$), 5.26 (dd, J=6, 11 Hz, 1H, CH), 6.84 (t, J=6 Hz, 1H, $CH_2NH$), 7.21-7.96 (m, 7H, Ar), 8.88 (s, 1H, NH), 11.02 (s, 1H, NH); $^{13}$C NMR (DMSO-$d_6$) δ 20.93, 23.39, 30.61, 42.33, 56.53, 118.81, 120.01, 120.17 (q, $J_{C-F}$=255 Hz), 121.54, 123.66, 126.54, 133.93, 139.04, 139.69, 142.08, 145.76, 154.52, 155.12, 160.46, 169.48, 172.60. LCMS MH=504; Anal Calcd For $C_{23}H_{20}N_5O_5F_3$+0.2 $H_2O$: C, 54.48; H, 4.06; N, 13.81; F, 11.24. Found: C, 54.25; H, 4.00; N, 13.59; F, 11.24.

5.21 N-[3-(2,6-dioxo-piperidin-3-yl)-2-methyl-4-oxo-3,4-dihydro-quinazolin-6-ylmethyl]-4-trifluoromethylsulfanyl-benzamide

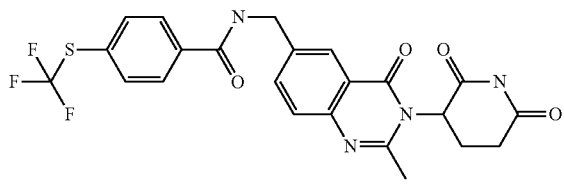 [SMILES: Cc1nc2ccc(CNC(=O)c3ccc(SC(F)(F)F)cc3)cc2c(=O)n1C1CCC(=O)NC1=O]

To a stirred suspension of 3-(6-aminomethyl-2-methyl-4-oxo-4H-quinazolin-3-yl)-piperidine-2,6-dione hydrogen chloride (0.47 g, 1.4 mmol) in acetonitrile (10 mL), was added 4-trifluoromethylthio-benzoyl chloride (0.35 mL, 2.1 mmol) and N,N-diisopropyl ethylamine (0.58 mL, 3.5 mmol). The mixture was stirred at room temperature for one hour. The solvent was evaporated, and the residue was purified by flash column chromatography (Silica gel, methanol/methylene chloride 4%/96%) to give N-[3-(2,6-dioxo-piperidin-3-yl)-2-methyl-4-oxo-3,4-dihydro-quinazolin-6-ylmethyl]-4-trifluoromethyl-sulfanyl-benzamide as an off-white solid (470 mg, 66% yield); HPLC, Waters Symmetry $C_{18}$, 5 μm, 3.9×150 mm, 1 mL/min, 240 nm, 10/90 $CH_3CN$/0.1% $H_3PO_4$, gradient to 95/5 in 5 min, kept for 5 min, 6.63 min (96.8%); mp. 169-171° C.; $^1$HNMR (DMSO-$d_6$) δ 2.15-2.20 (m, 1H, CHH), 2.56-2.86 (m, 6H, $CHCH_2$, $CH_3$), 4.60 (d, J=5 Hz, 2H, $CH_2NH$), 5.26 (dd, J=6, 11 Hz, 1H, CH), 7.59-8.02 (m, 7H, Ar), 9.35 (t, J=5 Hz, 1H, $CH_2NH$), 11.02 (s, 1H, NH); $^{13}$C NMR (DMSO-$d_6$) δ 20.89, 23.41, 30.60, 42.38, 56.52, 120.01, 123.90, 126.33, 126.64, 128.64, 129.46 (q, $J_{C-F}$=307 Hz), 134.09, 135.91, 136.69, 137.86, 145.85, 154.64, 160.41, 165.28, 169.47, 172.62. LCMS MH=505; Anal Calcd For $C_{23}H_{19}N_4O_4F_3S$+0.8 $H_2O$: C, 53.24; H, 4.00; N, 10.80; F, 10.98; S, 6.18. Found: C, 53.17; H, 3.83; N, 10.60; F, 10.74; S, 6.14.

5.22 1-(3-chloro-4-methyl-phenyl)-3-[3-(2,6-dioxo-piperidin-3-yl)-2-methyl-4-oxo-3,4-dihydro-quinazolin-6-ylmethyl]-urea

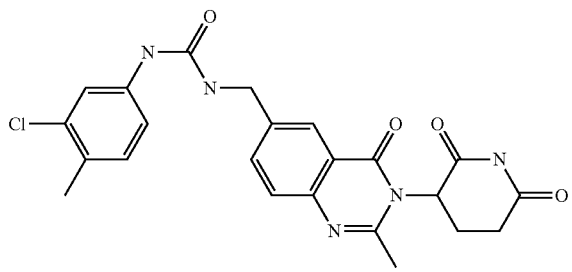 [SMILES: Cc1ccc(NC(=O)NCc2ccc3nc(C)n(C4CCC(=O)NC4=O)c(=O)c3c2)cc1Cl]

To a stirred suspension of 3-(6-aminomethyl-2-methyl-4-oxo-4H-quinazolin-3-yl)-piperidine-2,6-dione hydrogen chloride (0.46 g, 1.4 mmol) and triethylamine (0.27 mL, 1.9 mmol) in THF (10 mL) at 5~10° C., was added 3-chloro-4-methyl-phenyl isocyanate (0.24 mL, 1.8 mmol), and the mixture was stirred at room temperature overnight. The mixture was quenched with methanol (~1 mL), and the solvent was evaporated. The residue was purified by flash column chromatography (Silica gel, methanol/methylene chloride 4%/96%) to give 1-(3-chloro-4-methyl-phenyl)-3-[3-(2,6-dioxo-piperidin-3-yl)-2-methyl-4-oxo-3,4-dihydro-quinazolin-6-ylmethyl]-urea as an off-white solid (450 mg, 70% yield); HPLC, Waters Symmetry $C_{18}$, 5 μm, 3.9×150 mm, 1 mL/min, 240 nm, 10/90 $CH_3CN$/0.1% $H_3PO_4$, grad. to 95/5 in 5 min, kept 5 min, 6.38 (98.4%); mp, 186-188° C.; $^1$HNMR (DMSO-$d_6$) δ 2.15-2.23 (m, 4H, CHH and $CH_3Ar$), 2.56-2.86 (m, 6H, $CHCH_2$, $CH_3$), 4.40 (d, J=6 Hz, 2H, $CH_2NH$), 5.26 (dd, J=6, 11 Hz, 1H, CH), 6.81 (t, J=5 Hz, 1H, $CH_2NH$), 7.11-7.95 (m, 6H, Ar), 8.75 (s, 1H, NH), 11.02 (s, 1H, NH); $^{13}$C NMR (DMSO-$d_6$) δ 18.71, 20.93, 23.39, 30.61, 42.34, 56.53, 116.45, 117.66, 120.01, 123.67, 126.54, 127.39, 130.99, 132.96, 133.95, 139.05, 139.58, 145.76, 154.51, 155.08, 160.47, 169.47, 172.60. LCMS MH=478, 470; Anal Calcd For $C_{23}H_{22}N_5O_4Cl$+0.6 $H_2O$: C, 57.71; H, 4.88; N, 14.63; Cl, 7.41. Found: C, 57.63; H, 4.96; N, 14.50; Cl, 7.64.

5.23 4-chloro-N-[3-(2,6-dioxo-piperidin-3-yl)-2-methyl-4-oxo-3,4-dihydro-quinazolin-6-ylmethyl]-benzamide

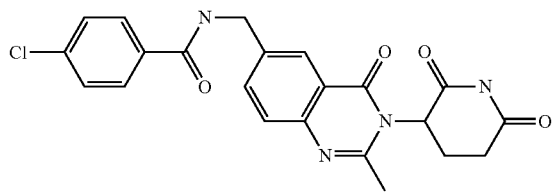 [SMILES: Cc1nc2ccc(CNC(=O)c3ccc(Cl)cc3)cc2c(=O)n1C1CCC(=O)NC1=O]

To a stirred suspension of 3-(6-aminomethyl-2-methyl-4-oxo-4H-quinazolin-3-yl)-piperidine-2,6-dione hydrogen chloride (0.54 g, 1.6 mmol) in acetonitrile (10 mL), was added 4-dichloro-benzoyl chloride (0.31 mL, 2.4 mmol) and N,N-diisopropyl ethylamine (0.66 mL, 4.0 mmol). The mixture was stirred at room temperature for 30 minutes. The solvent was evaporated, and the residue was purified by flash column chromatography (Silica gel, methanol/methylene chloride 4%/96%) to give 4-chloro-N-[3-(2,6-dioxo-piperidin-3-yl)-2-methyl-4-oxo-3,4-dihydro-quinazolin-6-ylmethyl]-benzamide as a white solid (298 mg, 42% yield); HPLC, Waters Symmetry $C_{18}$, 5 μm, 3.9×150 mm, 1 mL/min, 240 nm, 10/90 $CH_3CN$/0.1% $H_3PO_4$, gradient to 95/5 in 5 min, kept for 5 min, 6.00 min (99.0%); mp, 267-269° C.; $^1$HNMR (DMSO-$d_6$) δ 2.15-2.18 (m, 1H, CHH), 2.57-2.85 (m, 6H, $CHCH_2$, $CH_3$), 4.59 (d, J=5 Hz, 2H, $CH_2NH$), 5.26 (dd, J=6, 11 Hz, 1H, CH), 7.54-7.95 (m, 7H, Ar), 9.24 (t, J=5 Hz, 1H, $CH_2NH$), 11.02 (s, 1H, NH); $^{13}$C NMR (DMSO-$d_6$) δ 20.91, 23.40, 30.60, 42.33, 56.52, 120.01, 123.89, 126.62, 128.44, 129.15, 132.84, 134.09, 136.16, 138.02, 145.83, 154.60, 160.43, 165.23, 169.45, 172.60. LCMS MH=439, 441; Anal Calcd For $C_{22}H_{19}N_4O_4Cl$+0.3 $H_2O$: C, 59.48; H, 4.45; N, 12.61; Cl, 7.98. Found: C, 59.32; H, 4.10; N, 12.50; Cl, 7.99.

5.24 N-[3-(2,6-dioxo-piperidin-3-yl)-2-methyl-4-oxo-3,4-dihydro-quinazolin-6-ylmethyl]-3-trifluoromethyl-benzamide

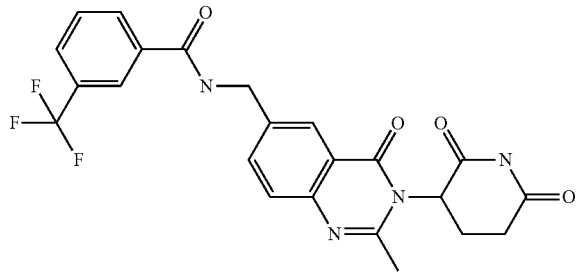 [SMILES: Cc1nc2ccc(CNC(=O)c3cccc(C(F)(F)F)c3)cc2c(=O)n1C1CCC(=O)NC1=O]

To a stirred solution of 3-trifluoromethyl-benzoic acid (0.30 g, 1.6 mmol) in DMF (8 mL) in a 40° C. oil bath, was added 1.1' carbonyldiimidazole (0.28 g, 1.7 mmol), and the mixture was stirred for one hour. Then 3-(6-aminomethyl-2-methyl-4-oxo-4H-quinazolin-3-yl)-piperidine-2,6-dione hydrogen chloride (0.53 g, 1.6 mmol) was added, and the mixture was stirred for 15 minutes. The solvent was evaporated, and the residue was purified by flash column chromatography (Silica gel, methanol/methylene chloride 4%/96%) to give N-[3-(2,6-dioxo-piperidin-3-yl)-2-methyl-4-oxo-3,4-dihydro-quinazolin-6-ylmethyl]-3-trifluoromethyl-benzamide as an off-white solid (430 mg, 59% yield): HPLC, Waters symmetry $C_{18}$, 5 μm, 3.9×150 mm, 1 mL/min, 240 nm, 10/90 $CH_3CN$/0.1% $H_3PO_4$, grad. to 95/5 in 5 min, kept 5 min, 6.20 min (98.5%); mp. 220-222° C.; $^1$HNMR (DMSO-$d_6$) δ 2.15-2.20 (m, 1H, CHH), 2.56-2.91 (m, 6H, $CHCH_2$, $CH_3$), 4.62 (d, J=5 Hz, 2H, $CH_2NH$), 5.26 (dd, J=6, 11 Hz, 1H, CH), 7.59-8.25 (m, 7H, Ar), 9.42 (t, J=5 Hz, 1H, $CH_2NH$), 11.02 (s, 1H, NH); $^{13}$C NMR (DMSO-$d_6$) δ 20.90, 23.41, 30.60, 42.45, 56.53, 120.02, 123.79 (q, $J_{C-F}$=11 Hz), 123.79 (d, $J_{C-F}$=3 Hz), 123.95 (q, $J_{C-F}$=275 Hz), 124.04, 126.67, 127.96 (d, $J_{C-F}$=3 Hz), 129.19 (d, $J_{C-F}$=32 Hz), 129.74, 131.38, 134.18, 134.88, 137.81, 145.88, 154.65, 160.43, 164.73, 169.45, 172.59. LCMS MH=473; Anal Calcd For $C_{23}H_{19}N_4O_4F_3$+0.3 $H_2O$: C, 57.81; H, 4.13; N, 11.73; F, 11.93. Found: C, 57.77; H, 4.11; N, 11.69; F, 11.97.

5.25 N-[3-(2,6-dioxo-piperidin-3-yl)-2-methyl-4-oxo-3,4-dihydro-quinazolin-6-ylmethyl]-4-trifluoromethoxy-benzamide

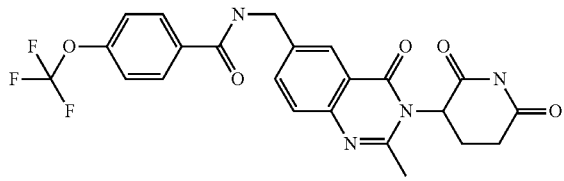 [SMILES: Cc1nc2ccc(CNC(=O)c3ccc(OC(F)(F)F)cc3)cc2c(=O)n1C1CCC(=O)NC1=O]

To a stirred suspension of 3-(6-aminomethyl-2-methyl-4-oxo-4H-quinazolin-3-yl)-piperidine-2,6-dione hydrogen chloride (0.49 g, 1.4 mmol) in acetonitrile (10 mL), was added 4-trifluoromethoxy-benzoyl chloride (0.34 g, 2.2 mmol) and N,N-diisopropyl ethylamine (0.63 mL, 3.6 mmol). The mixture was stirred at room temperature for one hour. The solvent was evaporated, and the residue was purified by flash column chromatography (Silica gel, methanol/methylene chloride 4%/96%) to give N-[3-(2,6-dioxo-piperidin-3-yl)-2-methyl-4-oxo-3,4-dihydro-quinazolin-6-ylmethyl]-4-trifluoromethoxy-benzamide as an off-white solid (500 mg, 71% yield); HPLC, Waters Symmetry $C_{18}$, 5 μm, 3.9×150 mm, 1 mL/min, 240 nm, 10/90 $CH_3CN$/0.1% $H_3PO_4$, gradient to 95/5 in 5 min, kept for 5 min, 6.40 min (99.5%); mp, 165-167° C.; $^1$HNMR (DMSO-$d_6$) δ 2.15-2.20 (m, 1H, CHH), 2.56-2.88 (m, 6H, $CHCH_2$, $CH_3$), 4.60 (d, J=5 Hz, 2H, $CH_2NH$), 5.26 (dd, J=6, 11 Hz, 1H, CH), 7.458-8.04 (m, 7H, Ar), 9.28 (t, J=5 Hz, 1H, $CH_2NH$), 11.02 (s, 1H, NH); $^{13}$C NMR (DMSO-$d_6$) δ 20.90, 23.40, 30.60, 42.35, 56.53, 119.93 (q, $J_{C-F}$=257 Hz), 120.01, 120.67, 123.87, 126.62, 129.56, 133.19, 134.17, 134.07, 137.97, 145.83, 150.35, 154.61, 160.43, 165.06, 169.45, 172.59. LCMS MH=489; Anal Calcd For $C_{23}H_{19}N_4O_5F_3$+1.1 $H_2O$); C, 54.36; H, 4.20; N, 11.02; F, 11.21. Found: C, 54.40; H, 3.89; N, 10.67; F, 11.06.

5.26 3,4-dichloro-N-[3-(2,6-dioxo-piperidin-3-yl)-2-methyl-4-oxo-3,4-dihydro-quinazolin-6-ylmethyl]-benzamide

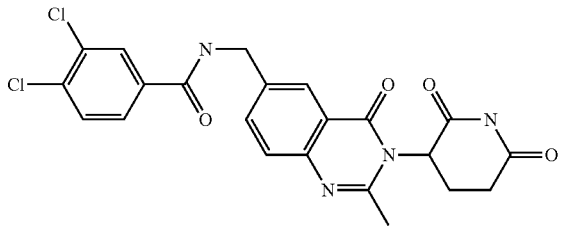 [SMILES: Cc1nc2ccc(CNC(=O)c3ccc(Cl)c(Cl)c3)cc2c(=O)n1C1CCC(=O)NC1=O]

To a stirred suspension of 3-(6-aminomethyl-2-methyl-4-oxo-4H-quinazolin-3-yl)-piperidine-2,6-dione hydrogen chloride (0.45 g, 1.4 mmol) in acetonitrile (10 mL), was added 3,4-dichloro-benzoyl chloride (0.34 g, 1.6 mmol) and N,N-diisopropyl ethylamine (0.54 mL, 3.2 mmol). The mixture was stirred at room temperature for 15 minutes. The solvent was evaporated, and the residue was purified by flash column chromatography (Silica gel, methanol/methylene chloride 4%/96%) to give 3,4-dichloro-N-[3-(2,6-dioxo-piperidin-3-yl)-2-methyl-4-oxo-3,4-dihydro-quinazolin-5-ylmethyl]-benzamide as an off-white solid (290 mg, 46% yield); HPLC, Waters Symmetry $C_{18}$, 5 μm, 3.9×150 mm, 1 mL/min, 240 nm, 10/90 $CH_3CN$/0.1% $H_3PO_4$, gradient to 95/5 in 5 min, kept for 5 min, 6.45 min (99.6%); mp, 177-179° C.; $^1$HNMR (DMSO-$d_6$) δ 2.16-2.18 (m, 1H, CHH), 7.58-8.14 (m, 6H, Ar), 9.34 (t, J=5 Hz, 1H, $CH_2NH$), 11.02 (s, 1H, NH); $^{13}$C NMR (DMSO-$d_6$) δ 20.91, 23.41, 30.61, 42.47, 56.53, 120.01, 124.94, 126.66, 127.56, 129.20, 130.77, 131.32, 134.17, 134.37, 137.71, 145.88, 154.65, 160.42, 164.00, 169.45, 172.60. LCMS MH=473, 475; Anal Calcd For $C_{22}H_{18}N_4O_4Cl_2$+1.0 $CH_2Cl_2$: C, 53.78; H, 4.10; N, 11.40; Cl, 14.43. Found: C, 53.44; H, 4.11; N, 11.27; Cl, 14.80.

5.27 N-[3-(2,6-dioxo-piperidin-3-yl)-2-methyl-4-oxo-3,4-dihydro-quinazolin-6-ylmethyl]-4-trifluoromethyl-benzamide

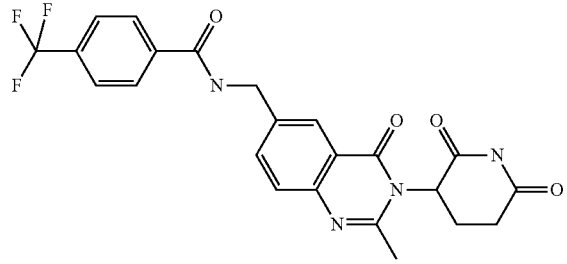 [SMILES: Cc1nc2ccc(CNC(=O)c3ccc(C(F)(F)F)cc3)cc2c(=O)n1C1CCC(=O)NC1=O]

To a stirred solution of 4-trifluoromethyl-benzoic acid (0.30 g, 1.6 mmol) in DMF (8 mL) in a 40° C. oil bath, was added 1,1' carbonyldiimidazole (0.29 g, 1.8 mmol), and the mixture was stirred for one hour. Then 3-(6-aminomethyl-2-methyl-4-oxo-4H-quinazolin-3-yl)-piperidine-2,6-dione hydrogen chloride (0.54 g, 1.6 mmol) was added, and the mixture was stirred for 15 minutes. The solvent was evaporated, and the residue was purified by flash column chromatography (Silica gel, methanol/methylene chloride 4%/96%) to give N-[3-(2,6-dioxo-piperidin-3-yl)-2-methyl-4-oxo-3,4-dihydro-quinazolin-6-ylmethyl]-4-trifluoromethyl-benzamide as an off-white solid (500 mg, 67% yield); HPLC, Waters Symmetry $C_{18}$, 5 μm, 3.9×150 mm, 1 mL/min, 240 nm, 10/90 $CH_3CN$/0.1% $H_3PO_4$, grad. to 95/5 in 5 min, kept 5 min, 6.33 min (99.1%): mp, 221-223° C.; $^1$HNMR (DMSO-$d_6$) δ 2.14-2.20 (m, 1H, CHH), 2.56-2.88 (m, 6H, $CHH_2$, $CH_3$), 4.62 (d, J=5 Hz, 2H, $CH_2NH$), 5.26 (dd, J=6, 11 Hz, 1H, CH), 7.59-8.11 (m, 7H, Ar), 9.40 (t, J=5 Hz, 1H, $CH_2NH$), 11.02 (s, 1H, NH); $^{13}$C NMR (DMSO-$d_6$) δ 20.90, 23.41, 30.60, 42.41, 56.53, 120.03, 123.90 (q, $J_{C-F}$=253 Hz), 123.95, 125.36 (d, $J_{C-F}$=3 Hz), 125.45 (d, $J_{C-F}$=3 Hz), 126.65, 128.14, 131.23 (d, $J_{C-F}$=31 Hz), 134.11, 137.83, 145.87, 154.64, 160.42, 165.12, 169.45, 172.59. LCMS MH=473; Anal Calcd For $C_{23}H_{19}N_4O_4F_3$: C, 58.48; H, 4.05; N, 11.86; F, 12.06. Found: C, 58.36; H, 3.96; N, 11.75; F, 11.84.

5.28 3-(2,7-dimethyl-4-oxo-4H-quinazolin-3-yl)-piperidine-2,6-dione

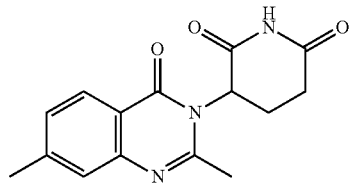 [SMILES: Cc1ccc2c(=O)n(C3CCC(=O)NC3=O)c(C)nc2c1]

To a stirred mixture of 2-amino-4-methylbenzoic acid (2.0 g, 13 mmol) and imidazole (1.1 g, 16 mmol) in acetonitrile (20 mL), was added acetyl chloride (1.1 mL, 16 mmol) at room temperature. The mixture was stirred at room temperature overnight. To the mixture, was added 3-amino-piperidine-2,6-dione hydrogen chloride (2.2 g, 13 mmol), imidazole (2.0 g, 30 mmol) and triphenyl phosphite (4.2 mL, 16 mmol) and heated to reflux for 22 hours. To the mixture, was added water (60 mL). The suspension was filtered and washed with water (2×50 mL), ethyl acetate (2×50 mL), and water (50 mL) to give 3-(2,7-dimethyl-4-oxo-4H-quinazolin-3-yl)-piperidine-2,6-dione as a white solid (2.52 g, 67% yield): HPLC: Waters Symmetry $C_{18}$, 5 μm, 3.9×150 mm, 1 mL/min, 240 nm, 20/80 $CH_3CN$/0.1% $H_3PO_4$, 5.13 min (99.9%); mp: 305° C. (decomp); $^1$H NMR (DMSO-$d_6$) δ 2.08-2.24 (m, 1H, CHH), 2.45 (s, 3H, $CH_3$), 2.56-2.75 (m, 5H, $CH_3$, 2CHH), 2.81-2.91 (m, 1H, CHH), 5.24 (dd, J=6, 11 Hz, 1H, NCH), 7.32 (dd, J=1.8 Hz 1H, Ar), 7.43 (s, 1H, Ar), 7.91 (d, J=8 Hz, 1H, Ar), 11.00 (s, 1H, NH); $^{13}$C NMR (DMSO-$d_6$) δ 21.00, 21.35, 23.45, 30.61, 56.43, 117.94, 125.80, 126.10, 127.97, 145.21, 146.98, 154.96, 160.34, 169.56, 172.62; LCMS: MH=286; Anal Calcd for $C_{15}H_{15}N_3O_3$: C, 63.15; H, 5.21; N, 14.73. Found: C, 63.14; H, 5.21; N, 14.76.

5.29 3-(7-fluoro-2-methyl-4-oxo-4H-quinazolin-3-yl)-piperidine-2,6-dione

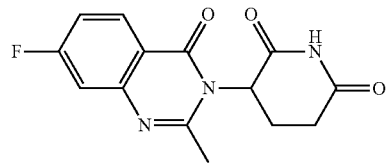 [SMILES: Cc1nc2cc(F)ccc2c(=O)n1C1CCC(=O)NC1=O]

To a stirred mixture of 2-amino-4-fluorobenzoic acid (2.5 g, 16 mmol) and imidazole (1.3 g, 19 mmol) in acetonitrile (25 mL), was added acetyl chloride (1.4 mL, 19 mmol) at room temperature. The mixture was stirred at room temperature overnight. To the mixture, was added 3-amino-piperidine-2,6-dione hydrogen chloride (2.7 g, 16 mmol), imidazole (2.4 g, 36 mmol) and triphenyl phosphite (5.1 mL, 19 mmol) and heated to reflux for 22 hours. To the mixture, was added water (60 mL). The suspension was filtered and washed with water (2×50 mL), ethyl acetate (2×50 mL), and water (50 mL) to give 3-(7-fluoro-2-methyl-4-oxo-4H-quinazolin-3-yl)-piperidine-2,6-dione as a white solid (2.5 g, 52% yield): HPLC: Waters Symmetry $C_{18}$, 5 μm, 3.9×150 mm, 1 mL/min, 240 nm, 25/75 $CH_3CN$/0.1% $H_3PO_4$, 3.83 min (100%); mp: 243-245° C.; $^1$H NMR (DMSO-$d_6$) δ 2.15-2.22 (m, 1H, CHH), 2.58-2.71 (m, 5H, $CH_3$, 2CHH), 2.79-2.86 (m, 1H, CHH), 5.28 (dd, J=5, 11 Hz, 1H, NCH), 7.34-7.44 (m, 2H, Ar), 8.10 (dd, J=6, 9 Hz, 1H, Ar), 11.05 (s, 1H, NH); $^{13}$C NMR (DMSO-$d_6$) δ 20.89, 23.50, 30.58, 56.59, 111.62 (d, $J_{C-F}$=22 Hz), 115.26 (d, $J_{C-F}$=24 Hz), 117.32, 129.19 (d, $J_{C-F}$=11 Hz), 148.97 (d, $J_{C-F}$=13 Hz), 156.65, 159.77, 165.83 (d, $J_{C-F}$=252 Hz), 169.41, 172.59; LCMS: MH=290; Anal Calcd for $C_{14}H_{12}N_3O_3F$: C, 58.13; H, 4.19; N, 14.53; F, 6.57. Found: C, 58.09; H, 4.08; N, 14.42; F, 6.72.

5.30 3-(7-chloro-2-methyl-4-oxo-4H-quinazolin-3-yl)-piperidine-2,6-dione

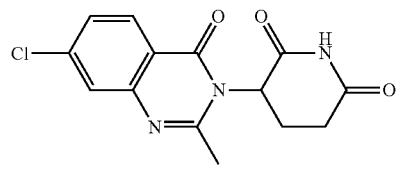 [SMILES: Cc1nc2cc(Cl)ccc2c(=O)n1C1CCC(=O)NC1=O]

To a stirred mixture of 2-amino-4-chlorobenzoic acid (5.0 g, 29 mmol) and imidazole (2.4 g, 35 mmol) in acetonitrile (50 mL), was added acetyl chloride (2.5 mL, 35 mmol) at room temperature. The mixture was stirred at room temperature overnight. To the mixture, was added 3-amino-piperidine-2,6-dione hydrogen chloride (4.8 g, 29 mmol), imidazole (4.4 g, 64 mmol) and triphenyl phosphite (8.4 mL, 32 mmol) and heated to reflux for 22 hours. The suspension was filtered and washed with acetonitrile (50 mL) and water (2×50 mL) to give 3-(7-chloro-2-methyl-4-oxo-4H-quinazolin-3-yl)-piperidine-2,6-dione as a white solid (6.5 g, 73% yield): HPLC: Waters Symmetry $C_{18}$, 5 μm, 3.9×150 mm, 1 mL/min, 240 nm, 30/70 $CH_3CN/0.1\% H_3PO_4$, 4.36 min (99.9%); mp: 291-293° C.; $^1H$ NMR (DMSO-$d_6$) δ 2.16-2.23 (m, 1H, CHH), 2.59-2.72 (m, 5H, $CH_3$, 2CHH), 2.79-2.92 (m, 1H, CHH), 5.29 (dd, J=5, 11 Hz, 1H, NCH), 7.53 (dd, J=2, 9 Hz, 1H, Ar), 7.69 (d, J=8 Hz, 1H, Ar), 8.03 (d, J=8 Hz, 1H, Ar), 11.07 (s, 1H, NH); $^{13}C$ NMR (DMSO-$d_6$) δ 20.84, 23.53, 30.58, 56.65, 19.06, 125.70, 126.91, 128.07, 139.30, 147.89, 156.74, 159.89, 169.35, 172.58; LCMS: MH=306, 308; Anal Calcd for $C_{14}H_{12}N_3O_3Cl$: C, 55.00; H, 3.96; N, 13.74; Cl, 11.60. Found: C, 55.24; H, 3.78; N, 13.74; Cl, 12.01.

5.31 3-(7-bromo-2-methyl-4-oxo-4H-quinazolin-3-yl)-piperidine-2,6-dione

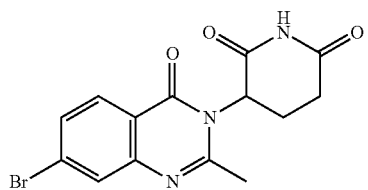 [SMILES: Cc1nc2cc(Br)ccc2c(=O)n1C1CCC(=O)NC1=O]

To a stirred mixture of 2-amino-4-bromobenzoic acid (2.0 g, 9.3 mmol) and imidazole (0.8 g, 11 mmol) in acetonitrile (20 mL), was added acetyl chloride (0.8 mL, 11 mmol) at room temperature. The mixture was stirred at room temperature overnight. To the mixture, was added 3-amino-piperidine-2,6-dione hydrogen chloride (1.5 g, 9.3 mmol), imidazole (1.4 g, 20 mmol) and triphenyl phosphite (2.9 mL, 11 mmol) and heated to reflux for 22 hours. To the mixture, was added water (30 mL). The suspension was filtered and washed with water (2×50 mL), ethyl acetate (2×50 mL), and water (50 mL) to give 3-(7-bromo-2-methyl-4-oxo-4H-quinazolin-3-yl)-piperidine-2,6-dione as a white solid (2.4 g, 75% yield): HPLC: Waters Symmetry $C_{18}$, 5 μm, 3.9×150 mm, 1 mL/min, 240 nm, 20/80 $CH_3CN/0.1\% H_3PO_4$, 18.65 min (98.9%); mp: 315-317° C.; $^1H$ NMR (DMSO-$d_6$) δ 2.08-2.22 (m, 1H, CHH), 2.62-2.79 (m, 5H, $CH_3$2CHH), 2.80-2.91 (m, 1H, CHH), 5.28 (dd, J=6, 11 Hz, 1H, NCH), 7.66 (dd, J=2, 8 Hz, 1H, Ar), 7.84 (d, J=2 Hz 2H, Ar), 7.95 (d, J=8 Hz, 1H, Ar), 11.05 (s, 1H, NH); $^{13}C$ NMR (DMSO-$d_6$) δ 20.83, 23.53, 24.02, 30.58, 56.67, 119.36, 128.06, 128.26, 128.80, 129.67, 147.93, 156.69, 160.02, 169.33, 172.57; LCMS: MH=350, 352: Anal Calcd for $C_{14}H_{12}N_3O_3Br$: C, 48.02; H, 3.45; N, 12.00; Br, 22.82. Found: C, 47.94; H, 3.17; N, 11.85; Br, 20.65.

5.32 3-(2-methyl-4-oxo-7-trifluoromethyl-4-H-quinazolin-3-yl)-piperidine-2,6-dione

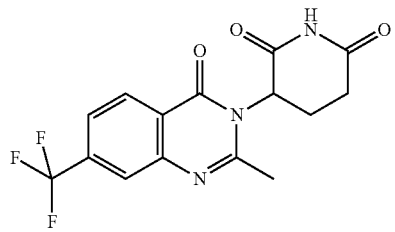 [SMILES: Cc1nc2cc(C(F)(F)F)ccc2c(=O)n1C1CCC(=O)NC1=O]

To a stirred mixture of 2-amino-4-(trifluoromethyl)benzoic acid (3.0 g, 15 mmol) and imidazole (1.2 g, 18 mmol) in acetonitrile (30 mL), was added acetyl chloride (1.3 mL, 18 mmol) at room temperature. The mixture was stirred at room temperature overnight. To the mixture, was added 3-amino-piperidine-2,6-dione hydrogen chloride (2.4 g, 15 mmol), imidazole (2.2 g, 32 mmol) and triphenyl phosphite (4.6 mL, 18 mmol) and heated to reflux for 22 hours. To the mixture, was added water (100 mL). The suspension was filtered and washed with water (2×50 mL), ethyl acetate (2×50 mL), sodium hydrogen carbonate (sat, 50 mL) and water (50 mL) to give a white solid, which was dissolved in DMSO (10 mL). To the solution, was added water (3 mL) to give a suspension. The suspension was filtered and washed with DMSO (2 mL) to give a white solid. The solid was stirred in water (50 mL) at 60° C. for 2 hours, then at room temperature overnight. The suspension was filtered and washed with water (2×50 mL) to give 3-(2-methyl-4-oxo-7-trifluoromethyl-4H-quinazolin-3-yl)-piperidine-2,6-dione as a white solid (1.17 g, 24% yield): HPLC: Waters Symmetry $C_{18}$, 5 μm, 3.9×150 mm, 1 mL/min, 240 nm, 30/70 $CH_3CN/0.1\% H_3PO_4$, 8.14 min (99.9%); mp: 277-279° C.; $^1H$ NMR (DMSO-$d_6$) δ 2.18-2.25 (m, 1H, CHH), 2.59-2.74 (m, 5H, $CH_3$, 2CHH), 2.81-2.88 (m, 1H, CHH), 5.34 (dd, J=6, 11 Hz, 1H, NCH), 7.80 (dd, J=2, 8 Hz, 1H, Ar), 7.96 (s, 1H, Ar), 8.24 (d, J=8 Hz, 1H, Ar), 11.09 (s, 1H, NH); $^{13}C$ NMR (DMSO-$d_6$) δ 20.73, 23.54, 30.57, 56.82, 122.30 (q, $J_{C-F}$=3 Hz), 122.99, 123.45 (q, $J_{C-F}$=273 Hz), 123.74 (q, $J_{C-F}$=4 Hz), 127.85, 134.22 (q, $J_{C-F}$=32 Hz), 146.84, 156.98, 159.80 169.24, 172.56; LCMS: MH=340; Anal Calcd for $C_{15}H_{12}N_3O_3F_3$: C, 53.10; H, 3.57; N, 12.39; F, 16.80. Found: C, 52.55; H, 3.42; N, 12.21; F, 17.18.

5.33 3-(7-fluoro-4-oxo-4H-quinazolin-3-yl)-piperidine-2,6-dione

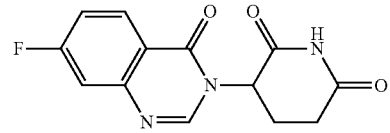

Step: 1 A mixture of 2-amino-4-fluorobenzoic acid (2.5 g, 16 mmol) and CDI (2.4 g, 15 mmol) in acetonitrile (30 mL) was stirred at room temperature for 1.5 hours. To the suspension, was added 3-amino-piperidine-2,6-dione hydrogen chloride (2.4 g, 15 mmol) and sodium hydrogen carbonate (1.6 g, 19 mmol), and the mixture was heated at 50° C. for 21 hours. The suspension was cooled to room temperature for 1 hour. The suspension was filtered and washed with acetonitrile (5 mL) and water (2×20 mL). The solid was stirred in methanol (15 mL) overnight. The suspension was filtered and washed with methanol (15 mL) to give 2-amino-N-(2,6-dioxo-piperidin-3-yl)-4-fluorobenzamide as an off-white solid (1.9 g, 45% yield): $^1$H NMR (DMSO-$d_6$) δ 1.91-1.96 (m, 1H, CHH), 2.04-2.18 (m, 1H, CHH), 2.50-2.56 (m, 1H, CHH), 2.73-2.85 (m, 1H, CHH), 4.67-4.76 (m, 1H, NCH), 6.35 (dt, J=2, 9 Hz, 1H, Ar), 6.48 (dd, J=2, 12 Hz, 1H, Ar), 6.76 (brs, 2H, NH$_2$), 7.58 (dd, J=7, 8 Hz, 1H, Ar), 8.50 (d, J=8 Hz, 1H, NH), 10.84 (s, 1H, NH); $^{13}$C NMR (DMSO-$d_6$) δ 24.06, 30.91, 48.98, 101.30 (d, $J_{C-F}$=23 Hz), 101.60 (d, $J_{C-F}$=22 Hz), 110.60, 130.66 (d, $J_{C-F}$=11 Hz), 152.16 (d, $J_{C-F}$=12 Hz), 164.46 (d, $J_{C-F}$=246 Hz), 167.80, 172.30, 172.94.

Step 2: A solution of 2-amino-N-(2,6-dioxo-piperidin-3-yl)-4-fluoro-benzamide (0.9 g, 3.4 mmol) and trimethyl orthoformate (4 mL) and p-toluene sulfonic acid (110 mg) was heated to 160° C. in a microwave oven for 15 minutes. To the mixture, was added methanol (10 mL), and the mixture was stirred for 10 minutes. The suspension was filtered and washed with methanol to give 3-(7-fluoro-4-oxo-4H-quinazolin-3-yl)-piperidine-2,6-dione as a white solid (650 mg, 70% yield): HPLC: Waters Symmetry $C_{18}$, 5 μm, 3.9×150 mm, 1 mL/min, 240 nm, 30.70 CH$_3$CN/0.1% H$_3$PO$_4$, 2.45 min (96.1%); mp: 296-298° C.; $^1$H NMR (DMSO-$d_6$) δ 2.13-2.19 (m, 1H, CHH), 2.63-2.73 (m, 2H, 2CHH), 2.82-2.93 (m, 1H, CHH), 5.50 (br, 1H, NCH), 7.46 (dt, J=3, 9 Hz, 1H, Ar), 7.53 (dd, J=3, 10 Hz, 1H, Ar), 8.22 (dd, J=6, 9 Hz, 1H, Ar), 8.42 (s, 1H, CH), 11.18 (s, 1H, NH); $^{13}$C NMR (DMSO-$d_6$) δ 22.45, 30.88, 56.43, 112.3 (d, $J_{C-F}$=22 Hz), 115.91 (d, $J_{C-F}$=23 Hz), 118.38, 139.32 (d, $J_{C-F}$=11 Hz), 148.71, 149.65 (d, $J_{C-F}$=14 Hz), 159.00, 165.70 (d, $J_{C-F}$=252 Hz), 169.76, 172.41; LCMS: MH=276; Anal Calcd for $C_{13}H_{10}N_3O_3F$: C, 56.73; H, 3.66; N, 15.27. Found: C, 56.39; H, 3.60; N, 15.16.

5.34 3-(7-methyl-4-oxo-4H-quinazolin-3-yl)-piperidine-2,6-dione

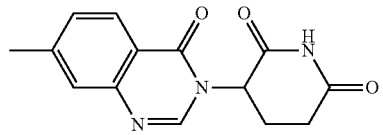 [SMILES: Cc1ccc2c(=O)n(C3CCC(=O)NC3=O)cnc2c1]

Step 1: A mixture of 2-amino-4-methylbenzoic acid (2.0 g, 13 mmol) and CDI (2.0 g, 12 mmol) in acetonitrile (20 mL) was stirred at room temperature for 1.5 hours. To the suspension, was added 3-amino-piperidine-2,6-dione hydrogen chloride (2.0 g, 12 mmol) and sodium hydrogen carbonate (1.3 g, 16 mmol), and the mixture was heated at 50° C. for 21 hours. The suspension was cooled to room temperature for 1 hour. The suspension was filtered and washed with water (50 mL) and ethyl acetate (20 mL). The solid was dried in a vacuum oven overnight to give 2-amino-N-(2,6-dioxo-piperidin-3-yl)-4-methyl-benzamide as a white solid (2.2 g, 69% yield): $^1$H NMR (DMSO-$d_6$) δ 1.90-1.96 (m, 1H, CHH), 2.05-2.14 (m, 1H, CHH), 2.18 (s, 3H, CH$_3$), 2.49-2.55 (m, 1H, CHH), 2.72-2.84 (m, 1H, CHH), 4.67-4.75 (m, 1H, NCH), 6.36 (dd, J=2, 8 Hz, 1H, Ar), 6.43 (br, 2H, NHH, Ar), 6.51 (s, 1H, NHH), 7.43 (d, J=8 Hz, 1H, Ar), 8.38 (d, J=8 Hz, 1H, NH), 10.83 (s, 1H NH); $^{13}$C NMR (DMSO-$d_6$) δ 21.05, 24.21, 30.99, 48.87, 111.26, 115.74, 116.48, 128.09, 141.71, 149.96, 168.54, 172.50, 173.04; LCMS: MH=262.

Step 2: A solution of 2-amino-N-(2,6-dioxo-piperidin-3-yl)-4-methyl-benzamide (1.0 g, 3.8 mmol) and trimethyl orthoformate (10 mL) and p-toluene sulfonic acid (250 mg) was heated to 160° C. in a microwave oven for 30 minutes. The suspension was filtered and washed with methanol (20 mL), water (20 mL) and methanol (20 mL) to give 3-(7-methyl-4-oxo-4H-quinazolin-3-yl)-piperidine-2,6-dione as an off-white solid (880 mg, 85% yield): HPLC: Waters Symmetry $C_{18}$, 5 μm, 3.9×150 mm, 1 mL/min, 240 nm, 20.80 CH$_3$CN/0.1% H$_3$PO$_4$, 5.14 min (97.1%); mp: 313-315° C.; $^1$H NMR (DMSO-$d_6$) δ 2.11-2.18 (m, 1H, CHH), 2.48 (s, 3H, CH$_3$), 2.61-2.74 (m, 2H, 2CHH), 2.82-2.92 (m, 1H, CHH), 5.46 (br, 1H, NCH), 7.41 (dd, J=1, 8 Hz, 1H, Ar), 7.53 (s, 1H, Ar), 8.03 (d, J=8 Hz, 1H, Ar), 8.33 (s, 1H, CH), 11.15 (s, 1H, NH); $^{13}$C NMR (DMSO-$d_6$) δ 21.23, 22.51, 30.91, 56.74, 118.95, 125.93, 126.74, 128.66, 145.27, 147.35, 147.59, 159.54, 169.88, 172.44; LCMS: MH=272; Anal Calcd for $C_{14}H_{13}N_3O_3$+0.1 $H_2O$: C, 61.58; H, 4.87; N, 15.39. Found: C, 61.41; H, 4.87; N, 15.15.

5.35 3-(7-amino-2-methyl-4-oxo-4H-quinazolin-3-yl)-piperidine-2,6-dione

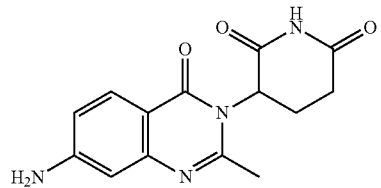 [SMILES: Cc1nc2cc(N)ccc2c(=O)n1C1CCC(=O)NC1=O]

Step 1: To a stirred mixture of 2-amino-4-nitrobenzoic acid (5.0 g, 28 mmol) and imidazole (2.2 g, 33 mmol) in acetonitrile (50 mL), was added acetyl chloride (2.3 mL, 33 mmol) at room temperature. The mixture was stirred at room temperature overnight. To the mixture, was added 3-amino-piperidine-2,6-dione hydrogen chloride (4.5 g, 28 mmol), imidazole (4.1 g, 60 mmol) and triphenyl phosphite (8.7 mL, 33 mmol), and heated to reflux for 22 hours. To the mixture, was added water (60 mL). The suspension was filtered and washed with water (2×50 mL), ethyl acetate (2×50 mL), and water (50 mL) to give 3-(2-methyl-7-nitro-4-oxo-4H-quinazolin-3-yl)-piperidine-2,6-dione as an off-white solid (4.8 g, 55% yield): HPLC: Waters Symmetry $C_{18}$, 5 μm, 3.9×150 mm, 1 mL/min, 240 nm, 10/90 CH$_3$CN/0.1% H$_3$PO$_4$, 5.69 min (95.4%); $^1$H NMR (DMSO-$d_6$) δ 2.15-2.25 (m, 1H, CHH), 2.59-2.69 (m, 2H, 2CHH), 2.70 (s, 3H, CH$_3$), 2.79-2.87 (m, 1H, CHH), 5.35 (dd, J=6, 12 Hz, 1H, NCH), 8.20-8.29 (m, 2H, Ar), 8.34 (d, J=2 Hz, 1H, Ar), 11.10 (s, 1H, NH); $^{13}$C NMR (DMSO-$d_6$) δ 20.60, 23.53, 30.49, 56.85, 120.26, 121.58, 124.35, 128.30, 147.08, 151.30, 157.61, 159.52, 160.09, 172.48; LCMS: MH=317.

Step 2: A suspension of 3-(2-methyl-7-nitro-4-oxo-4H-quinazolin-3-yl)-piperidine-2,6-dione (4.8 g, 13 mmol) and 20% Pd(OH)$_2$/C (1.0 g) in cyclohexene (15 mL) and DMF (60 mL) was heated in a 125° C. oil bath overnight. The suspension was filtered thru a pad of Celite, and washed with DMF (30 mL). To the filtrate, was added water (150 mL) to give a suspension. The suspension was filtered and washed with water (50 mL) to give 3-(7-amino-2-methyl-4-oxo-4H-quinazolin-3-yl)-piperidine-2,6-dione as an off-white solid (3.07 g, 71% yield): HPLC: Waters Symmetry $C_{18}$, 5 µm, 3.9×150 mm, 1 mL/min, 240 nm, 5/95 grad 95/5 in 5 min $CH_3CN/0.1\%$ $H_3PO_4$, 4.08 min (97.3%) [sample was dissolved in 0.1% $H_3PO_4$]; mp: 305-307° C.; $^1H$ NMR (DMSO-$d_6$) δ 2.05-2.16 (m, 1H, CHH), 2.53 (s, 3H, $CH_3$), 2.58-2.69 (m, 2H, 2CHH), 2.75-2.86 (m, 1H, CHH), 5.10 (dd, J=6, 11 Hz, 1H, NCH), 6.11 (brs, 2H, $NH_2$), 6.54 (d, J=2 Hz, 1H, Ar), 6.68 (dd, J=2, 8 Hz, 1H, Ar), 10.93 (s, 1H, NH); $^{13}C$ NMR (DMSO-$d_6$) δ 21.36, 23.43, 30.63, 55.97, 106.12, 109.17, 114.70, 127.28, 148.95, 154.42, 154.61, 159.85, 169.87, 172.67; LCMS: MH=287; Anal Calcd for $C_{14}H_{14}N_4O_3$: C, 58.74; H, 4.93; N, 19.57. Found: C, 58.60; H, 4.83; N, 19.40.

5.36 [3-(2,6-dioxo-piperidin-3-yl)-2-methyl-4-oxo-3,4-dihydro-quinazolin-7-ylmethyl]-carbamic acid tert-butyl ester

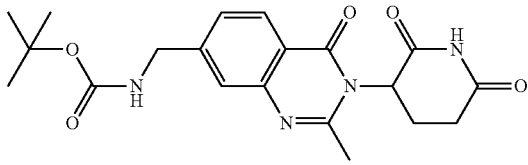 [SMILES: Cc1nc2cc(CNC(=O)OC(C)(C)C)ccc2c(=O)n1C1CCC(=O)NC1=O]

Step 1: To a stirred solution of 4-methyl-2-nitro-benzoic acid methyl ester (108.5 g, 555.7 mmol) in acetonitrile (750 mL), was added NBS (97.9 g, 550.1 mmol). The mixture was heated to a gentle reflux with a 200 W light bulb on for 5.5 hours. The solvent was evaporated, and the residue was dissolved in ethyl acetate (1500 mL). The solution was washed with water (2×600 mL) and brine (300 mL), dried over magnesium sulfate, and concentrated to give a brown oil. To the oil, was added 1-butyl methyl ether (300 mL). The mixture was heated at 70° C. for 15 minutes. The mixture was allowed to cool to about 53° C. over one hour, then to 45° C., and then at 20-25° C., while blowing nitrogen with a glass pipette overnight. The suspension was filtered via a medium pore-sized funnel. The solid was washed with a pre-cooled 10° C. mixed solvent of heptane/MTBE (1/2 vol/vol) and suction dried in hood overnight to give 4-bromomethyl-2-nitro-benzoic acid methyl ester as an off-white solid (66 g, 43% yield). The solid was used in the next step without further purification.

Step 2: A stirred mixture of 4-bromomethyl-2-nitro-benzoic acid methyl ester (66.3 g, 241.9 mmol), di-tert-butyl iminodicarboxylate (52.72 g, 242.6 mmol), cesium carbonate (161.58 g, 495.9 mmol), and lithium iodide (1.62 g, 12 mmol) in 2-butanone (700 mL) was heated to reflux in a 100° C. oil bath for 12 hours while stirred with a mechanical stirrer. The mixture was allowed to cool to room temperature. To the mixture, was added brine (300 mL), water (300 mL), and ethyl acetate (600 mL), and the mixture was stirred for 10 minutes. The suspension was filtered through a pad of Celite. The two layers were separated, and the organic layer was evaporated to a less volume. The aqueous layer was extracted with ethyl acetate (2×150 mL). The combined organic layers were washed with brine (1×500 mL), dried over magnesium sulfate while de-colored at the same time by charcoal at room temperature with stirring for 30 minutes. The black mixture was filtered through a pad of Celite, and the filtrate was evaporated to give 4-(di-tert-butoxycarbonylamino-methyl)-2-nitro-benzoic acid methyl ester as a brown oil (96.0 g, 96.7% yield). The product was used in the next step without further purification.

Step 3: To a stirred brown solution of 4-(di-tert-butoxycarbonylamino-methyl)-2-nitro-benzoic acid methyl ester (95.97 g, 233.8 mmol) in methylene chloride (800 mL), was added trifluoroacetic acid (33.87 mL, 455.9 mmol), and the mixture was stirred at room temperature overnight. Sat. sodium bicarbonate (500 mL) was added to the solution, and the mixture was stirred for 10 minutes. The organic layer was separated, dried over magnesium sulfate, and evaporated to give 4-(tert-butoxycarbonylamino-methyl)-2-nitro-benzoic acid methyl ester as a brown oil (64.36 g, 88% crude yield). The produce was used in the next step without further purification.

Step 4: A mixture of 4-(tert-butoxycarbonylamino-methyl)-2-nitro-benzoic acid methyl ester (64.36 g, 207.4 mmol), lithium hydroxide (5.96 g, 248.9 mmol) in methanol (500 mL) and water (250 mL) was stirred with a mechanical stirrer at room temperature overnight. The methanol was evaporated, and to the aqueous solution, was added 1 N HCl (300 mL) to form the precipitate. Ether (350 mL) was added, and the mixture was stirred at 0° C. for 2 hours. No desired precipitation was formed. The mixture was evaporated. To the mixture, was added water (500 mL). The aqueous layer was extracted with ethyl acetate (5×120 mL). The combined organic layers were separated, dried over magnesium sulfate, and concentrated to give 4-(tert-butoxycarbonylamino-methyl)-2-nitro-benzoic acid as a brown oil (56.69 g, 92% yield). The product was used in the next step without further purification.

Step 5: A mixture of 4-(tert-butoxycarbonylamino-methyl)-2-nitro-benzoic acid (56.57, 190.9 mmol) in methanol (250 mL) and palladium/carbon (5.66 g, 10% weight) was hydrogenated with a Parr-shaker overnight at 51 psi. The black mixture was filtered through a pad of Celite, and the filtrate was evaporated to give a brown oil, which was stirred in ether (300 mL) overnight. The ether slurry was filtered to give 2-amino-4-(tert-butoxycarbonylamino-methyl)-benzoic acid as a brown solid (42.0 g, 84% yield). The product was used in the next step without further purification.

Step 6: To a stirred solution of 2-amino-4-(tert-butoxycarbonylamino-methyl)-benzoic acid (24.75 g, 92.94 mmol), imidazole (7.59 g, 111.53 mmol) in acetonitrile (300 mL), was added acetyl chloride (7.96 mL, 111.53 mmol), and the mixture was stirred at room temperature overnight. To the mixture, was added 3-amino-piperidine-2,6-dione hydrogen chloride (15.30 g, 92.94 mmol), imidazole (12.66 g, 185.89 mmol) and triphenyl phosphite (29.23 mL, 111.53 mmol), and the mixture was heated to reflux for 6 hours. The mixture was cooled to room temperature and the brown mixture was filtered. The filtrate was evaporated and then purified by flash column chromatography (Silica gel, methanol/methylene chloride 4%/96%) to give [3-(2,6-dioxo-piperidin-3-yl)-2-methyl-4-oxo-3,4-dihydro-quinazolin-7-ylmethyl]-carbamic acid tert-butyl ester as a light yellow solid (24.57 g, 66% yield); HPLC, Waters Symmetry $C_{18}$, 5 µm, 3.9×150 mm, 1 mL/min, 240 nm, 10.90 $CH_3CN/0.1\%$ $H_3PO_4$, grad. to 95/5 in 5 min, kept 5 min, 5.97 min (99.7%); mp. 240-242° C.; $^1HNMR$ (DMSO-$d_6$) δ 1.29 (brs, 1H, CH from the BOC group), 1.409 (s, 8H, 3CH from the BOC group), 2.11-2.19 (m, 1H, CHH), 2.56-2.91 (m, 6H, $CHCH_2$, $CH_3$), 4.26 (d, J=6 Hz, 2H, $CH_2NH$), 5.25 (dd, J=5, 11 Hz, 1H, CH), 7.35-7.99 (m, 4H, Ar and $NHCH_2$), 11.02 (s, 1H, NH); $^{13}C$ NMR (DMSO-$d_6$) δ 20.97, 23.49, 28.19, 30.60, 43.22, 56.48, 78.00, 118.84, 123.99, 125.41, 126.00, 146.93, 147.55, 155.15, 155.81, 160.29, 169.51, 172.61. LCMS MH=401; Anal Calcd For $C_{20}H_{24}N_2O_5$: C, 59.99; H, 6.04; N, 13.99. Found: C, 59.78; H, 5.78; N, 13.85.

5.37 3-(7-aminomethyl-2-methyl-4-oxo-4H-quinazolin-3-yl)-piperidine-2,6-dione hydrogen chloride

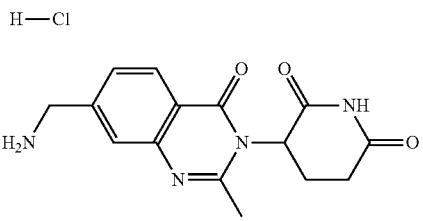 [SMILES: Cl ; Cc1nc2cc(CN)ccc2c(=O)n1C1CCC(=O)NC1=O]

Step 1: To a stirred brown solution of [3-(2,6-dioxopiperidin-3-yl)-2-methyl-4-oxo-3,4-dihydro-quinazolin-7-ylmethyl]-carbamic acid tert-butyl ester (14.7 g, 36.8 mmol) in methanol (200 mL) and methylene chloride (200 mL), was added 2 M HCl in ether (320 mL), and the mixture was stirred overnight. The solvent was evaporated, and the residue was stirred in ether (100 mL) for 2 hours. The suspension was filtered to give 3-(7-aminomethyl-2-methyl-4-oxo-4H-quinazolin-3-yl)-piperidine-2,6-dione hydrogen chloride as a light yellow solid (13.2 g, 106% crude yield). The product was used in the next step without further purification.

Step 2: 3-(7-Aminomethyl-2-methyl-4-oxo-4H-quinazolin-3-yl)-piperidine-2,6-dione hydro-chloride (1.00 g) was dissolved in water (100 mL). The solution was washed with ethyl acetate (2×100 mL). The aqueous layer was evaporated to give 3-(7-aminomethyl-2-methyl-4-oxo-4H-quinazolin-3-yl)-piperidine-2,6-dione hydrogen chloride as an off-white solid (0.86 g, 86% yield); HPLC, Waters Xterra RP 19, 5 μm, 3.9×150 mm, 1 mL/min, 240 nm, Waters LC Module 1, 05/95 $CH_3CN$/0.1% $(HCO_2)NH_4$, 6.27 min (98.7%); mp: 313-315° C.; $^1$HNMR (DMSO-$d_6$) δ 2.17-2.24 (m, 1H, CHH), 2.58-2.89 (m, 6H, CHCH$_2$, CH$_3$), 4.20 (q, J=5 Hz, 2H, ArCH$_2$), 5.34 (dd, J=6, 11 Hz, 1H, CH, hiding under the water peak), 7.64-8.09 (m, 3H, Ar), 8.72 (brs, 3H, ClNH$_3$), 11.07 (s, 1H, NH); $^{13}$C NMR (DMSO-$d_6$) δ 20.88, 22.97, 30.57, 41.69, 56.71, 119.61, 125.38, 126.42, 127.25, 141.34, 145.36, 156.66, 159.83, 169.25, 172.57. LCMS MH=301; Anal Calcd For $C_{15}H_{17}N_2O_3Cl$+1.0 $H_2O$ and +0.9 HCl: C, 46.48; H, 5.17; N, 14.45; Cl, 17.38. Found: C, 46.68; H, 5.15; N, 14.32; Cl, 17.05.

5.38 3-(2,8-dimethyl-4-oxo-4H-quinazolin-3-yl)-piperidine-2,6-dione

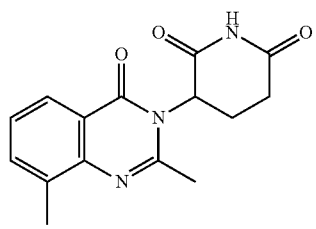 [SMILES: Cc1cccc2c(=O)n(C3CCC(=O)NC3=O)c(C)nc12]

To a stirred mixture of 2-amino-3-methylbenzoic acid (3.0 g, 20 mmol) and imidazole (1.6 g, 24 mmol) in acetonitrile (30 mL), was added acetyl chloride (1.7 mL, 24 mmol) at room temperature. The mixture was stirred at room temperature overnight. To the mixture, was added 3-aminopiperidine-2,6-dione hydrogen chloride (3.3 g, 20 mmol), imidazole (3.0 g, 68 mmol) and triphenyl phosphite (6.2 mL, 24 mmol) and heated to reflux for 22 hours. To the mixture, was added water (600 mL). The suspension was filtered and washed with water (2×100 mL), ethyl acetate (2×100 mL), sodium hydrogen carbonate (sat, 100 mL) and water (100 mL) to give a white solid, which was stirred in DMSO (20 mL) at 65° C. The mixture was polished filtered and washed with DMSO (10 mL). To the filtrate, was added water (100 mL) to give a suspension. The suspension was filtered and washed with water (2×50 mL) to give 3-(2,8-dimethyl-4-oxo-4H-quinazolin-3-yl)-piperidine-2,6-dione as a white solid (3.2 g, 56% yield): HPLC: Waters Symmetry $C_{18}$, 5 μm, 3.9×150 mm, 1 mL/min, 240 nm, 25/75 $CH_3CN$/0.1% $H_3PO_4$, 5.85 min (99.6%); mp: 296-298° C.; $^1$H NMR (DMSO-$d_6$) δ 2.12-2.24 (m, 1H, CHH), 2.51 (s, 3H, CH$_3$), 2.48-2.74 (m, 2H, 2CHH), 2.66 (s, 3H, CH$_3$), 2.76-2.01 (m, 1H, CHH), 5.27 (dd, J=6, 11 Hz, 1H, NCH), 7.38 (t, J=8 Hz, 1H, Ar), 7.67 (d, J=7 Hz, 1H, Ar), 7.86 (dd, J=0.6, 8 Hz, 1H, Ar), 11.02 (s, 1H, NH); $^{13}$C NMR (DMSO-$d_6$) δ 16.91, 20.91, 23.80, 30.60, 56.51, 120.23, 123.59, 126.05, 134.72, 134.94, 145.25, 153.82, 160.71, 169.51, 172.62; LCMS: MH=286; Anal Calcd for $C_{15}H_{15}N_3O_3$+0.2 $H_2O$: C, 62.36; H, 5.37; N, 14.54. Found: C, 62.21; H, 5.31; N, 14.43.

5.39 3-(8-fluoro-2-methyl-4-oxo-4H-quinazolin-3-yl)-piperidine-2,6-dione

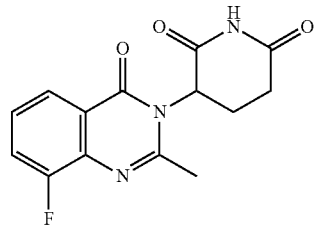 [SMILES: Cc1nc2c(F)cccc2c(=O)n1C1CCC(=O)NC1=O]

To a stirred mixture of 2-amino-3-fluorobenzoic acid (3.0 g, 19 mmol) and imidazole (1.6 g, 23 mmol) in acetonitrile (30 mL), was added acetyl chloride (1.7 mL, 23 mmol) at room temperature. The mixture was stirred at room temperature overnight. To the mixture, was added 3-aminopiperidine-2,6-dione hydrogen chloride (3.2 g, 19 mmol), imidazole (2.9 g, 43 mmol) and triphenyl phosphite (6.1 mL, 23 mmol) and heated to reflux for 22 hours. To the mixture, was added water (60 mL). The suspension was filtered and washed with water (2×50 mL), ethyl acetate (2×50 mL), and water (50 mL) to give a white solid, which was purified with preparative HPLC (C18 20/80 CH3CN/$H_2O$) to give a white solid. The white solid in DMSO (20 mL) was heated at 60° C. for 30 minutes. To the solution, was added water (10 mL). The suspension was cooled to room temperature. The suspension was filtered and washed with DMSO (4 mL) and water (20 mL) to give 3-(8-fluoro-2-methyl-4-oxo-4H-quinazolin-3-yl)-piperidine-2,6-dione as a white solid (3.11 g, 67% yield): HPLC: Waters Symmetry $C_{18}$, 5 μm, 3.9×150 mm, 1 mL/min, 240 nm, 20/80 $CH_3CN$/0.1% $H_3PO_4$, 4.7 min (99.7%); mp: 305° C. (decomp); $^1$H NMR (DMSO-$d_6$) δ 2.16-2.23 (m, 1H, CHH), 2.43-2.76 (m, 5H, CH$_3$, 2CHH), 2.79-2.92 (m, 1H, CHH), 5.32 (dd, J=6, 11 Hz, 1H, NCH), 7.46-7.53 (m, 1H, Ar), 7.67-7.73 (m, 1H, Ar), 7.84-7.94 (m, 1H, Ar), 11.06 (s, 1H, NH); $^{13}$C NMR (DMSO-$d_6$) δ 20.80, 23.67, 30.58, 56.71, 120.04 (d, $J_{C-F}$=19 Hz), 121.71 (d, $J_{C-F}$32 4 Hz), 122.31, 126.91 (d, $J_{C-F}$=8 Hz), 136.04 (d, $J_{C-F}$=12 Hz), 155.93 (d, $J_{C-F}$=254 Hz), 155.93, 159.62 (d, $J_{C-F}$=3 Hz), 169.32, 172.57: LCMS: MH=290; Anal Calcd for $C_{14}H_{12}N_3O_3F$: C, 58.13; H, 4.18; N, 14.53; F, 6.57. Found: C, 57.87; H, 3.94; N, 14.35; F, 6.91.

5.40 3-(8-chloro-2-methyl-4-oxo-4H-quinazolin-3-yl)-piperidine-2,6-dione

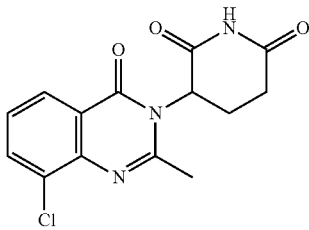

To a stirred mixture of 2-amino-3-chlorobenzoic acid (2.2 g, 13 mmol) and imidazole (1.1 g, 16 mmol) in acetonitrile (30 mL), was added acetyl chloride (1.1 mL, 16 mmol) at room temperature. The mixture was stirred at room temperature overnight. To the mixture, was added 3-amino-piperidine-2,6-dione hydrogen chloride (2.3 g, 14 mmol), imidazole (1.9 g, 28 mmol) and triphenyl phosphite (4.0 mL, 15 mmol) and heated to reflux for 22 hours. To the mixture, was added water (60 mL). The suspension was filtered and washed with water (2×50 mL), ethyl acetate (2×50 mL), and water (50 mL) to give a white solid, which was stirred in methanol (50 mL) overnight. The suspension was filtered and washed with methanol (30 mL) and water (30 mL) to give 3-(8-chloro-2-methyl-4-oxo-4H-quinazolin-3-yl)-piperidine-2,6-dione as a white solid (1.5 g, 38% yield): HPLC: Waters Symmetry $C_{18}$, 5 μm, 3.9×150 mm, 1 mL/min, 240 nm, 25/75 $CH_3CN$/0.1% $H_3PO_4$, 6.51 min (99.6%); mp: 290-292° C.; $^1$H NMR (DMSO-$d_6$) δ 2.16-2.23 (m, 1H, CHH), 2.59-2.69 (m, 5H, $CH_3$, 2CHH), 2.79-2.87 (m, 1H, CHH), 5.32 (dd, J=5, 11 Hz, 1H, NCH), 7.48 (t, J=8 Hz, 1H, Ar), 7.96-8.02 (m, 2H, Ar), 11.07 (s, 1H, NH); $^{13}$C NMR (DMSO-$d_6$) δ 20.68, 23.75, 30.51, 56.68, 121.87, 125.08, 126.91, 130.03, 134.69, 143.14, 156.14, 159.88, 169.23, 172.51; LCMS: MH=306, 308; Anal Calcd for $C_{14}H_{12}N_3O_3Cl$: C, 55.00; H, 3.96; N, 13.74; Cl, 11.60. Found: C, 54.73; H, 3.96; N, 13.58; Cl, 11.03.

5.41 3-(8-bromo-2-methyl-4-oxo-4H-quinazolin-3-yl)-piperidine-2,6-dione

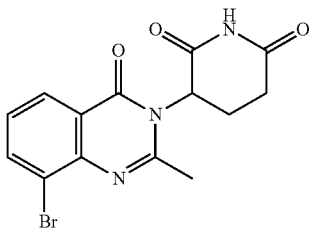 [SMILES: Cc1nc2c(Cl)cccc2c(=O)n1C1CCC(=O)NC1=O]

To a stirred mixture of 2-amino-3-bromobenzoic acid (1.0 g, 4.6 mmol) and imidazole (0.38 g, 5.5 mmol) in acetonitrile (10 mL), was added acetyl chloride (0.6 mL, 8.3 mmol) at room temperature. The mixture was stirred at room temperature overnight. To the mixture, was added 3-amino-piperidine-2,6-dione hydrogen chloride (0.76 g, 4.6 mmol), imidazole (0.7 g, 10 mmol) and triphenyl phosphite (1.5 mL, 5.6 mmol) and heated to reflux for 22 hours. To the mixture, was added water (60 mL). The suspension was filtered and washed with water (2×50 mL), ethyl acetate (2×50 mL), and water (50 mL) to give 3-(8-bromo-2-methyl-4-oxo-4H-quinazolin-3-yl)-piperidine-2,6-dione as a white solid (0.34 g, 21% yield): HPLC: Waters Symmetry $C_{18}$, 5 μm, 3.9×150 mm, 1 mL/min, 240 nm, 25/75 $CH_3CN$/0.1% $H_3PO_4$, 9.47 min (99.6%); mp: 307-309° C.; $^1$H NMR (DMSO-$d_6$) δ 2.16-2.23 (m, 1H, CHH), 2.58-2.67 (m, 2H, 2CHH), 2.68 (s, 3H, $CH_3$), 2.76-2.92 (m, 1H, CHH), 5.31 (dd, J=5, 11 Hz, 1H, NCH), 7.41 (t, J=8 Hz, 1H, Ar), 8.04 (dd, J=2, 8 Hz 1H, Ar), 8.15 (dd, J=1, 8 Hz 1H, Ar), 11.07 (s, 1H, NH); $^{13}$C NMR (DMSO-$d_6$) δ 20.73, 23.85, 30.57, 56.76, 121.09, 121.82, 125.86, 127.47, 138.08, 144.23, 156.23, 159.97, 169.29, 172.58; LCMS: MH=350, 352; Anal Calcd for $C_{14}H_{12}N_4O_4Br$: C, 48.02; H, 3.45; N, 12.00; Br, 22.82. Found: C, 47.74; H, 3.23; N, 11.85; Br, 22.42.

5.42 3-(8-hydroxy-2-methyl-4-oxo-4H-quinazolin-3-yl)-piperidine-2,6-dione

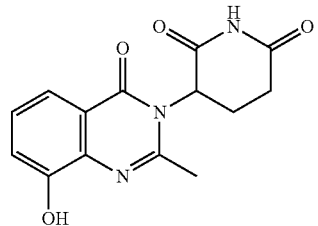 [SMILES: Cc1nc2c(O)cccc2c(=O)n1C1CCC(=O)NC1=O]

To a stirred mixture of 2-amino-3-hydroxybenzoic acid (2.0 g, 13.1 mmol) and imidazole (2.0 g, 29.4 mmol) in acetonitrile (30 mL), was added acetyl chloride (2.0 mL, 28.7 mmol) at room temperature. The mixture was stirred at room temperature overnight. To the mixture, was added 3-amino-piperidine-2,6-dione hydrogen chloride (2.2 g, 13.1 mmol), imidazole (2.0 g, 29.4 mmol) and triphenyl phosphite (4.11 mL, 15.7 mmol) and heated to reflux for 22 hours. To the mixture, was added water (60 mL) and conc HCl until pH ~1. The solvent was removed in vacuo. To the residue, was added water (50 mL). The aqueous layer was extracted with ethyl acetate (2×50 mL). To the aqueous layer, was added sodium hydrogen carbonate (1.8 g) to pH=7-8, and the mixture was stirred at room temperature to give a suspension. The suspension was filtered to give 3-(8-hydroxy-2-methyl-4-oxo-4H-quinazolin-3-yl)-piperidine-2,6-dione as an off-white solid (0.6 g, 16% yield): HPLC: Waters Symmetry $C_{18}$, 5 μm, 3.9×150 mm, 1 mL/min, 240 nm, 20/80 $CH_3CN$/0.1% $H_3PO_4$, 3.03 min (99.3%); mp: 266-268° C.; $^1$H NMR (DMSO-$d_6$) δ 2.10-2.22 (m, 1H, CHH), 2.57-2.72 (m, 5H, $CH_3$, 2CHH), 2.78-2.92 (m, 1H, CHH), 5.25 (dd, J=5, 11 Hz, 1H, NCH), 7.19 (dd, J=1, 8 Hz, 1H, Ar), 7.30 (t, J=8 Hz, 1H, Ar), 7.45 (dd, J=1, 8 Hz, 1H, Ar), 9.65 (s, 1H, OH), 11.02 (s, 1H, NH); $^{13}$C NMR (DMSO-$d_6$) δ 20.92, 23.37, 30.59, 56.45, 115.62, 118.51, 121.19, 127.05, 135.91, 152.34, 153.09, 160.45, 169.52, 172.62; LCMS: MH=288; Anal Calcd for $C_{14}H_{13}N_3O_4$+1 $H_2O$: C, 55.08; H, 4.95; N, 13.76. Found: C, 54.88; H, 4.97; N, 13.77.

5.43 3-(2-methyl-4-oxo-8-trifluoromethyl-4H-quinazolin-3-yl)-piperidine-2,6-dione

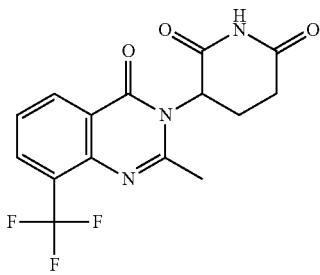 [SMILES: Cc1nc2c(C(F)(F)F)cccc2c(=O)n1C1CCC(=O)NC1=O]

To a stirred mixture of 2-amino-3-(trifluoromethyl)benzoic acid (2.0 g, 9.8 mmol) and imidazole (0.8 g, 12 mmol) in acetonitrile (20 mL), was added acetyl chloride (0.83 mL, 12 mmol) at room temperature. The mixture was stirred at room temperature overnight. To the mixture, was added 3-amino-piperidine-2,6-dione hydrogen chloride (1.6 g, 9.8 mmol), imidazole (1.5 g, 22 mmol) and triphenyl phosphite (3.1 mL, 12 mmol) and heated to reflux for 22 hours. To the mixture, was added water (60 mL). The suspension was filtered and washed with water (2×50 mL), ethyl acetate (2×50 mL), sodium hydrogen carbonate (sat, 50 mL) and water (50 mL) to give 3-(2-methyl-4-oxo-8-trifluoromethyl-4H-quinazolin-3-yl)-piperidine-2,6-dione as a white solid (0.32 g, 10% yield): HPLC: Waters Symmetry $C_{18}$, 5 µm, 3.9×150 mm, 1 mL/min, 240 nm, 35/65 $CH_3CN/0.1\%$ $H_3PO_4$, 7.57 min (99.8%); mp: 351-353° C.; $^1H$ NMR (DMSO-$d_6$) δ 2.19-2.26 (m, 1H, CHH), 2.59-2.70 (m, 5H, $CH_3$2CHH), 2.81-2.93 (m, 1H, CHH), 5.34 (dd, J=5, 11 Hz, 1H, NCH), 7.64 (t, J=8 Hz, 1H, Ar), 8.20 (d, J=8 Hz 1H, Ar), 8.31 (d, J=8 Hz, 1H, Ar), 11.09 (s, 1H, NH); $^{13}C$ NMR (DMSO-$d_6$) δ 20.67, 24.05, 30.57, 56.84, 121.48, 123.52 (q, $J_{C-F}$=274 Hz), 124.77 (q, $J_{C-F}$=30 Hz), 125.98, 130.74, 132.29 (q, $J_{C-F}$=5 Hz), 144.20, 156.71, 159.68, 169.28, 172.58; LCMS: MH=340; Anal Calcd for $C_{15}H_{12}N_3O_3F_3$=0.3 $H_2O$+0.1 $CH_3CN$: C, 52.34; H, 3.72; N, 12.45; F, 16.34. Found: C, 52.71; H, 3.52; N, 12.31; F, 15.99.

5.44 3-(8-methyl-4-oxo-4H-quinazolin-3-yl)-piperidine-2,6-dione

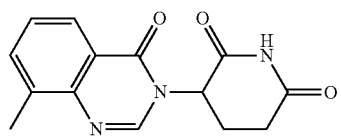 [SMILES: Cc1cccc2c(=O)n(C3CCC(=O)NC3=O)cnc12]

Step 1: A mixture of 2-amino-3-methylbenzoic acid (2.1 g, 14 mmol) and CDI (1.9 g, 12 mmol) in acetonitrile (25 mL) was stirred at room temperature for 5 hours. To the suspension, was added 3-amino-piperidine-2,6-dione hydrogen chloride (2.3 g, 14 mmol), triethylamine (7.2 mL, 66 mmol) and acetic acid (8 mL, 132 mmol), and the mixture was heated to reflux for 16 hours. To the mixture, was added water (75 mL) and stirred at room temperature for 2 hours. The suspension was filtered and washed with water (50 mL) and ethyl acetate (20 mL) to give 2-amino-N-(2,6-dioxo-piperidin-3-yl)-3-methyl-benzamide as a white solid (1.9 g, 61% yield): $^1H$ NMR (DMSO-$d_6$) δ 1.92-1.99 (m, 1H, CHH), 2.06 (s, 3H, $CH_3$), 2.04-2.14 (m, 1H, CHH), 2.51-2.56 (m, 1H, CHH), 2.73-2.85 (m, 1H, CHH), 4.69-4.78 (m, 1H, NCH), 6.22 (brs, 2H, $NH_2$), 6.50 (t, J=8 Hz, 1H, Ar), 7.10 (d, J=8 Hz, 1H, Ar), 7.40 (d, J=8 Hz, 1H, Ar), 8.47 (d, J=8 Hz, 1H, NH), 10.83 (s, 1H, NH); LCMS: MH=262.

Step 2: A stirred solution of 2-amino-N-(2,6-dioxo-piperidin-3-yl)-3-methyl-benzamide (0.9 g, 3.4 mmol) and trimethyl orthoformate (4.5 mL) and p-toluene sulfonic acid (250 mg) in acetonitrile (20 mL) was heated to reflux for 17 hours. To the mixture, was added water (75 mL) and stirred for 20 minutes. The suspension was filtered and washed with methanol (20 mL), water (20 mL) and ethyl acetate (20 mL) to give a purple solid. The solid in NMP (4 mL) was heated at 80° C. for 30 minutes. To the solution, was added water (1 mL), and the mixture was allowed to cool to room temperature. To the solution, was added water (1 mL), and the mixture was allowed to cool to room temperature. The suspension was filtered and washed with water (30 mL) to give 3-(8-methyl-4-oxo-4H-quinazolin-3-yl)-piperidine-2,6-dione as a light purple solid (660 mg, 72% yield): HPLC: Waters Symmetry $C_{18}$, 5 µm, 3.9×150 mm, 1 mL, 240 nm, 30/70 $CH_3CN/0.1\%$ $H_3PO_4$, 3.07 min (98.6%); mp: 290-292° C.; $^1H$ NMR (DMSO-$d_6$) δ 2.11-2.19 (m, 1H, CHH), 2.56 (s, 3H, $CH_3$), 2.62-2.93 (m, 3H, $CH_2$CHH), 5.48 (br, 1H, NCH), 7.46 (t, J=8 Hz, 1H, Ar), 7.73 (d, J=8 Hz, 1H, Ar), 7.99 (d, J=8 Hz, 1H, Ar), 8.38 (s, 1H, CH), 11.16 (s, 1H, NH); $^{13}C$ NMR (DMSO-$d_6$) δ 17.01, 22.53, 30.97, 5.22, 121.36, 123.79, 126.51, 126.86, 135.03, 135.47, 136.39, 145.96, 146.36, 159.97, 169.92, 172.52; LCMS: MH=272; Anal Calcd for $C_{14}H_{13}N_3O_3$: C, 61.99; H, 4.83; N, 15.49. Found: C, 61.70; H, 4.68; N, 15.40.

5.45 3-(6,7-dimethoxy-2-methyl-4-oxo-4-H-quinazolin-3-yl)-piperidine-2,6-dione

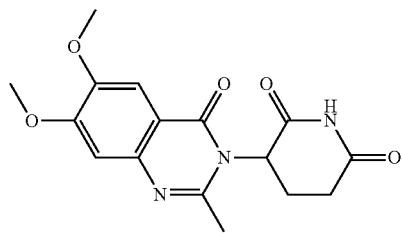 [SMILES: COc1cc2nc(C)n(C3CCC(=O)NC3=O)c(=O)c2cc1OC]

To a stirred mixture of 2-amino-4,5-dimethoxybenzoic acid (5.0 g, 25 mmol) and imidazole (2.1 g, 30 mmol) in acetonitrile (50 mL), was added acetyl chloride (2.2 mL, 30 mmol) at room temperature. The mixture was stirred at room temperature overnight. To the mixture, was added 3-amino-piperidine-2,6-dione hydrogen chloride (4.2 g, 25 mmol), imidazole (3.8 g, 56 mmol) and triphenyl phosphite (7.3 mL, 28 mmol) and heated to reflux for 22 hours. The suspension was filtered and washed with acetonitrile (50 mL) and water (2×50 mL) to give a solid. The solid was stirred in sodium hydrogen carbonate (sat, 50 mL), and water (50 mL) for 1 hour. The suspension was filtered and washed with water (2×50 mL) and ethyl acetate (30 mL) to give 3-(6,7-dimethoxy-2-methyl-4-oxo-4H-quinazolin-3-yl)-piperidine-2,6-dione as a white solid (5.7 g, 68% yield): HPLC: Waters Symmetry $C_{18}$, 5 µm, 3.9×150 mm, 1 mL/min, 240 nm, 20/80 $CH_3CN/0.1\%$ $H_3PO_4$, 3.26 min (99.8%); mp: 325° C. (decomp); $^1H$ NMR (DMSO-$d_6$) δ 2.15-2.19 (m, 1H, CHH), 2.56-2.88 (m, 6H, $CH_3$, $CH_2$, CH), 3.85 (s, 3H, $CH_3$), 3.90 (s, 3H, $CH_3$), 5.22 (dd, J=5, 11 Hz, 1H, NCH), 7.09 (s, 1H, Ar), 7.35 (s, 1H, Ar), 10.99 (s, 1H, NH); $^{13}$C NMR (DMSO-$d_6$) δ 21.12, 23.21, 30.62, 55.63, 55.97, 56.38, 104.98, 107.31, 113.27, 143.09, 148.40, 153.24, 154.83, 159.76, 169.61, 172.64; LCMS: MH=332; Anal Calcd for $C_{16}H_{17}N_3O_5$: C, 58.00; H, 5.17; N, 12.68. Found: C, 57.88; H, 5.06; N, 12.77.

5.46 3-(6,8-dichloro-2-methyl-4-oxo-4H-quinazolin-3-yl)-piperidine-2,6-dione

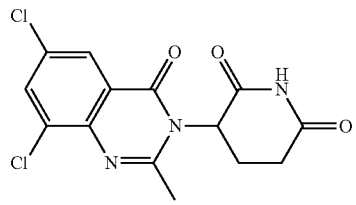 [SMILES: Cc1nc2c(Cl)cc(Cl)cc2c(=O)n1C1CCC(=O)NC1=O]

To a stirred mixture of 2-amino-3,5-dichlorobenzoic acid (5.0 g, 24 mmol) and imidazole (1.9 g, 28 mmol) in acetonitrile (60 mL), was added acetyl chloride (2.0 mL, 28 mmol) at room temperature. The mixture was stirred at room temperature overnight. To the mixture, was added 3-amino-piperidine-2,6-dione hydrogen chloride (3.9 g, 24 mmol), imidazole (3.5 g, 52 mmol) and triphenyl phosphite (6.8 mL, 26 mmol) and heated to reflux for 22 hours. The suspension was filtered and washed with acetonitrile (30 mL), water (2×30 mL), and ethyl acetate (30 mL) to give 3-(6,8-dichloro-2-methyl-4-oxo-4H-quinazolin-3-yl)-piperidine-2,6-dione as a white solid (4.65 g, 58% yield): HPLC: Waters Symmetry $C_{18}$, 5 μm, 3.9×150 mm, 1 mL/min, 240 nm, 40/60 $CH_3CN$/0.1% $H_3PO_4$, 4.78 min (100%); mp: 238-240° C.; $^1$H NMR (DMSO-$d_6$) δ 2.15-2.22 (m, 1H, CHH), 2.55-2.69 (m, 5H, $CH_3$, 2CHH), 2.78-2.91 (m, 1H, CHH), 5.33 (dd, J=6, 11 Hz, 1H, NCH), 7.96 (d, J=2 Hz, 1H, AR), 8.15 (d, J=2 Hz, 1H, Ar), 11.09 (s, 1H, NH); $^{13}$C NMR (DMSO-$d_6$) δ 20.63, 23.85, 30.54, 56.92, 122.55, 24.24, 130.51, 131.72, 134.38, 142.25, 156.80, 159.07, 169.12, 172.53; LCMS: MH=340, 342; Anal Calcd for $C_{14}H_{11}N_3O_3Cl_3$: C, 49.43; H, 3.26; N, 12.35; Cl, 20.84. Found: C, 49.21; H, 3.11; N, 12.30; Cl, 19.43.

5.47 3-(2-methyl-4-oxo-4H-benzo[g]quinazolin-3-yl)-piperidine-2,6-dione

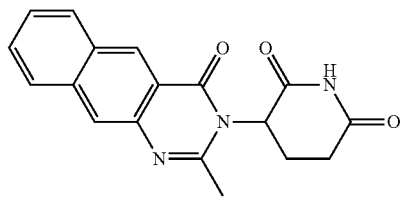 [SMILES: Cc1nc2cc3ccccc3cc2c(=O)n1C1CCC(=O)NC1=O]

To a stirred mixture of 3-amino-3-naphtholic acid (5.4 g, 29 mmol) and imidazole (2 g, 29 mmol) in acetonitrile (60 mL), was added acetyl chloride (2.1 mL, 29 mmol) at room temperature. The mixture was stirred at room temperature overnight. To the mixture, was added 3-amino-piperidine-2,6-dione hydrogen chloride (4 g, 25 mmol), imidazole (3.7 g, 54 mmol) and triphenyl phosphite (7.1 mL, 27 mmol) and heated to reflux for 22 hours. The suspension was filtered and washed with acetonitrile (30 mL), water (2×30 mL), and ethyl acetate (30 mL) to give 3-(2-methyl-4-oxo-4H-benzo[g]quinazolin-3-yl)-piperidine-2,6-dione as a pale white solid (6.3 g, 79% yield): HPLC: Waters Symmetry $C_{18}$, 5 μm, 3.9×150 mm, 1 mL/min, 240 nm, 30/70 $CH_3CN$/0.1% $H_3PO_4$, 4.59 min (99.7%); mp: 307° C. (decomp); $^1$H NMR (DMSO-$d_6$) δ 2.17-2.26 (m, 1H, CHH), 2.60-2.94 (m, 6H, $CH_3$, $CH_2$, CHH), 5.29 (dd, J=5, 11 Hz, 1H, NCH), 7.55-7.60 (m, 1H, Ar), 7.64-7.69 (m, 1H, Ar), 8.09 (d, J=8 Hz, 1H, Ar), 8.18-8.20 (m, 2H, Ar), 8.75 (s, 1H, Ar), 11.06 (s, 1H, NH); $^{13}$C NMR (DMSO-$d_6$) δ 21.16, 23.60, 30.71, 56.45, 119.52, 123.86, 126.25, 127.47, 127.77, 128.58, 129.24, 129.53, 136.26, 142.20, 153.87, 160.97, 169.70, 172.68; LCMS: MH=322; Anal Calcd for $C_{18}H_{15}N_3O_3$+0.1 $H_2O$; C, 66.91; H, 4.74; N, 13.00. Found: C, 66.78; H, 4.76; N, 12.95.

5.48 Assays

5.48.1 TNFα Inhibition Assay in PMBC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/ml penicillin, and 100 μg/ml streptomycin (Life Technologies).

PBMC (2×10$^5$ cells) are plated in 96-well flat-bottom Costar tissue culture plates (Corning, N.Y., USA) in triplicate. Cells are stimulated with LPS (from Salmonella abortus equi, Sigma cat. no. L-1887, St. Louis, Mo., USA) at 1 ng/ml final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% $CO_2$, and supernatants are then collected, diluted with culture medium and assayed for TNFα levels by ELISA (Endogen, Boston, Mass., USA). IC$_{50}$s are calculated using non-linear regression, sigmoidal dose-response, constraining the top to 100% and bottom to 0%, allowing variable slope (GraphPad Prism v3.02).

5.48.2 IL-2 and MIP-3α Production by T Cells

PBMC are depleted of adherent monocytes by placing 1×10$^8$ PBMC in 10 ml complete medium (RPMI 1640 supplemented with 10% heat-inactivated fetal bovine serum, 2 mM L-glutamine, 100 U/ml penicillin, and 100 μg/ml streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every 1×10$^8$ non-adherent PBMC: 0.3 ml Sheep anti-mouse IgG beads, 15 μl anti-CD16, 15 μl anti-CD33, 15 μl anti-CD56, 0.23 ml anti-CD19 beads, 0.23 ml anti-HLA class II beads, and 56 μl anti-CD14 beads. The cells and bead/antibody mixture is rotated end-over-end for 30-60 minutes at 4° C. Purified T cells are removed from beads using a Dynal magnet. Typical yield is about 50% T cells, 87-95% CD3° by flow cytometry.

Tissue culture 96-well flat-bottom plates are coated with anti-CD3 antibody OKT3 at 5 μg/ml in PBS, 100 μl per well, incubated at 37° C. for 3-6 hours, then washed four times with complete medium 100 μl/well just before T cells are added. Compounds are diluted to 20 times of final in a round bottom tissue culture 96-well plate. Final concentrations are about 10 µM to about 0.00064 µM. A 10 mM stock of compounds provided herein is diluted 1:50 in complete for the first 20× dilution of 200 µM in 2% DMSO and serially diluted 1:5 into 2% DMSO. Compound is added at 10 µl per 200 µl culture, to give a final DMSO concentration of 0.1%. Cultures are incubated at 37° C., 5% $CO_2$ for 2-3 days, and supernatants analyzed for IL-2 and MIP-3α by ELISA (R&D Systems). IL-2 and MIP-3α levels are normalized to the amount produced in the presence of an amount of a compound provided herein, and $EC_{50}$s calculated using non-linear regression, sigmoidal dose-response, constraining the top to 100% and bottom to 0%, allowing variable slope (GraphPad Prism v3.02).

5.48.3 Cell Proliferation Assay

Cell lines Namalwa, MUTZ-5, and UT-7 are obtained from the Deutsche Sammlung von Mikroorganismen und Zellkulturen GmbH (Braunschweig, Germany). The cell line KG-1 is obtained from the American Type Culture Collection (Manassas, Va., USA). Cell proliferation as indicated by $^3$H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 µM in a final concentration of about 0.25% DMSO in triplicate at 37° C. in a humidified incubator at 5% $CO_2$ for 72 hours. One microcurie of $^3$H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 µl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope, (GraphPad Prism v3.02).

5.48.4 Immunoprecipitation and Immunoblot

Namalwa cells are treated with DMSO or an amount of a compound provided herein for 1 hour, then stimulated with 10 U/ml of Epo (R&D Systems) for 30 minutes. Cell lysates are prepared and either immunoprecipitated with Epo receptor Ab or separated immediately by SDS-PAGE. Immunoblots are probed with Akt, phospo-Akt (Ser473 or Thr308), phospho-Gab1 (Y627), Gab1, IRS2, actin and IRF-1 Abs and analyzed on a Storm 860 Imager using ImageQuant software (Molecular Dynamics).

5.48.5 Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

5.48.6 Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 minutes. Samples are analyzed using flow cytometry.

5.48.7 Luciferase Assay

Namalwa cells are transfected with 4 µg of AP1-luciferase (Stratagene) per 1×10$^6$ cells and 3 µl Lipofectamine 2000 (Invitrogen) reagent according to manufacturer's instructions. Six hours post-transfection, cells are treated with DMSO or an amount of a compound provided herein. Luciferase activity is assayed using luciferase lysis buffer and substrate (Promega) and measured using a luminometer (Turner Designs).

5.48.8 Anti-Proliferation Assay

Day 1: The cells are seeded to 96-well plate with 50 µl/well in 10% FBS RPMI (w/Glutamine, w/o pen-strip) for overnight. The following cells are used:
  Colorectal cancer cell: Colo 205 3200 cells/well; positive control irinotecan
  Pancreatic cancer cell: BXPC-3 1200 cells/well; positive control gemcitabine
  Prostate cancer cell: PC3 1200 cells/well; positive control docetaxel
  Breast cancer cell: MDA-MB-231 2400 cells/well; positive control paclitaxel Day 2: The compounds are serially diluted from 0.00001 µm~10 µm (or 0.000001~1 µM) with 50 µl/well (of 2×) and added to the plates in duplicate with relative positive control. The plates were then incubated at 37° C. for 72 hours.

Day 5: The results are detected by CellTiter Glo method. 100 µl/well of CellTiter Glo reagent is added to the plates and incubated for 10 minutes at room temperature, and then analyzed on the Top Count reader. The $IC_{50}$ of each compound is typically based on the result of two or more individually experiments.

5.49 TNFα Inhibition

Abilities of certain compounds for inhibiting TNFα were determined using procedures substantially similar to those described in Section 5.48.1, above.

The tested compounds included: 3-(7-amino-2-methyl-4-oxo-4H-quinazolin-3-yl)-piperidine-2,6-dione; 3-(2,7-dimethyl-4-oxo-4H-quinazolin-3-yl)-piperidine-2,6-dione; 3-(2,8-dimethyl-4-oxo-4H-quinazolin-3-yl)-piperidine-2,6-dione; 3-(6,7-dimethoxy-2-methyl-4-oxo-4H-quinazolin-3-yl)-piperidine-2,6-dione; 3-(7-fluoro-2-methyl-4-oxo-4H-quinazolin-3-yl)-piperidine-2,6-dione; 3-(7-chloro-2-methyl-4-oxo-4H-quinazolin-3-yl)-piperidine-2,6-dione; 3-(7-bromo-2-methyl-4-oxo-4H-quinazolin-3-yl)-piperidine-2,6-dione; 3-(8-bromo-2-methyl-4-oxo-4H-quinazolin-3-yl)-piperidine-2,6-dione; 3-(8-hydroxy-2-methyl-4-oxo-4H-quinazolin-3-yl)-piperidine-2,6-dione; 3-(2-methyl-4-oxo-8-trifluoromethyl-4H-quinazolin-3-yl)-piperidine-2,6-dione; heptanoic acid [3-(2,6-dioxo-piperidin-3-yl)-2-methyl-4-oxo-3,4-dihydro-quinazolin-6-ylmethyl]-amide; cyclopropanecarboxylic acid [3-(2,6-dioxo-piperidin-3-yl)-2-methyl-4-oxo-3,4-dihydro-quinazolin-6-ylmethyl]-amide; 2-(4-chloro-phenyl)-N-[3-(2,6-dioxo-piperidin-3-yl)-2-methyl-4-oxo-3,4-dihydro-quinazolin-6-ylmethyl]-acetamide; 1-[3-(2,6-dioxo-piperidin-3-yl)-2-methyl-4-oxo-3,4-dihydro-quinazolin-6-ylmethyl]-3-hexyl-urea; 1-(4-chloro-phenyl)-3-[3-(2,6-dioxo-piperidin-3-yl)-2-methyl-4-oxo-3,4-dihydro-quinazolin-6-ylmethyl]-urea; 1-[3-(2,6-dioxo-piperidin-3-yl)-2-methyl-4-oxo-3,4-dihydro-quinazolin-6-ylmethyl]-3-m-tolyl-urea; 1-[3-(2,6-dioxo-piperidin-3-yl)-2-methyl-4-oxo-3,4-dihydro-quinazolin-6-ylmethyl]-3-(4-trifluoromethoxy-phenyl)-urea; N-[3-(2,6-dioxo-piperidin-3-yl)-2-methyl-4-oxo-3,4-dihydro-quinazolin-6-ylmethyl]-4-trifluoromethyl-sulfanyl/benzamide; 1-(3-chloro-4-methyl-phenyl)-3-[3-(2,6-dioxo-piperidin-3-yl)-2-methyl- 4-oxo-3,4-dihydro-quinazolin-6-ylmethyl]-urea; 4-chloro-N-[3-(2,6-dioxo-piperidin-3-yl)-2-methyl-4-oxo-3,4-dihydro-quinazolin-6-ylmethyl]-benzamide; N-[3-(2,6-dioxo-piperidin-3-yl)-2-methyl-4-oxo-3,4-dihydro-quinazolin-6-ylmethyl]-3-trifluoromethyl-benzamide; N-[3-(2,6-dioxo-piperidin-3-yl)-2-methyl-4-oxo-3,4-dihydro-quinazolin-6-ylmethyl]-4-trifluoromethoxy-benzamide; 3,4-dichloro-N-[3-(2,6-dioxo-piperidin-3-yl)-2-methyl-4-oxo-3,4-dihydro-quinazolin-5-ylmethyl]-benzamide; and N-[3-(2,6-dioxo-piperidin-3-yl)-2-methyl-4-oxo-3,4-dihydro-quinazolin-6-ylmethyl]-4-trifluoromethyl-benzamide. From the tests, it was determined that IC$_{50}$ values of the tested compounds were in the range of 0.01 to 25 µM.

5.50 IL-2 Production

Abilities of certain compounds for stimulating the production of IL-2 were determined using procedures substantially similar to those described in Section 5.48.2, above.

The tested compounds included: 3-(6-amino-2-methyl-4-oxo-4H-quinazolin-3-yl)-piperidine-2,6-dione; 3-(7-amino-2-methyl-4-oxo-4H-quinazolin-3-yl)-piperidine-2,6-dione; 3-(7-fluoro-2-methyl-4-oxo-4H-quinazolin-3-yl)-piperidine-2,6-dione; 3-(7-chloro-2-methyl-4-oxo-4H-quinazolin-3-yl)-piperidine-2,6-dione; 3-(7-bromo-2-methyl-4-oxo-4H-quinazolin-3-yl)-piperidine-2,6-dione; 3-(6-hydroxy-2-methyl-4-oxo-4H-quinazolin-3-yl)-piperidine-2,6-dione; 1-[3-(2,6-dioxo-piperidine-3-yl)-2-methyl-4-oxo-3,4-dihydro-quinazolin-6-ylmethyl]-3-hexyl-urea; and 1-[3-(2,6-dioxo-piperidin-3-yl)-2-methyl-4-oxo-3,4-dihydro-quinazolin-6-ylmethyl]-3-(4-trifluoromethylphenyl)-urea. From the tests, it was determined that EC$_{50}$ values of the tested compounds were in the range of 0.1 to 3.5 µM

5.51 Cell Proliferation

Abilities of certain compounds for inhibiting proliferation of Namalwa AG4 cells were determined using procedures substantially similar to those described in Section 5.48.3, above.

The tested compounds included: 3-(6-amino-2-methyl-4-oxo-4H-quinazolin-3-yl)-piperidine-2,6-dione; 3-(7-amino-2-methyl-4-oxo-4H-quinazolin-3-yl)-piperidine-2,6-dione; 3-(7-fluoro-2-methyl-4-oxo-4H-quinazolin-3-yl)-piperidine-3,6-dione; 3-(7-chloro-2-methyl-4-oxo-4H-quinazolin-3-yl)-piperidine-2,6-dione; 3-(7-bromo-2-methyl-4-oxo-4H-quinazolin-3-yl)-piperidine-2,6-dione; heptanoic acid [3-(2,6-dioxo-piperidin-3-yl)-2-methyl-4-oxo-3,4-dihydro-quinazolin-6-ylmethyl]-amide; 2-(4-chloro-phenyl)-N-[3-(2,6-dioxo-piperidin-3-yl)-2-methyl-4-oxo-3,4-dihydro-quinazolin-6-ylmethyl]-acetamide; 1-[3-(2,6-dioxo-piperidin-3-yl)-2-methyl-4-oxo-3,4-dihydro-quinazolin-6-ylmethyl]-3-hexyl-urea; 1-(4-chloro-phenyl)-3-[3-(2,6-dioxo-piperidin-3-yl)-2-methyl-4-oxo-3,4-dihydro-quinazolin-6-ylmethyl]-urea; 1-[3-(2,6-dioxo-piperidin-3-yl)-2-methyl-4-oxo-3,4-dihydro-quinazolin-6-ylmethyl]-3-m-tolyl-urea; 1-[3-(2,6-dioxo-piperidin-3-yl)-2-methyl-4-oxo-3,4-dihydro-quinazolin-6-ylmethyl]-3-(4-trifluoromethoxy-phenyl)-urea; N-[3-(2,6-dioxo-piperidin-3-yl)-2-methyl-4-oxo-3,4-dihydro-quinazolin-6-ylmethyl]-4-trifluoromethyl-sulfanyl-benzamide; 1-(3-chloro-4-methyl-phenyl)-3-[3-(2,6-dioxo-piperidin-3-yl)-2-methyl-4-oxo-3,4-dihydro-quinazolin-6-ylmethyl]-urea; N-[3-(2,6-dioxo-piperidin-3-yl)-2-methyl-4-oxo-3,4-dihydro-quinazolin-6-ylmethyl]-3-trifluoromethyl-benzamide; N-[3-(2,6-dioxo-piperidin-3-yl)-2-methyl-4-oxo-3,4-dihydro-quinazolin-6-ylmethyl]-4-trifluoromethoxy-benzamide; 3,4-dichloro-N-[3-(2,6-dioxo-piperidin-3-yl)-2-methyl-4-oxo-3,4-dihydro-quinazolin-5-ylmethyl]-benzamide; and N-[3-(2,6-dioxo-piperidin-3-yl)-2-methyl-4-oxo-3,4-dihydro-quinazolin-6-ylmethyl]-4-trifluoromethyl-benzamide. From the tests, it was determined that IC$_{50}$ values of the tested compounds were in the range of 0.01 to 5.5 µM.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

All of the patents, patent applications and publications referred to herein are incorporated herein in their entireties. Citation or identification of any reference in this application is not an admission that such reference is available as prior art to this invention. The full scope of the invention is better understood with reference to the appended claims.

What is claimed is:
1. A compound of formula (I):

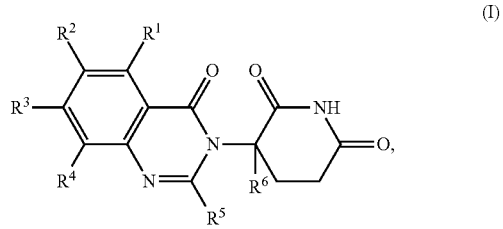

or a pharmaceutically acceptable salt, solvate, or stereoisomer thereof, wherein:

$R^1$ is hydrogen;
$R^4$ is halo; —(CH$_2$)$_n$OH; (C$_1$-C$_6$)alkyl, optionally substituted with one or more halo; (C$_1$-C$_6$)alkoxy, optionally substituted with one or more halo; or
—(CH$_2$)$_n$NHR$^a$, wherein R$^a$ is:
hydrogen;
(C$_1$-C$_6$)alkyl, optionally substituted with one or more halo;
—(CH$_2$)$_n$-(6 to 10 membered aryl);
—C(O)—(CH$_2$)$_n$-(6 to 10 membered aryl) or —C(O)—(CH$_2$)$_n$-(6 to 10 membered heteroaryl), wherein the aryl or heteroaryl is optionally substituted with one or more of: halo; —SCF$_3$; (C$_1$-C$_6$)alkyl, said alkyl itself optionally substituted with one or more halo; or (C$_1$-C$_6$)alkoxy, said alkoxy itself optionally substituted with one or more halo;
—C(O)—(C$_1$-C$_8$)alkyl, wherein the alkyl is optionally substituted with one or more halo;
—C(O)—(CH$_2$)$_n$—(C$_3$-C$_{10}$-cycloalkyl);
—C(O)—(CH$_2$)$_n$—NR$^b$R$^c$, wherein R$^b$ and R$^c$ are each independently:
hydrogen;
(C$_1$-C$_6$)alkyl, optionally substituted with one or more halo;
(C$_1$-C$_6$)alkoxy, optionally substituted with one or more halo; or
6 to 10 membered aryl, optionally substituted with one or more of: halo;
(C$_1$-C$_6$)alkyl, itself optionally substituted with one or more halo; or ($C_1$-$C_6$)alkoxy, itself optionally substituted with one or more halo;
—C(O)—($CH_2$)$_n$—O—($C_1$-$C_6$)alkyl; or
—C(O)—($CH_2$)$_n$—O—($CH_2$)$_n$-(6 to 10 membered aryl);

$R^2$ and $R^3$ together form a 5 or 6 membered ring, optionally substituted with one or more of:
halo; ($C_1$-$C_6$)alkyl, optionally substituted with one or more halo; and ($C_1$-$C_6$)alkoxy, optionally substituted with one or more halo;

$R^5$ is: hydrogen; —($CH_2$)$_n$OH; phenyl; —O—($C_1$-$C_6$)alkyl; or ($C_1$-$C_6$)alkyl, optionally substituted with one or more halo;

$R^6$ is: hydrogen; or ($C_1$-$C_6$)alkyl, optionally substituted with one or more halo; and n is 0, 1, or 2.

2. A compound of formula (VII):

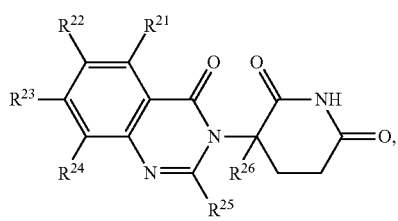

(VII)

or a pharmaceutically acceptable salt, solvate, or stereoisomer thereof, wherein:

$R^{21}$ is hydrogen;

$R^{24}$ is halo; —($CH_2$)$_n$OH; ($C_1$-$C_6$)alkyl, optionally substituted with one or more halo; ($C_1$-$C_6$)alkoxy, optionally substituted with one or more halo;

$R^{22}$ and $R^{23}$ together form a 5 to 6 membered ring, optionally substituted with one or more of:
halo; ($C_1$-$C_6$)alkyl, optionally substituted with one or more halo; and ($C_1$-$C_6$)alkoxy, optionally substituted with one or more halo;

$R^{25}$ is: hydrogen; —($CH_2$)$_n$OH; phenyl; —O—($C_1$-$C_6$)alkyl; or ($C_1$-$C_6$)alkyl, optionally substituted with one or more halo;

$R^{26}$ is: hydrogen; or ($C_1$-$C_6$)alkyl, optionally substituted with one or more halo; and n is 0, 1, or 2.

3. A pharmaceutical composition comprising a compound of claim 1, or a pharmaceutically acceptable salt, solvate, or stereoisomer thereof.

4. A pharmaceutical composition comprising a compound of claim 2, or a pharmaceutically acceptable salt, solvate, or stereoisomer thereof.

* * * * *